US011317812B2

(12) United States Patent
Onoe et al.

(10) Patent No.: US 11,317,812 B2
(45) Date of Patent: May 3, 2022

(54) OPTICAL SCANNING DEVICE, CATHETER DEVICE, AND DISTANCE MEASURING DEVICE

(71) Applicant: HITACHI, LTD., Tokyo (JP)

(72) Inventors: Shinsuke Onoe, Tokyo (JP); Takahiro Matsuda, Tokyo (JP); Yoshiho Seo, Tokyo (JP); Satoshi Ouchi, Tokyo (JP); Tomohiko Tanaka, Tokyo (JP); Taiichi Takezaki, Tokyo (JP); Ryo Imai, Tokyo (JP)

(73) Assignee: HITACHI, LTD., Tokyo (JP)

( * ) Notice: Subject to any disclaimer, the term of this patent is extended or adjusted under 35 U.S.C. 154(b) by 553 days.

(21) Appl. No.: 16/223,146

(22) Filed: Dec. 18, 2018

(65) Prior Publication Data

US 2019/0183348 A1 Jun. 20, 2019

(30) Foreign Application Priority Data

Dec. 19, 2017 (JP) .............................. JP2017-242635

(51) Int. Cl.
*G01S 17/08* (2006.01)
*A61B 5/00* (2006.01)
*G02B 26/10* (2006.01)
*H01L 41/04* (2006.01)
*H01L 41/09* (2006.01)
(Continued)

(52) U.S. Cl.
CPC .......... *A61B 5/0095* (2013.01); *A61B 5/0062* (2013.01); *A61B 5/0084* (2013.01); *G01N 29/2418* (2013.01); *G01S 7/4817* (2013.01); *G01S 17/08* (2013.01); *G02B 26/103* (2013.01); *H01L 41/042* (2013.01);
(Continued)

(58) Field of Classification Search
CPC .. G02B 26/103; G02B 26/10; G01N 29/2418; H01L 41/042
See application file for complete search history.

(56) References Cited

U.S. PATENT DOCUMENTS 8,411,922 B2 * 4/2013 Lee .................... A61B 1/00172
382/131
2018/0146931 A1 * 5/2018 Abe ........................ A61B 5/748

FOREIGN PATENT DOCUMENTS

JP     2004-029094 A     1/2004
JP     2008-514342 A     5/2008
(Continued)

OTHER PUBLICATIONS

Japanese Office Action received in corresponding Japanese Application No. 2017-242635 dated Mar. 2, 2021.

*Primary Examiner* — Maurice C Smith
(74) *Attorney, Agent, or Firm* — Mattingly & Malur, PC

(57) ABSTRACT

An optical scanning device includes: an optical scanning unit configured to repeatedly scan an irradiation destination of irradiation light to a predetermined trajectory; a light emission control unit configured to control light emission of the irradiation light to irradiate irradiation points to the predetermined trajectory; and a driving signal generation unit configured to generate a driving signal for driving the optical scanning unit, wherein the light emission control unit irradiates the irradiation points to the predetermined trajectory so that the irradiation points are substantially uniformly dispersed in a region in which a density of the irradiation points is relatively low in a region in which the irradiation light is irradiated.

20 Claims, 30 Drawing Sheets

(51) Int. Cl.
*G01N 29/24* (2006.01)
*G01S 7/481* (2006.01)
G02B 26/08 (2006.01)
G01S 17/89 (2020.01)

(52) U.S. Cl.
CPC .......... *H01L 41/0966* (2013.01); *G01S 17/89* (2013.01); *G02B 26/0858* (2013.01); *G02B 26/10* (2013.01)

(56) References Cited

FOREIGN PATENT DOCUMENTS

| | | | |
|---|---|---|---|
| JP | 2013-121455 A | 6/2013 | |
| JP | 2016-007274 A | 1/2016 | |
| JP | 2017-529913 A | 10/2017 | |
| WO | 2006/041452 A1 | 4/2006 | |
| WO | WO-2015098114 A1 * | 7/2015 | ............ G02B 23/26 |
| WO | 2017/163386 A1 | 3/2018 | |

* cited by examiner

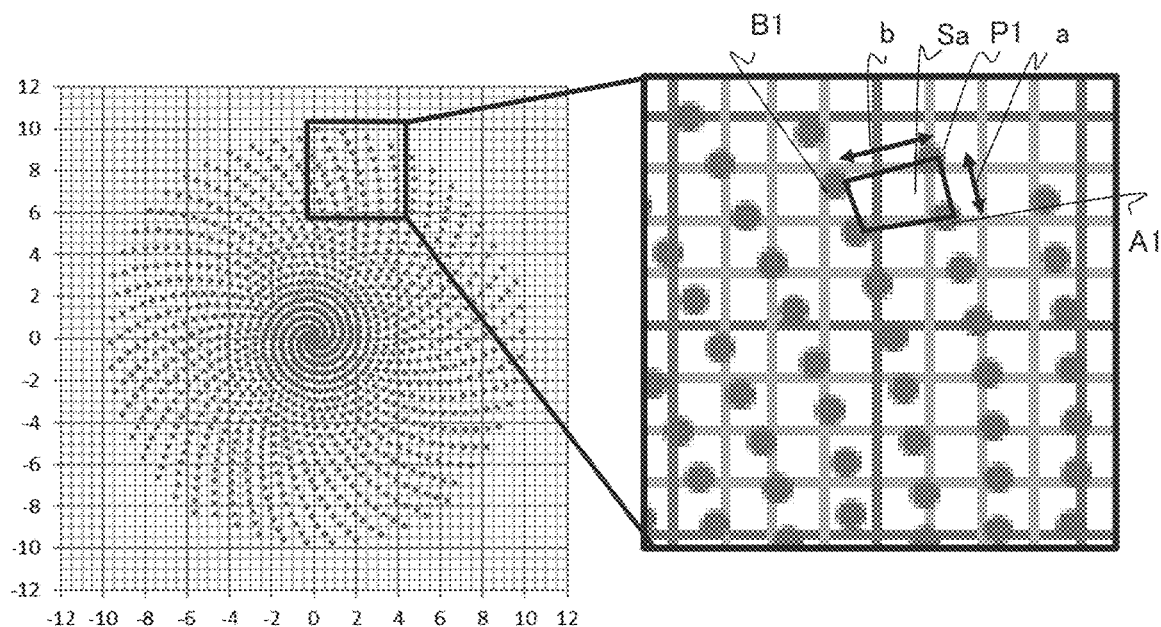
FIG.7A  $f_{drv}$=10.19kHz, $f_{dot}$=50kHz
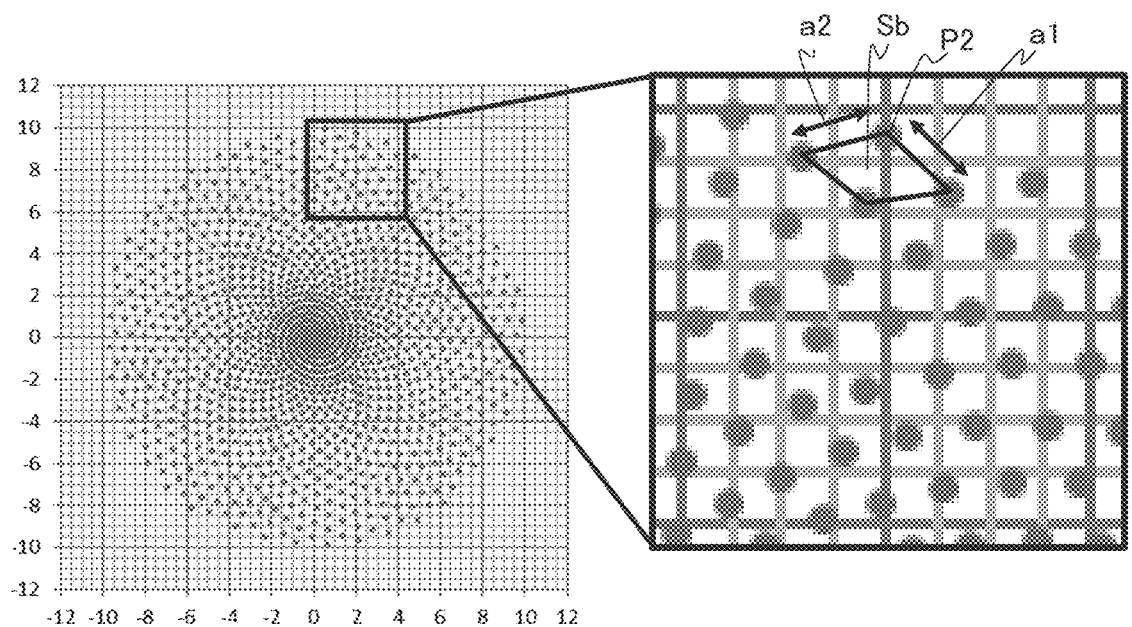
FIG.7B  $f_{drv}$=10.24kHz, $f_{dot}$=50kHz

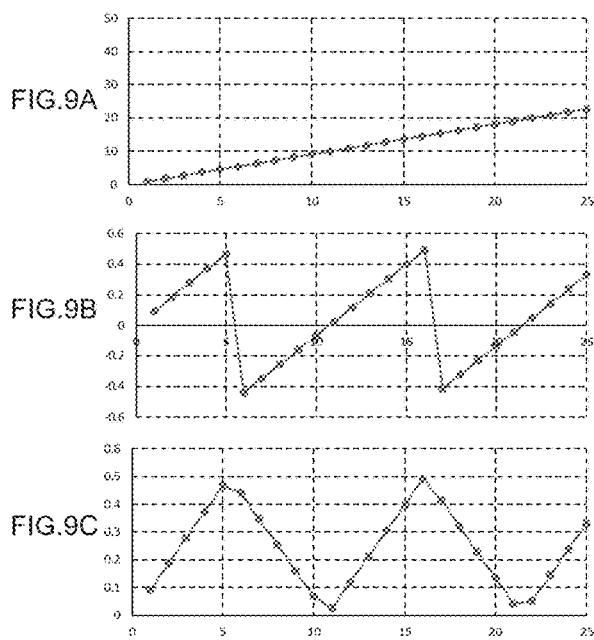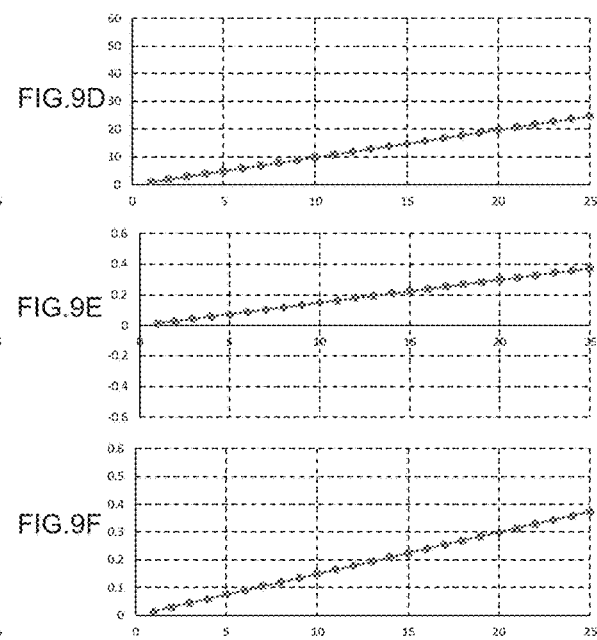
FIG.9A FIG.9B FIG.9C FIG.9D FIG.9E FIG.9F $f_{drv}$=1.000kHz　　　　$f_{drv}$=0.998kHz　　　　$f_{drv}$=0.996kHz

OPTICAL SCANNING DEVICE, CATHETER DEVICE, AND DISTANCE MEASURING DEVICE

This application claims the priority based on the Japanese Patent Application No. 2017-242635 filed on Dec. 19, 2017. The entire contents of which are incorporated herein by reference for all purpose.

BACKGROUND

Technical Field

The present invention relates to an optical scanning device, a catheter device, and a distance measuring device.

Related Art

In the treatment of angiostenosis and the like, in order to specify a lesion site, the entire blood vessel has been captured using X-rays. However, there is an opinion that the imaging using X-rays is not preferable because of the occurrence of exposure. Therefore, intravascular catheter imaging using light or ultrasound has been performed instead of the X-ray imaging.

Compared with the X-ray imaging, the intravascular catheter imaging makes it possible to reduce a physical burden on a patient and perform local imaging. In addition, the treatment of the angiostenosis using the catheter is being used more and more because of reducing a burden on a patient compared to an open chest operation.

For an optical scanning device for driving an optical fiber related to the intravascular catheter imaging, for example, JP 2008-514342 A discloses "In fact, environmental variables or manufacturing variables such as aberration in nonlinear driving electronic devices, nonlinear driving mechanism, and an imaging system of a fiber scanning system, sensitivity of a scanning fiber device near a resonance frequency, and other factors increase inaccuracy of a position of an irradiation spot in a scanning pattern and increase a distortion in an image constructed by the scanning fiber device".

Further, for example, JP 2004-029094 A discloses "In a light input/output control device for an optical scanning device controlling timing at which light from a light source is output to an optical scanning unit scanning an inside of a predetermined region two-dimensionally by fluctuating a movable plate on which a reflecting surface is formed in two axis directions orthogonal to each other and swinging a traveling direction of light incident on the reflecting surface or timing at which light from a scanning object is input, the whole of the predetermined region is divided into lattice shapes continued in an X direction and a Y direction, each lattice-shaped block divided is defined as a target position of light output or light input, an arrival of a scanning trajectory to the target position is detected by the two-dimensional scanning, thereby controlling the timing of the light output or the light input at the target position".

SUMMARY

In the optical scanning device disclosed in JP 2008-514342 A, light is scanned so as to repeatedly draw a spiral trajectory by driving a vibration unit.

Hereinafter, in the present specification, emitting light from the light source is referred to as "emission", and impinging light emitted from the optical scanning device on an object is referred to as "irradiation". For example, in the case of a catheter device or an imaging device, light is irradiated to an observation object or an imaging object as an object. In the case of a distance measuring device, light is irradiated to a measurement object as an object. In addition, in the case of an image device displaying an image, light is irradiated to a projection plane as an object.

In addition, in the present specification, a point of light discretely irradiated to a spiral trajectory is referred to as an irradiation point.

In the present specification, the irradiation point will be described in detail with reference to FIG. 29. FIG. 29 is a diagram for explaining the definition of the irradiation points. Light emitted from an optical scanning unit 61 is irradiated to a projection plane 63 perpendicular to the light. The irradiation point draws a spiral trajectory from a central part of the projection plane 63 toward a circumferential part.

A curved line A in FIG. 29 is the spiral trajectory on the projection plane 63, and an arrow B shows a scanning direction. Points 64 to 66 indicate spots of light irradiated to the projection plane 63, and become irradiation points. That is, the irradiation point is a spot of light irradiated to the projection plane 63 perpendicular to a central axis 62 of the light emitted from the optical scanning unit 61.

In addition, a period in which the spiral trajectory is scanned once is referred to as one frame. One frame can be paraphrased as the smallest repeating unit of the trajectory on which the optical scanning is performed.

A set of irradiation points irradiated for a time taken to scan the spiral trajectory once, that is, a period of one frame is called an irradiation point group. In addition, an inside of a circle on an outermost circumference of the spiral trajectory is defined as a region in which an irradiation light is irradiated. In addition, one rotation of a substantially circular trajectory constituting the spiral trajectory is referred to as a turn. For example, when the number of intersections between a diameter of the irradiation region and the spiral trajectory is 500, the number of turns of the spiral trajectory is expressed as 250.

Here, the case in which a light emission frequency of the light emitted from the optical scanning unit 61 is 50 kHz, a driving frequency of a vibration unit (not shown) for scanning light is 10.19 kHz, and the number of turns of the spiral trajectory is 250 is considered. In this case, a ratio of the light emission frequency of the light and the driving frequency of the vibration unit is about 5:1. Therefore, the number of irradiation points irradiated during one rotation of the substantially circular trajectory constituting the spiral trajectory is about 5.

Next, FIGS. 30A to 30C are diagrams showing simulation results of the irradiation points irradiated while the spiral trajectory is drawn once. FIGS. 30A to 30C show that the region in which the irradiation light is irradiated is normalized by a circle having a radius of 10.

Here, FIG. 30A shows simulation results in the case in which the light emission frequency of light is 50 kHz, the driving frequency of the vibration unit for scanning light is 10.19 kHz, and the driving frequency of the spiral trajectory is 250. In this case, the irradiation points are arranged so as to appear as a helical pattern constituted by a large number of curved lines.

Here, FIG. 30B shows simulation results in the case in which the light emission frequency of light is 50 kHz, the driving frequency of the vibration unit for scanning light is 10.00 kHz, and the frequency of the spiral trajectory is 250. In this case, the irradiation points are arranged so as to appear as five linear patterns extending at equal angles from the central part of the projection plane.

Here, FIG. 30C shows simulation results in the case in which the light emission frequency of light is 50 kHz, the driving frequency of the vibration unit for scanning light is 10.03 kHz, and the frequency of the spiral trajectory is 250. In this case, the irradiation points are arranged so as to appear as a helical pattern with fewer curved lines compared with FIG. 30A.

It is understood from FIGS. 30A to 30C that when the light emission frequency of light is an integral multiple of the driving frequency of the vibration unit or is close thereto, the irradiation points are arranged so as to appear as the helical or linear pattern. The present inventors found from additional simulation results that according to the relationship between the light emission frequency of light, the driving frequency of the vibration unit, and the number of turns of the spiral trajectory, a deviation occurs in the arrangement of the irradiation points in the irradiation region, such that the irradiation points appear as the helical pattern, or the number of helical patterns is extremely reduced.

Hereinafter, the arrangement of the irradiation points shown in FIGS. 30A to 30C is collectively referred to as "helical pattern".

As a method for suppressing the deviation of the arrangement of the irradiation points in the irradiation region, JP 2004-029094 A discloses a configuration capable of arranging irradiation points at almost equal intervals over the entire surface of two-dimensional scanning on a projection plane by controlling irradiation timing of light.

However, controlling the irradiation timing of light means waiting until the irradiation timing reaches the desired timing. Therefore, the waiting time is a waste of time. This can be paraphrased as thinning out of light irradiation, and the thinning out of the light irradiation means a loss of light from the viewpoint of effectively utilizing light. If there is a loss of light in light emission, it is impossible to improve S/N of the captured image which could be realized originally.

For example, when the imaging is performed by irradiating light, the case in which the light irradiation is performed plural times in a region corresponding to the same image of the captured image by making an interval between scanning trajectories dense (that is, the case in which the thinning out of the light irradiation is not performed) is considered. In this case, even if the light irradiation is performed plural times, for example, if the first or last light irradiation is adopted, it is possible to generate the captured image. In addition, it is possible to improve the S/N of the captured image by averaging the results obtained by performing the light irradiation plural times. However, in a case where the thinning out of the light irradiation is performed, the captured image can be generated, but when not only wasted time is generated, but also noise occurs in the results of the light irradiation, it may not possible to flat the noise even when the results of the thinned out light irradiation are averaged and improve the S/N of the captured image.

The present invention has been made in view of such a situation, and it is an object of the present invention to arrange irradiation points without thinning out the irradiation of light and biasing the irradiation points.

The present application includes a plurality of means for solving at least a part of the above problems, and the example thereof is as follows. In order to solve the above problems, an optical scanning device according to one aspect of the present invention includes: an optical scanning unit configured to repeatedly scan an irradiation destination of irradiation light on a predetermined trajectory; a light emission control unit configured to control emission of the irradiation light to irradiate irradiation points to the predetermined trajectory; and a driving signal generation unit configured to generate a driving signal for driving the optical scanning unit, wherein the light emission control unit irradiates the irradiation points to the predetermined trajectory so that the irradiation points are substantially uniformly dispersed in a region having a relatively lower density of irradiation points in a region in which the irradiation light is irradiated.

According to the present invention, it is possible to arrange the irradiation points without thinning out the light irradiation and biasing the irradiation points.

The problems, configurations, and effects other than those described above will be clarified from the description of the embodiments below.

BRIEF DESCRIPTION OF DRAWINGS

FIGS. 7A and 7B are diagrams showing simulation results of positions of irradiation points;

FIGS. 9A to 9F are diagrams for explaining a case in which the number of curved lines forming a helical pattern is extremely small;

DETAILED DESCRIPTION

Figure 1:
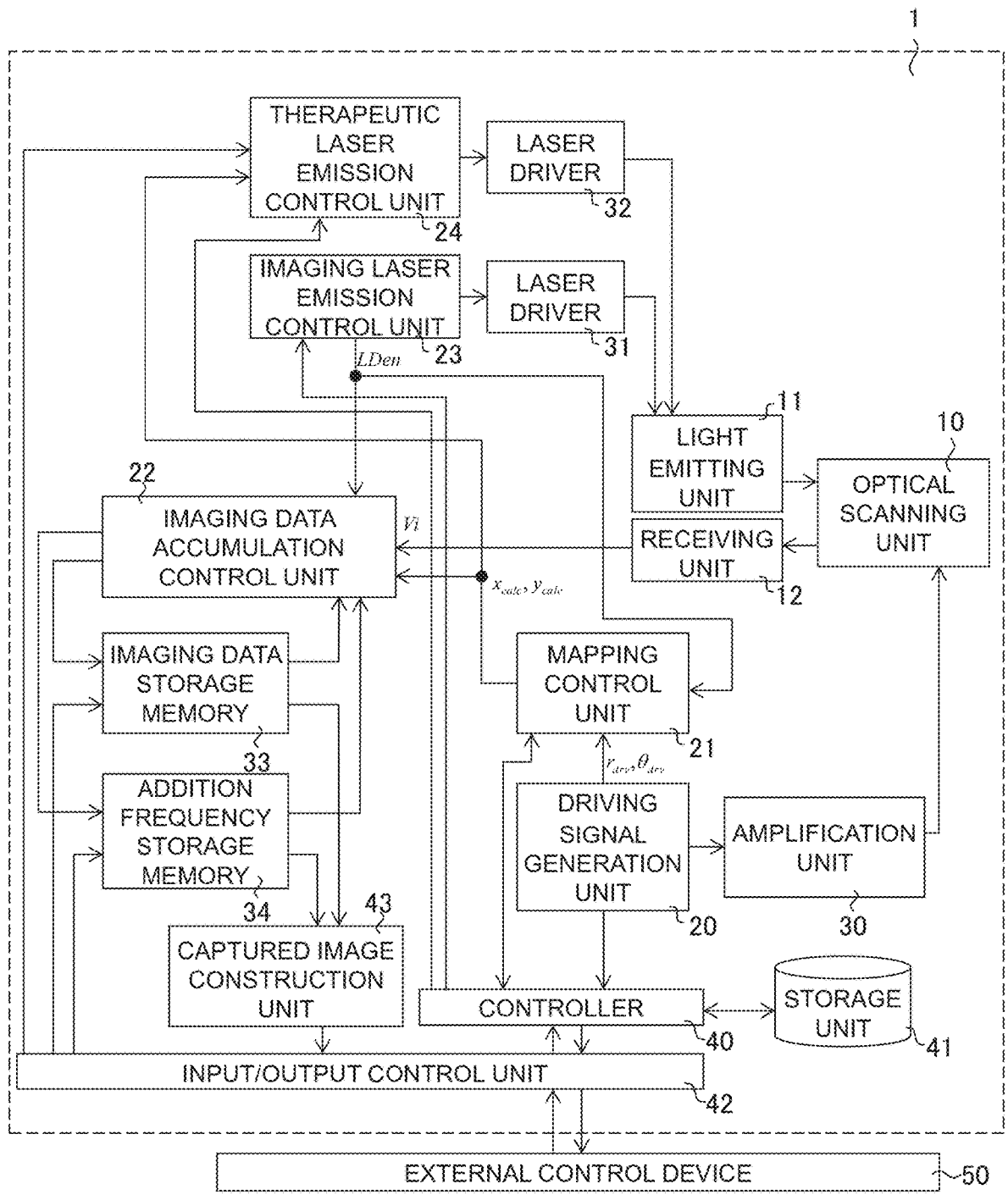
FIG. 1 is a block diagram showing a configuration example of a catheter device 1 according to a first embodiment.

Hereinafter, a plurality of embodiments according to the present invention will be described with reference to the drawings. In all the drawings for explaining each of the embodiments, the same members are denoted by the same reference numerals in principle, and the repetitive description thereof will be omitted. In addition, in the following embodiments, it goes without saying that components (including element, steps, and the like) are not necessarily stated except the case in which they need to be explicitly stated, in particular, the case in which it is considered that they are obviously essential in principle, and the like. In addition, it goes without saying that the terms "comprising A", "consisting of A", "having A", and "including A" do not exclude other elements except the case in which only the element needs to be specifically stated, and the like. Similarly, in the following embodiments, it is to be noted that when referring to shapes, positional relationships and the like of components and the like, those substantially approximating or similar to the shapes and the like are included except the case in which they need to be explicitly stated, in particular, the case in which it is considered that they are obviously unlikely in principle, and the like.

<As to Catheter Device 1 According to First Embodiment of the Present Invention>

FIG. 1 is a block diagram showing a configuration example of a catheter device 1 according to a first embodiment of the present invention. The catheter device 1 uses a photoacoustic imaging method.

The catheter device 1 includes an optical scanning unit 10, a light emitting unit 11, a receiving unit 12, a driving signal generation unit 20, a mapping control unit 21, an imaging data accumulation control unit 22, an imaging laser emission control unit 23, and a therapeutic laser emission control unit 24.

In addition, the catheter device 1 includes an amplification unit 30, an imaging laser driver 31, a therapeutic laser driver 32, an imaging data storage memory 33, an addition frequency storage memory 34, a controller 40, a storage unit 41, an input/output control unit 42, and a captured image construction unit 43.

The optical scanning unit 10 irradiates a laser beam emitted from the light emitting unit 11 to an observation object (for example, an inside of a blood vessel) as an object via a light guide path 102 (FIGS. 2A and 2B), and scans an irradiation destination thereof to repeatedly draw a predetermined trajectory.

The light emitting unit 11 includes an imaging laser light source emitting an imaging laser beam that is a low power pulse laser, and a therapeutic laser light source (none of which is shown) emitting a therapeutic laser beam that is a high power pulse laser.

The receiving unit 12 includes a photoacoustic element 121 (FIG. 2A and FIG. 2B) and is integrally formed as a cylindrical catheter together with the optical scanning unit 10.

When the observation object is a living body such as the inside of the blood vessel, if the imaging laser beam is irradiated, the observation object emits heat and its volume is expanded, and a sound wave is generated when the volume is expanded. The photoacoustic element 121 of the receiving unit 12 detects the sound wave. That is, the receiving unit 12 receives the sound wave generated from the observation object by the irradiation of the laser beam. In addition, the receiving unit 12 generates the photoacoustic signal corresponding to the result of receiving the sound wave and outputs the generated photoacoustic signal to the imaging data accumulation control unit 22.

Under the control of the controller 40, the driving signal generation unit 20 generates a plurality of driving signals for scanning the laser beam in the optical scanning unit 10. The driving signal generated by the driving signal generation unit 20 is amplified by the amplification unit 30 and applied to a piezoelectric element of a vibration unit 101 (FIG. 2A and FIG. 2B) provided in the optical scanning unit 10. As a result, the vibration unit 101 vibrates to scan the laser beam.

The mapping control unit 21 calculates to which coordinates the photoacoustic signal corresponding to the sound wave received by the receiving unit 12 corresponds in pixel information on an image based on information from the driving signal generation unit 20. The coordinates ($x_{calc}$, $y_{calc}$) calculated are supplied to the imaging data accumulation control unit 22.

The imaging data accumulation control unit 22 controls the photoacoustic signal input from the receiving unit 12 to be associated with the pixel information and accumulated in the imaging data storage memory 33. The imaging data storage memory 33 accumulates the photoacoustic signal under the control of the imaging data accumulation control unit 22.

The imaging laser emission control unit 23 generates an imaging laser emission control signal for controlling the emission of the imaging laser under the control of the controller 40. The imaging laser emission control signal is supplied to the imaging laser light source provided in the light emitting unit 11 via the imaging laser driver 31.

The imaging laser emission control unit 23 generates the imaging laser emission control signal with which the imaging laser light source emits light repeatedly at a predetermined light emission frequency $f_{dot}$. The predetermined light emission frequency $f_{dot}$ is, for example, 50 kHz and is designated from the controller 40.

In addition, the imaging laser emission control unit 23 generates an $LD_{en}$ signal which becomes High at timing at which the imaging laser light source emits light and becomes Low at timing at which the imaging laser light source is turned off and supplies the generated $LD_{en}$ signal to the imaging data accumulation control unit 22 and the mapping control unit 21. It is to be noted that the imaging laser emission control unit 23 may be configured to set a predetermined time delay with respect to the timing at which the imaging laser light source emits light under the control of the controller 40.

The therapeutic laser emission control unit 24 uses target coordinates notified from the input/output control unit 42 and the coordinates ($x_{calc}$, $y_{calc}$) notified from the mapping control unit 21 under the control of the controller 40 to generate the therapeutic laser emission control signal for controlling the emission of the therapeutic laser. Specifically, the therapeutic laser emission control unit 24 outputs the therapeutic laser emission control signal for the emission of the therapeutic laser light source for a period in which the target coordinates notified from the input/output control unit 42 coincide with the coordinates ($x_{calc}$, $y_{calc}$) notified from the mapping control unit 21. The therapeutic laser emission control signal is supplied to the therapeutic laser light source provided in the light emitting unit 11 via the therapeutic laser driver 32.

The controller 40 is realized by, for example, a central processing unit (CPU) executing a predetermined program, and controls each component of the catheter device 1.

The storage unit 41 stores information necessary for processing by the controller 40 or the like constituting the catheter device 1 or stores the generated information. The storage unit 41 is a storage device such as a random access memory (RAM) or a flash memory and functions as a storage area in which programs or data are temporarily read. The storage unit 41 may be writable and readable storage media such as a hard disk drive (HDD), a compact disc-recordable (CD-R), a digital versatile disk-random access memory (DVD-RAM), and a solid state drive (SSD), a storage media driving device, and the like.

The input/output control unit 42 connects an external control device 50 to the catheter device 1 and communicates predetermined data. For example, the input/output control unit 42 can transmit the image captured by the catheter device 1 to the external control device 50.

The captured image construction unit 43 (corresponding to an imaging unit of the present invention) generates the captured image based on the photoacoustic signal stored in the imaging data storage memory 33 (described later in detail).

The driving signal generation unit 20, the mapping control unit 21, the imaging data accumulation control unit 22, the captured image construction unit 43, the imaging laser emission control unit 23, and the therapeutic laser emission control unit 24 may be realized as a logical unit by, for example, a field programmable gate array (FPGA), or may also be mounted as hardware such as an application specific integrated circuit (ASIC).

Figure 2A:
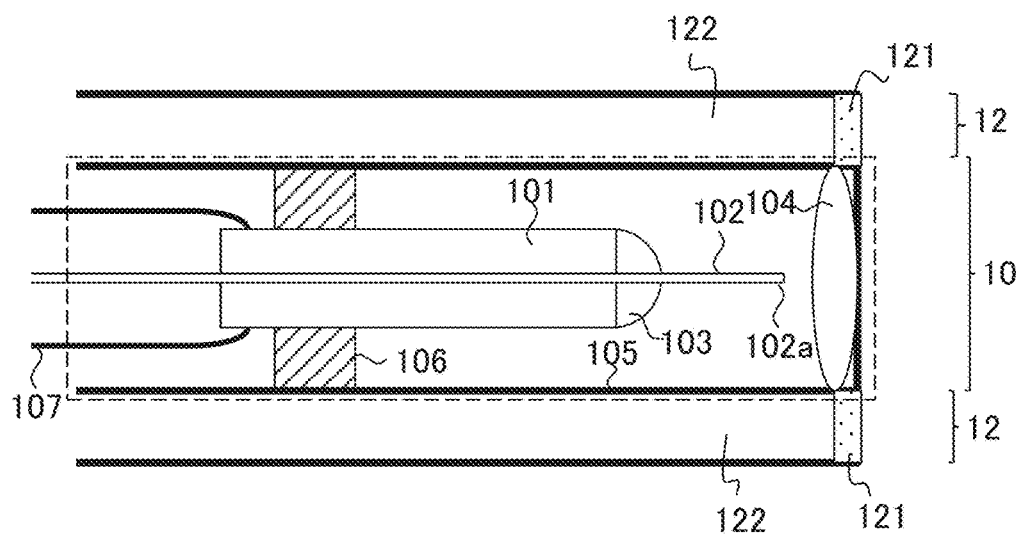
FIGS. 2A and 2B are diagrams showing a configuration example of an optical scanning unit 10 and a receiving unit 12 in FIG. 1.
Figure 2B:
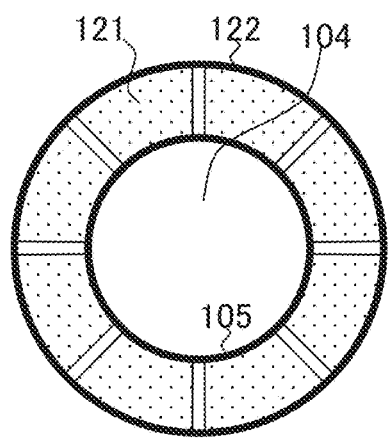

Next, FIGS. 2A and 2B show a configuration example of the optical scanning unit 10 and the receiving unit 12 of FIG. 1. FIG. 2A is a longitudinal cross-sectional view of the optical scanning unit 10 and the receiving unit 12 integrally formed as a cylindrical catheter, and shows a configuration example of a tip part of the catheter. The right side of FIG. 2A is the tip of the catheter. FIG. 2B shows a front view of the cylindrical catheter when viewed from the tip part (when viewed from the right side in FIG. 2A).

The optical scanning unit 10 includes the vibration unit 101, the light guide path 102, a bonding portion 103, a lens 104, a housing 105, a support member 106, and an electric wiring 107. The receiving unit 12 includes the photoacoustic element 121 and a housing 122.

The vibration unit 101 is an actuator which vibrates a light emitting end 102a of the light guide path 102 in order to scan the laser beam, and is constituted by, for example, a piezoelectric element.

The vibration unit 101 is constituted by arranging a plurality of electrodes 1011 to 1015 (FIG. 3) on an inner circumference or an outer circumference of a cylindrical piezoelectric element whose central part is hollow. Driving signals are applied to the electrodes 1011 to 1014 provided in the vibration unit 101 through the electric wiring 107. As a result, the vibration unit 101 is vibrated.

The light guide path 102 is installed in the hollow part of the central part of the vibration unit 101, and the vibration unit 101 and the light guide path 102 are fixed by the bonding portion 103. The vibration unit 101 is fixed inside the cylindrical housing 105 by the support member 106.

The light guide path 102 is constituted by, for example, an optical fiber in a single mode or a multi mode. The optical fiber includes a coat layer, a clad layer, and a core layer, and light is confined in the core layer and is propagated. It is to be noted that the optical fiber from which the coat layer is peeled off may be adopted for the light guide path 102. As a result, a diameter size of the optical scanning unit 10 can be reduced.

The lens 104 is formed on a spherical surface or an aspherical surface using glass or resin. It is to be noted that the lens 104 may be a Fresnel lens, a refractive index distribution type gradient index (GRIN) lens or the like. In addition, the lens 104 may be integrated with the light emitting end 102a of the light guide path 102. In addition, the lens 104 may be constituted by a plurality of lenses instead of a single lens.

The light emitting end 102a of the light guide path 102 is formed in a state in which the bonding portion 103 as a fixed end protrudes in a cantilever shape. As a result, when the vibration unit 101 vibrates, the light emitting end 102a of the light guide path 102 which is a free end is resonated. The laser beam emitted from the light emitting end 102a of the light guide path 102 is irradiated to a target surface via the lens 104 by the resonance, and the irradiation destination thereof is scanned on a predetermined orbit.

In the tip side (right side in FIG. 2A) of the optical scanning unit 10, the plurality of photoacoustic elements 121 configuring the receiving unit 12 are arranged on an outer side of the housing 105 in a ring shape. The photoacoustic element 121 is constituted by, for example, the piezoelectric element or the like manufactured by, for example, a micro electro mechanical systems (MEMS) technology. In the example of FIG. 2B, eight photoacoustic elements 121 are arranged on an outer circumference of the lens 104. The photoacoustic element 121 detects the intensity of the sound wave, and generates a photoacoustic signal of a voltage signal that is changed in proportion to the intensity of the detected sound wave, and supplies the generated photoacoustic signal to the imaging data accumulation control unit 22.

The housing 122 of the receiving unit 12 is a structure for maintaining a mechanical strength (rigidity) of the tip of the catheter, and is integrally formed with the optical scanning unit 10 and the photoacoustic element 121.

Figure 3:
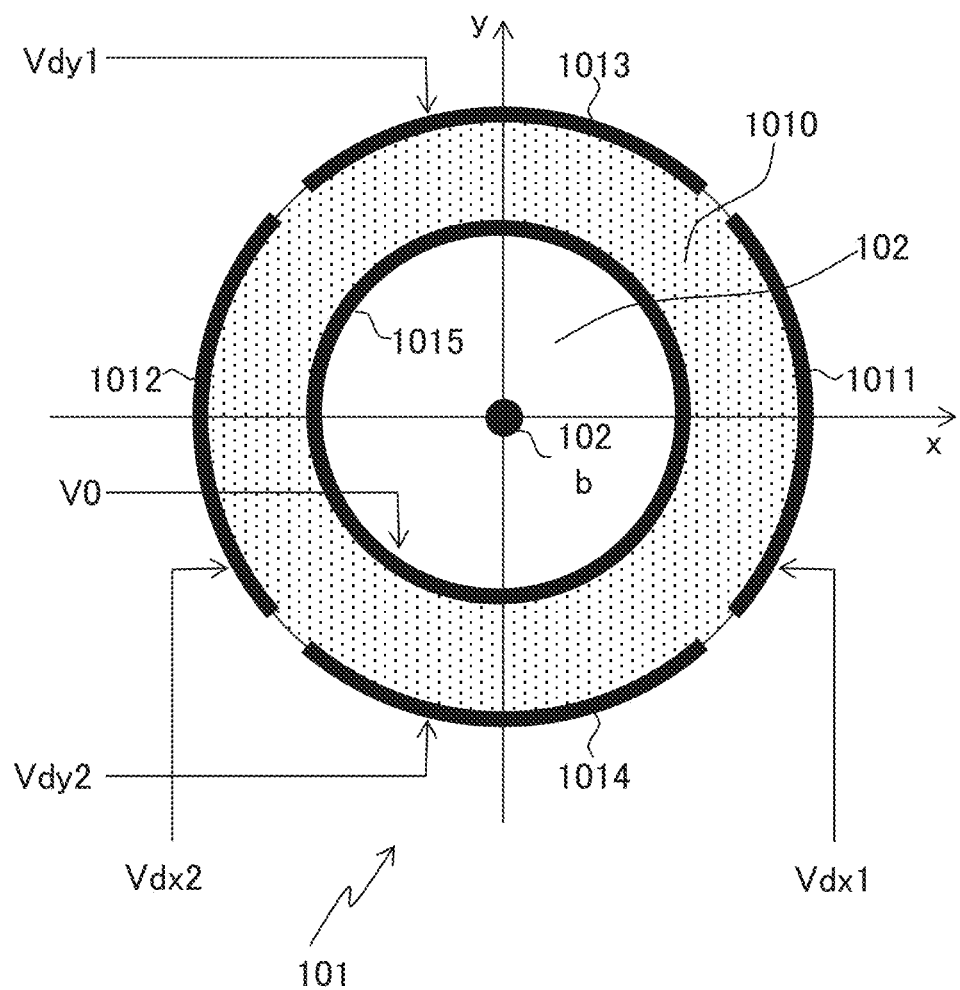
FIG. 3 is a cross-sectional view showing the configuration example of the optical scanning unit 10 of FIG. 1.

Next, FIG. 3 is a cross-sectional view of a plane orthogonal to a longitudinal direction of the light guide path 102 of the optical scanning unit 10.

The vibration unit 101 is configured by arranging electrodes 1011, 1012, 1013, and 1014 on an outer circumference of a hollow cylindrical piezoelectric element 1010 and arranging an electrode 1015 on an inner circumference of the piezoelectric element 1010. The electrodes 1011 to 1014 are connected to the electric wiring 107, and the electrode 1015 is grounded. It is to be noted that the electrode 1015 may be in a floating state without being grounded. In addition, four electrodes 1011 to 1014 may be arranged on the inner circumference and the electrode 1015 may be arranged on the outer circumference. A hollow part of the piezoelectric element 1010 is provided with the light guide path 102. The light guide path 102 has a core portion (core layer) 102b.

The electrodes 1011 to 1015 have a substantially rectangular shape which has a long side parallel with, for example, a longitudinal direction of the cylindrical piezoelectric element 1010, that is, a longitudinal direction of the light guide path 102.

It is possible to vibrate the light emitting end 102a which is the free end of the light guide path 102 by applying a sinusoidal voltage to a pair of electrode 1011 and electrode 1012 which face each other, and a pair of electrode 1013 and electrode 1014 among the electrodes 1011 to 1014. In addition, by shifting a phase of a sine wave to be applied to both pairs by approximately 90°, it is possible to vibrate the light emitting end 102a so that the light emitting end 102a draws a circular orbit. In addition, by temporally changing the amplitude of the sine wave applied, the light emitting end 102a can draw a spiral orbit. As a result, it is possible to perform two-dimensional scanning so that the irradiation destination of the light emitted from the light guide path 102 draws a spiral trajectory on the target surface (the surface of the object).

Here, an x axis and a y axis of a coordinate system used in the present specification are defined as shown in FIG. 3. In addition, a voltage applied to the electrode 1011 is defined as Vdx1, a voltage applied to the electrode 1012 is defined as Vdx2, a voltage applied to the electrode 1013 is defined as Vdy1, and a voltage applied to the electrode 1014 is defined as Vdy2. In addition, it is considered that the piezoelectric element 1010 functioning as the actuator is divided into four regions of a region sandwiched between the electrode 1011 and the electrode 1015, a region sandwiched between the electrode 1012 and the electrode 1015, a region sandwiched between the electrode 1013 and the electrode 1015, and a region sandwiched between the electrode 1014 and the electrode 1015.

Figure 4:
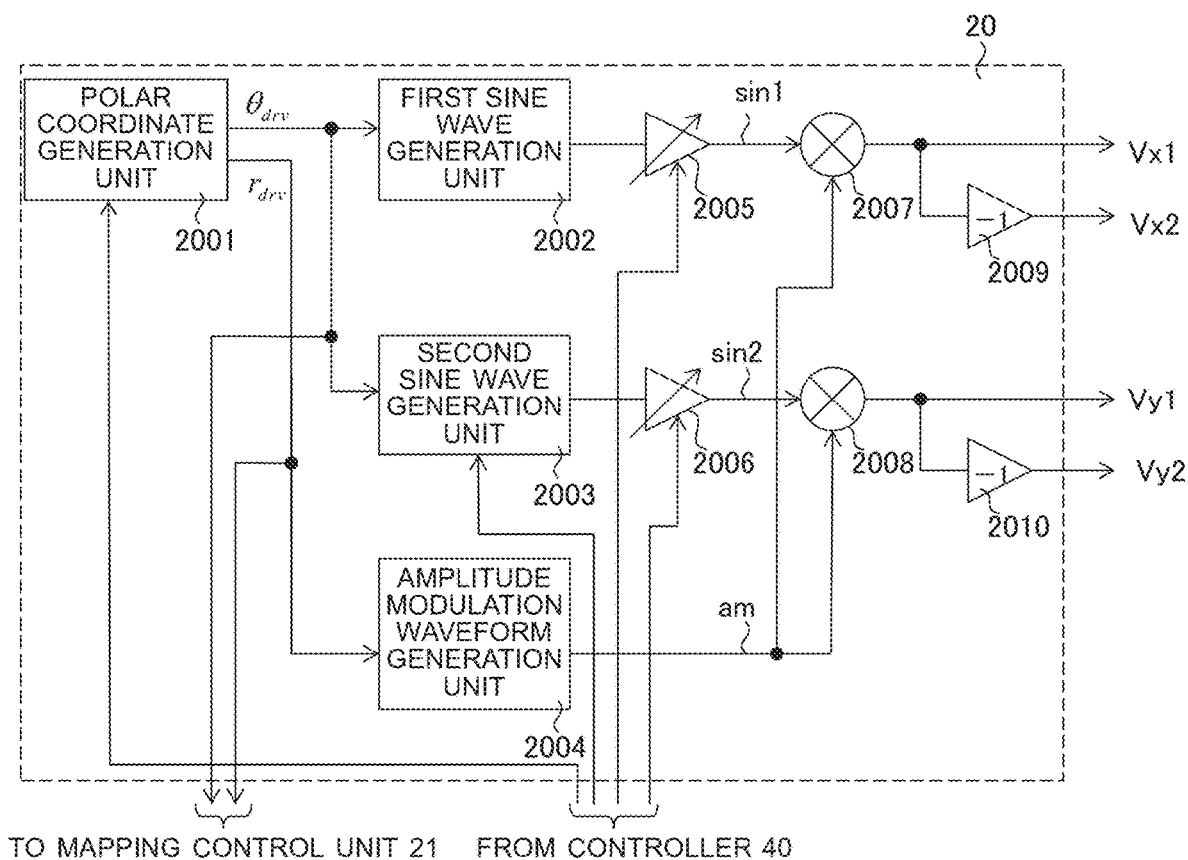
FIG. 4 is a block diagram showing a configuration example of a driving signal generation unit 20.

Next, FIG. 4 shows a configuration example of the driving signal generation unit 20. The driving signal generation unit 20 outputs four driving signals Vx1, Vx2, Vy1, and Vy2. The driving signal generation unit 20 includes a polar coordinate generation unit 2001, a first sine wave generation unit 2002, a second sine wave generation unit 2003, an amplitude modulation waveform generation unit 2004, a first variable gain unit 2005, a second variable gain unit 2006, a first multiplication unit 2007, a second multiplication unit 2008, a first inversion gain unit 2009, and a second inversion gain unit 2010.

The polar coordinate generation unit 2001 generates a radius $r_{drv}$ and an angle $\theta_{drv}$ as polar coordinates of the trajectory so that the trajectory of the irradiation destination of the laser beam on the projection plane (object) draws the spiral trajectory. Specifically, the polar coordinate generation unit 2001 acquires information on the driving frequency $f_{drv}$ of the vibration unit 101 and the number of turns $N_{frame}$ of the spiral trajectory from the controller 40, and generates the radius $r_{drv}$ and the angle $\theta_{drv}$. The radius $r_{drv}$ and the angle $\theta_{drv}$ are functions with time as a variable. The angle $\theta_{drv}$ is repeatedly changed from 0° to 360° with a change in time. The driving frequency $f_{drv}$ substantially coincides with the resonance frequency of the cantilever constituted by the light guide path 102. The generated radius $r_{drv}$ is supplied to the amplitude modulation waveform generation unit 2004 and the mapping control unit 21. The generated angle $\theta_{drv}$ is supplied to the first sine wave generation unit 2002, the second sine wave generation unit 2003, and the mapping control unit 21.

The first sine wave generation unit 2002 generates a first sine wave of the driving frequency $f_{drv}$ based on the angle $\theta_{drv}$. The amplitude of the first sine wave output from the first sine wave generation unit 2002 is changed by the first variable gain unit 2005 to become an X-axis driving sine wave sin1. An amplitude magnification in the first variable gain unit 2005 is controlled by the controller 40.

Based on the angle $\theta_{drv}$ and the control signal from the controller 40, the second sine wave generation unit 2003 generates a second sine wave of the driving frequency $f_{drv}$ which has a predetermined phase difference with respect to the first sine wave. The amplitude of the second sine wave output from the second sine wave generation unit 2003 is changed by the second variable gain unit 2006 to become a Y-axis driving sine wave sin2. An amplitude magnification in the second variable gain unit 2006 is controlled by the controller 40.

The amplitude modulation waveform generation unit 2004 generates an amplitude modulation waveform am based on the radius $r_{drv}$. The first multiplication unit 2007 multiplies the X-axis driving sine wave sin1 by the amplitude modulation waveform am. The waveform obtained as the multiplication result is output as the voltage Vx1 and is output as the voltage Vx2 while the amplitude thereof is inverted by the first inversion gain unit 2009.

The second multiplication unit 2008 multiplies the Y-axis driving sine wave sin2 by the amplitude modulation waveform am. The waveform obtained as the multiplication result is output as the voltage Vy1 and is output as the voltage Vy2 while the amplitude thereof is inverted by the second inversion gain unit 2010.

The voltages Vx1, Vx2, Vy1, and Vy2 output from the driving signal generation unit 20 are amplified by the amplification unit 30 at a later stage to become the voltages Vdx1, Vdx2, Vdy1, and Vdy2, and are applied to the electrodes 1011 to 1014 provided in the vibration unit 101 within the optical scanning unit 10.

Figure 5:
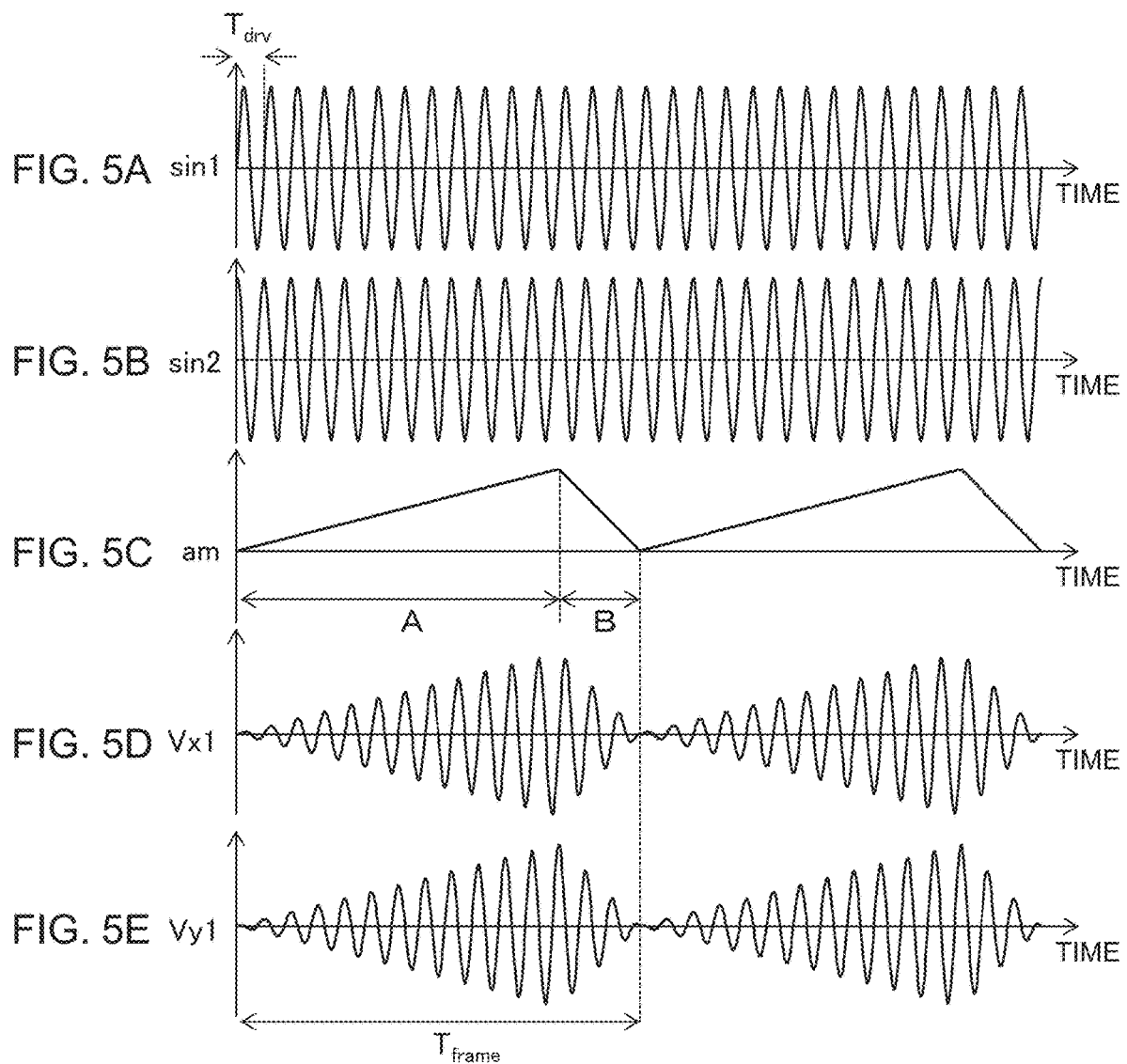
FIGS. 5A to 5E are diagrams showing examples of waveforms of signals generated by the driving signal generation unit 20.

Next, FIGS. 5A to 5E are diagrams for explaining the waveform such as the sine wave generated inside the driving signal generation unit 20. FIG. 5A shows the X-axis driving sine wave sin1, FIG. 5B shows the Y-axis driving sine wave sin2, and FIG. 5C shows the amplitude modulation waveform am.

Both the X-axis driving sine wave sin1 and the Y-axis driving sine wave sin2 are sine waves having the same cycle $T_{drv}$ ($=1/f_{drv}$). The X-axis driving sine wave sin1 and the Y-axis driving sine wave sin2 are provided with a phase difference of about 90° under the control of the controller 40. That is, when regarding the X-axis driving sine wave sin1 as the sine wave, the Y-axis driving sine wave sin2 can be considered as a cosine wave. The amplitudes of the X-axis driving sine wave sin1 and the Y-axis driving sine wave sin2 may differ depending on the magnifications in the first variable gain unit 2005 and the second variable gain unit 2006.

In the amplitude modulation waveform am, the same waveform is repeated for each cycle $T_{frame}$. For example, the amplitude modulation waveform am is a waveform in which amplitude is linearly increased from 0 in a period A shown in FIG. 5C, and amplitude is linearly decreased to return to 0 in a period B. It is to be noted that the period A shown in FIG. 5C corresponds to a lighting period of the laser beam and the period B corresponds to a light-out period of the laser beam.

FIG. 5D shows the waveform of the voltage Vx1, and FIG. 5E shows the waveform of the voltage Vy1. The period of the cycle $T_{frame}$ corresponds to one frame in capturing an image. One frame is the smallest repeating unit of the trajectory on which the optical scanning is performed, and may be paraphrased as the minimum repeating unit of the driving waveforms Vx1 and Vy1.

All the phase difference of the Y-axis driving sine wave sin2 with respect to the X-axis driving sine wave sin1, the magnification in the first variable gain unit 2005, and the magnification in the second variable gain unit 2006 are controlled by the controller 40, and the values are not changed for the cycle $T_{frame}$. That is, with respect to the voltage Vx1 and the voltage Vy1, the ratio of the phase difference and the amplitude is constant at any timing.

The driving frequency $f_{drv}$ is determined so as to correspond to the resonance frequency of the cantilever in which the bonding portion 103 of the optical scanning unit 10 becomes the fixed end and the light emitting end 102a of the light guide path 102 becomes the free end, such that the cantilever constituted by the light guide path 102 can resonate and the displacement of the light emitting end 102a can be increased. As a result, the amplitude of the trajectory of the irradiation destination of the laser beam can be expanded.

As described above, the vibration unit 101 provided in the optical scanning unit 10 is driven in the spiral shape by the driving signal generated by the driving signal generation unit 20. On the other hand, the imaging laser light source emits light in a pulsed shape by the imaging laser emission control unit 23, such that the irradiation point is irradiated to the spiral trajectory in the irradiation region of the observation surface. Therefore, in the present specification, the term "irradiation light" does not refer to light continuously emitted, but is used as a generic term for light (irradiation point) which is irradiated discretely to the observation surface.

Figure 6:
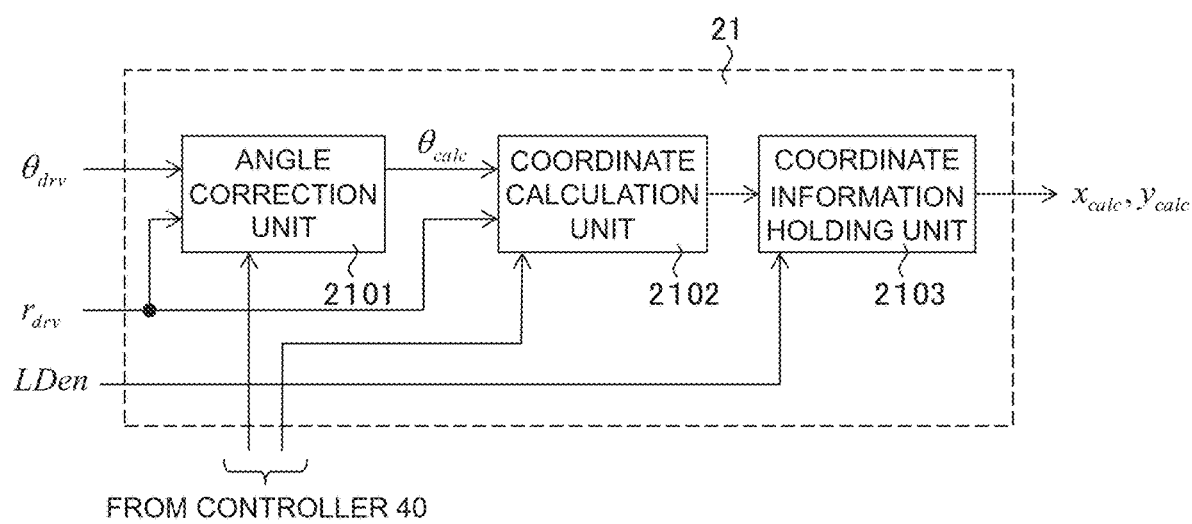
FIG. 6 is a block diagram showing a configuration example of a mapping control unit 21.

Next, FIG. 6 shows a configuration example of the mapping control unit 21. The mapping control unit 21 includes an angle correction unit 2101, a coordinate calculation unit 2102, and a coordinate information holding unit 2103.

The angle correction unit 2101 performs the calculation represented by Mathematical Formula (1) using the angle $\theta_{drv}$ and the radius $r_{drv}$ which are the polar coordinates output from the driving signal generation unit 20, and outputs a correction angle $\theta_{calc}$ obtained as the calculation result to the coordinate calculation unit 2102. The radius $r_{drv}$ is not used in the following Mathematical Formula (1), but is used in Mathematical Formula (27) described later.

[Mathematical Formula 1]

$$\theta_{calc} = \theta_{drv} \quad (1)$$

The coordinate calculation unit 2102 performs calculations represented by Mathematical Formulas (2) and (3), and outputs $x_{calc0}$ and $y_{calc0}$ obtained as the calculation results. Round( ) in the following Mathematical Formulas (2) and (3) represents a function that rounds off variables to output an integer. The same also applies to other Mathematical Formulas that appear later.

[Mathematical Formula 2]

$$x_{calc0} = \text{round}(r_{drv} \cos(\theta_{calc})) \quad (2)$$

[Mathematical Formula 3]

$$y_{calc0} = \text{round}(r_{drv} \sin(\theta_{calc})) \quad (3)$$

It is to be noted that the angle correction unit 2101 and the coordinate calculation unit 2102 may be integrated to perform the calculations of the Mathematical Formulas (1) to (3) collectively.

The coordinate information holding unit 2103 holds the values of $x_{calc0}$ and $y_{calc0}$ as the polar coordinates ($x_{calc}$, $y_{calc}$) in synchronization with the rise (timing from Low to High) of the $LD_{en}$ signal output from the imaging laser emission control unit 23 and outputs the holding polar coordinates ($x_{calc}$, $y_{calc}$) to the later stage under the control of the controller 40.

Next, the relationship between the light emission frequency $f_{dot}$ of the imaging laser and the driving frequency $f_{drv}$ of the vibration unit 101 will be described with reference to FIGS. 7A and 7B.

FIGS. 7A and 7B are diagrams showing simulation results of the positions of the irradiation points irradiated while the spiral trajectory is drawn once. It is to be noted that FIG. 7A shows an example in the case in which the helical pattern is conspicuous, and FIG. 7B shows an example in the case in which the helical pattern is not conspicuous.

The light emission frequency $f_{dot}$ of the imaging laser and the number of turns of the spiral trajectory are common in the cases of FIG. 7A and FIG. 7B, the light emission frequency $f_{dot}$ is 50 kHz, and the number of turns of the spiral trajectory is 250. The driving frequency $f_{drv}$ of the vibration unit 101 is 10.19 kHz in the case of FIG. 7A and 10.24 kHz in the case of FIG. 7B.

In the catheter device 1, the relationship between the light emission frequency $f_{dot}$ of the imaging laser and the driving frequency $f_{drv}$ of the vibration unit 101 is determined so that the following conditions are satisfied. That is, the relationship between the light emission frequency $f_{dot}$ and the driving frequency $f_{drv}$ is determined so that the condition "with respect to any irradiation point P in a region in which the density of the irradiation is relatively low points in the region in which the irradiation light is irradiated, when a distance to an irradiation point A closest to the irradiation point P is defined as a and a distance to an irradiation point B closest to the irradiation point P among the irradiation points existing in a direction not substantially parallel to a line segment PA with the irradiation point P as a base point is defined as b, a and b are substantially equal" is satisfied. This will be described below in detail.

As shown in FIGS. 7A and 7B, in the case of the spiral trajectory, the larger the radius (the farther from the central part), the lower the density of the irradiation points. Therefore, a region in which the density of the irradiation points is lowest is an outermost circumferential side. The irradiation point P in the region in which the density of the irradiation points is relatively low is the irradiation point existing on the outermost circumferential side. For example, the point P1 in FIG. 7A and the point P2 in FIG. 7B correspond thereto. These are not necessarily the irradiation points irradiated at the time of the final turn (in the present case, at the time of 250 turns) when drawing a spiral trajectory.

First, attention is paid to a point P1 existing on the outermost circumference of the irradiation region shown in FIG. 7A. The irradiation point closest to the point P1 is a point A1 in the direction of the curved line forming the helical pattern. In addition, the irradiation point closest to the irradiation point P among the irradiation points in the direction not substantially parallel to the line segment PA with the irradiation point P as the base point is a point B1. Here, for the following description, a substantially parallelogram Sa constituted by four neighboring irradiation points including the points P1, A1, and B1 is considered. In the case of FIG. 7A, among two sides on the outer circumferential side of the substantially parallelogram Sa, a length of a side along the helical pattern is defined as a, and a length of a side substantially orthogonal to the side is defined as b.

Similarly to FIG. 7B, focusing on the point P2 at the outermost circumference of the irradiation region, it is possible to consider a substantially parallelogram Sb. In FIG. 7B, the helical pattern cannot be visually recognized without being conspicuous, and "the direction along the helical pattern" cannot be defined. Therefore, for the sake of convenience of explanation, as shown in FIGS. 7A and 7B, one of the two sides on the outer circumferential side of the substantially parallelogram Sb is defined as a1 and the other is defined as a2.

Since the substantially parallelograms Sa and Sb are not strictly parallelograms, the lengths of the opposite sides are slightly different from each other. However, from the viewpoint of securing the resolution of the catheter device 1, it is preferable to increase the density of the irradiation points, and in practice, this substantially parallelogram can be regarded as a parallelogram.

Therefore, "with respect to any irradiation point P in a region in which the density of the irradiation points is relatively low, when a distance to an irradiation point A closest to the irradiation point P is defined as a and a distance to the irradiation point B closest to the irradiation point P among the irradiation points existing in a direction not substantially parallel to a line segment PA with the irradiation point P as a base point is defined as b, a and b are substantially equal" can be paraphrased as "in the region in which the density of the irradiation points is relatively low, the lengths of the adjacent sides among the lengths of the four sides of the substantially parallelogram constituted by four neighboring points are substantially the same".

In the present specification, "four points" in the expression "substantially parallelogram constituted by four neighboring points" includes three points of any irradiation point P, the irradiation point A closest to the irradiation point P, and the irradiation point B closest to the irradiation point P among the irradiation points existing in the direction not substantially parallel to the line segment PA with the irradiation point P as the base point. In addition, the fourth point is an irradiation point having the shortest distance from a tip position of a synthetic vector of a vector PA and a vector PB with P as the base point when the synthetic vector is considered.

In addition, the "substantially parallelogram constituted by four neighboring points" is the substantially parallelogram constituted by the irradiation point P, the irradiation point A closest to the irradiation point P, and other two irradiation points (defined as the irradiation point B and an irradiation point Q (not shown)) and can be paraphrased as the substantially parallelogram in which the total sum of lengths of four sides becomes smallest. In this case, the irradiation point B is an irradiation point closest to the irradiation point P among the irradiation points existing in the direction not substantially parallel to the line segment PA with the irradiation point P as the base point. In addition, it can be paraphrased as "a quadrilateral shape in which the total sum of the lengths of sides of four sides is the smallest in a microscopic region".

Here, the region in which the density of the irradiation points is relatively low will be described in detail. The "region in which the density of the irradiation points is relatively low" can be paraphrased as the "region in which the area of the substantially parallelogram is largest when the substantially parallelogram constituted by four neighboring irradiation points is considered". In addition, it is preferable that a unit area when the density of the irradiation points is considered is 1 time or more to 9 times or less the area of the substantially parallelogram. Nine times larger than the area of the substantially parallelogram approximately corresponds to a region in which substantially parallelograms are arranged in a 3×3 array.

The present inventors found that the condition in which the helical pattern is conspicuous is the case in which the ratio of the lengths a and b of the sides deviates from 1, and on the contrary, the helical pattern cannot be conspicuous by making the ratio of a and b approximate 1.

It is understood from FIG. 7B that when the lengths a1 and a2 of the sides become substantially equal, that is, when the ratio of a1 and a2 approximates 1, the helical pattern is not conspicuous. Therefore, in the catheter device 1, the relationship between the light emission frequency $f_{dot}$ of the imaging laser and the driving frequency $f_{drv}$ of the vibration unit 101 is determined so that the lengths of adjacent sides among the lengths of four sides of the substantially parallelogram constituted by four neighboring points in the region in which the density of the irradiation points is lowest are substantially equal.

On the other hand, in FIG. 7A, the point A1 having the shortest distance from the focused irradiation point P1 exists in the direction along the helical pattern, but the above-described conditions are not necessarily satisfied. Here, the length of the side along the helical pattern is defined as c, the length of the side substantially orthogonal to the side is defined as d, and the respective calculation methods will be described with reference to the case of FIG. 7A as an example. Hereinafter, the light emission frequency of the laser is represented by $f_{dot}$, the driving frequency of the vibration unit 101 is represented by $f_{drv}$, and the number of turns of the spiral trajectory is represented by $N_{frame}$.

Figure 8A:
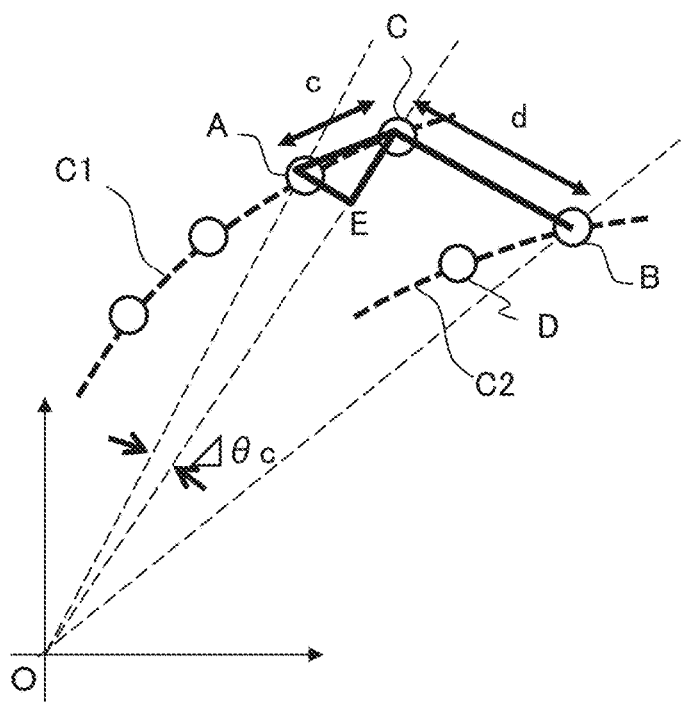
FIGS. 8A and 8B are diagrams for explaining positional relationships of the irradiation points.
Figure 8B:
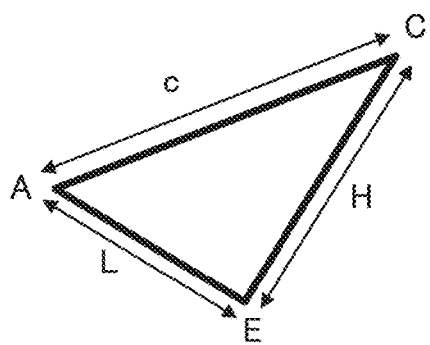

Here, the substantially parallelogram constituted by the irradiation points on the helical pattern will be described. FIGS. 8A and 8B show the substantially parallelograms constituted by the irradiation points on the helical pattern.

In FIG. 8A, curved lines C1 and C2 shown by a broken line indicate adjacent curved lines forming the helical pattern. A point O is the center point of the spiral trajectory and a point C is an irradiation point on an outermost circumference on the curved line C1. A point A is an irradiation point on the curved line C1, which is an irradiation point existing on an inner circumferential side by one point from the point C. In addition, the point B is an irradiation point on the curved line C2, which is an irradiation point whose distance from the point O is substantially equal to that of the point C. That is, OC≈OB is established.

The points A, B, C, and D are four apexes constituting the substantially parallelogram, a length of a side AC which is the side along the helical pattern is defined as c, and a length of the other side BC is defined as d.

First, a ratio α of the light emission frequency $f_{dot}$ and the driving frequency $f_{drv}$ is calculated according to the following Mathematical Formula (4).

[Mathematical Formula 4]

$$\alpha = f_{dot}/f_{drv} = 4.906 \quad (4)$$

The ratio α represents the average number of times that the imaging laser beam is emitted during one rotation of the substantially circular trajectory constituting the spiral trajectory. Here, an integer multiple of the ratio α is considered. An integer value multiplied by the ratio α is defined as N. When α×N is close to an integer value, angles of the respective irradiation points viewed from the point O are similar to each other. In this case, the integer N represents the number of turns until the respective irradiation points are arranged at a similar angle when viewed from the point O.

The present inventors found that N is one tenth of $N_{frame}$ as the condition under which the helical pattern is visually recognized. That is, when a plurality of irradiation points exist at similar angles when viewed from the point O in the range of one tenth of the radius of the irradiation region, the plurality of irradiation points are visually recognized as the helical pattern. For this reason, an upper limit value $N_{max}$ of the integer value N is represented by the following Mathematical Formula (5).

[Mathematical Formula 5]

$$N_{max} = 0.1 N_{frame} = 25 \quad (5)$$

Next, with respect to N=1, 2, . . . , 25 (=$N_{max}$), N where α×N is closest to an integer is defined as $N_p$. Under this condition, $N_p$ is as represented by the following Mathematical Formula (6).

[Mathematical Formula 6]

$$N_p = 11 \quad (6)$$

At this time, α×$N_p$ is as represented by the following Mathematical Formula (7).

[Mathematical Formula 7]

$$\alpha N_p = 53.97 \ldots \approx 54 \quad (7)$$

The above Mathematical Formulas (6) and (7) mean that the irradiation points are arranged at similar angles every 11 periods, and the number of curved lines forming a helix is 54. It can be confirmed that this coincides with the simulation results shown in FIG. 7A.

Here, when α×$N_p$ completely matches the integer value, a curved line forming a helix becomes a straight line. From this, when ∠AOC is $\Delta\theta_c$, $\Delta\theta_c$ is as represented by the following Mathematical Formula (8).

[Mathematical Formula 8]

$$\Delta\theta_c = \frac{2\pi}{\alpha} \cdot (\alpha N_p - \mathrm{round}(\alpha N_p)) \text{ [rad]} \quad (8)$$

As shown in FIG. 8A, an intersection of a perpendicular line down from a point A to a straight line OC with the straight line OC is defined as E, and a right triangle AEC is considered. FIG. 8B is an enlarged view of the right triangle AEC. A length of a side AE is defined as L, and a length of a side CE is defined as H. In addition, with respect to a substantially circular trajectory in a circumference of an outermost of a spiral trajectory, the radius is defined as R. Since the point C is the irradiation point on an outermost circumference on the curved line C1, the lengths L and H of the sides can be calculated using the following Mathematical Formulas (9) and (10).

[Mathematical Formula 9]

$$L = R \cdot \Delta\theta_c \quad (9)$$

[Mathematical Formula 10]

$$H = R \cdot \frac{N_p}{N_{frame}} \quad (10)$$

The length c of the side AC of the right triangle AEC can be calculated using the following Mathematical Formula (11).

[Mathematical Formula 11]

$$c = \sqrt{L^2 + H^2} \quad (11)$$

On the other hand, the length d of the side BC of the substantially parallelogram can be calculated using the following Mathematical Formula (12) since the number of helixes per frame is α×$N_p$.

[Mathematical Formula 12]

$$d = \frac{2\pi R}{\alpha N_p} \quad (12)$$

From the above Mathematical Formulas (11) and (12), a ratio d/c of the lengths of the side BC and the side AC can be calculated by the following Mathematical Formula (13).

[Mathematical Formula 13]

$$d/c = \frac{2\pi}{\alpha N_p \sqrt{\left\{\frac{2\pi}{\alpha} \cdot (\alpha N_p - \mathrm{round}(\alpha N_p))\right\}^2 + \left(\frac{N_p}{N_{frame}}\right)^2}} \quad (13)$$

Since R does not exist in the above Mathematical Formula (13), it is understood that the ratio d/c finally calculated does not depend on the radius R.

When the ratio d/c in the case shown in FIG. 7A is calculated, it is a value of 2 or more as represented by the following Mathematical Formula (14).

[Mathematical Formula 14]

$$d/c = 2.12 \quad (14)$$

On the other hand, when the ratio d/c in the case shown in FIG. 7B is calculated, it is a value approximating 1 as represented by the following Mathematical Formula (15).

[Mathematical Formula 15]

$$d/c = 1.10 \quad (15)$$

Since there are nonlinear calculation elements in the calculation process of $N_p$ or the calculation of the above Mathematical Formula (8), it is not possible to inversely calculate the light emission frequency $f_{dot}$ and the driving frequency $f_{drv}$ from the optimum ratio d/c. On the contrary, if three kinds of values of the light emission frequency $f_{dot}$, the driving frequency $f_{drv}$, and the number $N_{frame}$ of turns of the spiral trajectory are determined, the ratio d/c of the sides can be calculated.

The light emission frequency $f_{dot}$ and the driving frequency $f_{drv}$ in the catheter device 1 are set so that the lengths c and d of the sides obtained by the above-described calculation are substantially equal and the ratio d/c is set to a value approximating 1.

In the above description, the case in which d is larger than c has been described, but c may be larger than d depending on the relationship between the light emission frequency $f_{dot}$ and the driving frequency $f_{drv}$. In consideration of this case, the light emission frequency $f_{dot}$ and the driving frequency $f_{drv}$ may be determined so that the ratio d/c of the sides satisfies the relationship represented by the following Mathematical Formula (16).

[Mathematical Formula 16]

$$0.5 \leq d/c \leq 2 \tag{16}$$

Further, as shown in FIG. 7A, with respect to any irradiation point P in the region in which the density of the irradiation points is lowest, the distance to the irradiation point A closest to the irradiation point P is defined as a, and the distance to the irradiation point B closest to the irradiation point P among the irradiation points existing in the direction not substantially parallel to the line segment PA with the irradiation point P as the base point is defined as b. Hereinafter, the light emission frequency $f_{dot}$ and the driving frequency $f_{drv}$ may be determined so that a ratio b/a of the sides satisfies the relationship represented by the following Mathematical Formula (17).

[Mathematical Formula 17]

$$1 \leq b/a \leq 2 \tag{17}$$

The above Mathematical Formula (17) is a paraphrase expression of the above Mathematical Formula (16). In addition, as shown in FIG. 7B, the above Mathematical Formula (17) is an expression which can be used even in the case in which the helical pattern cannot be visually recognized and the "direction along the helical pattern" cannot be defined.

That is, the above Mathematical Formula (17) can also satisfy the relationship of the above Mathematical Formula (15) corresponding to the case of FIG. 7B.

Figure 30A:
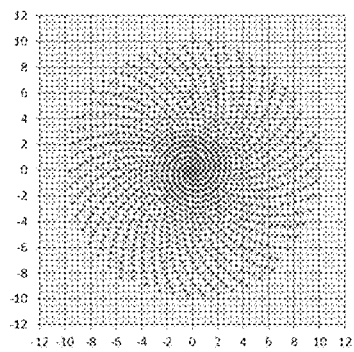
FIGS. 30A to 30C are diagrams showing simulation results of the irradiation points irradiated while a spiral trajectory is drawn once.
Figure 30B:
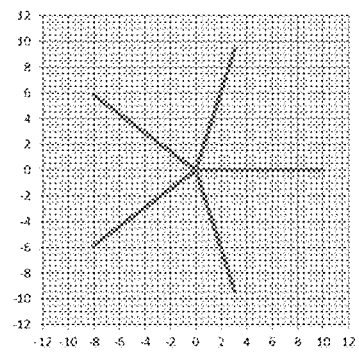

Here, the case in which the irradiation points are arranged in a straight line as shown in FIG. 30B will be described. In the case shown in FIG. 30B, the driving frequency $f_{drv}$ of the vibration unit 101 is 10.0 kHz, the light emission frequency $f_{dot}$ is 50 kHz, and the number of turns of the spiral trajectory is 250.

In the case shown in FIG. 30B, $N_{max}$ which is the upper limit value of N in the calculation of $N_p$ is 25 shown in the above Mathematical Formula (5). However, when the driving frequency $f_{drv}$ is 10.0 kHz, since the ratio α is an integer value 5, α×N is also an integer value. In this way, when a is an integer value, the irradiation points are arranged in a straight line as shown in FIG. 30B. It is determined that the combination of the driving frequency $f_{drv}$, the light emission frequency $f_{dot}$, and the number of turns of the spiral trajectory for obtaining such a result is inappropriate.

Figure 30C:
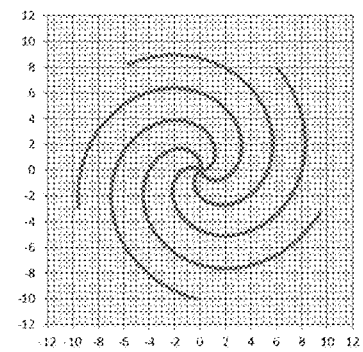

Next, the case in which the number of curved lines forming the helical pattern of the irradiation points is extremely decreased as shown in FIG. 30C will also be described. In the case shown in FIG. 30C, the driving frequency $f_{drv}$ of the vibration unit 101 is 10.03 kHz, the light emission frequency $f_{dot}$ is 50 kHz, and the number of turns of the spiral trajectory is 250.

In the case shown in FIG. 30C, since the ratio α itself is a value very approximating an integer value, even if N is changed in the range from 1 to 25, α×N does not approximate an integer value. Therefore, $N_p$ cannot be obtained. This will be described in detail.

FIGS. 9A to 9F are diagrams for explaining a case in which the number of curved lines forming a helical pattern is extremely small, as shown in FIG. 30C. First, the case of FIG. 7A where $N_p$ can be obtained correctly is considered again. In this case, α×N with respect to N=1, 2, . . . , 25 (=$N_{max}$) is calculated, and $N_p$=11 with N at which α×N is closest to an integer as $N_p$ can be obtained.

Here, α is divided into an integer part and a decimal part, and the decimal part is described mainly. The decimal part of α is represented by β. In the case of FIG. 7A, the ratio α is 4.906 . . . as shown in the above Mathematical Formula (4), so its decimal part β is 0.906 . . . .

Since α=4+β, β×$N_p$ also takes a value approximating an integer when α×$N_p$ takes a value approximating an integer value. The result of calculating β×N with respect to N=1, 2, . . . , 25 (=$N_{max}$) is a graph shown in FIG. 9A, and an abscissa of the graph is N and an ordinate of the graph is β×N. In this graph, it is not possible to simply distinguish in which N the β×N is closest to an integer. Therefore, a function $f_1(N)$ represented by Mathematical Formula (18) and a function $f_2(N)$ represented by the following Mathematical Formula (19) are considered.

[Mathematical Formula 18]

$$f_1(N) = \text{round}(\beta N) - \beta N \tag{18}$$

[Mathematical Formula 19]

$$f_2(N) = |\text{round}(\beta N) - N| \tag{19}$$

The function $f_1(N)$ represents a difference from the nearest integer of β×N. This function is as shown in the graph of FIG. 9B when plotted. On the other hand, the function $f_2(N)$ is obtained by taking an absolute value of the function $f_1(N)$, which is as shown in the graph of FIG. 9C when plotted.

As shown in FIG. 9B, the function $f_1(N)$ is a function having periodicity in the range in which the output is −0.5 or more to 0.5 or less, and N taking a value closest to 0 in a range of a maximum of N=25 is $N_p$. That is, N taking the minimum value of the function $f_2(N)$ shown in FIG. 9C is $N_p$, and $N_p$=11 as is apparent from FIG. 9C.

Next, the case of FIG. 30C is considered. In this case, since the ratio α is 4.985 . . . , the decimal part β thereof is 0.985 . . . .

As in the case of FIG. 7A, the result obtained by calculating β×N is the graph shown in FIG. 9D, the result obtained by plotting the function $f_1(N)$ is the graph shown in FIG. 9E, and the result obtained by plotting the function $f_2(N)$ is the graph shown in FIG. 9F.

In the case of FIG. 30C, as can be seen from FIG. 9E, the function $f_1(N)$ does not have periodicity until N=25 but is monotonically increased. Therefore, the case of N=1 is the closest to 0. That is, α×N with respect to N=1, 2, . . . , 25 (=$N_{max}$) is calculated, and if N closest to an integer is defined as $N_p$, $N_p$ becomes 1. However, this is not the intended calculation result. That is, it is assumed that the calculation "calculating α×N and obtaining N closest to an integer as $N_p$" is a function with periodicity in the range in which the output of the function $f_1(N)$ is −0.5 or more to 0.5 or less.

Therefore, it is determined that the combination of the driving frequency $f_{drv}$, the light emission frequency $f_{dot}$, and the number of turns of the spiral trajectory in which the function $f_1(N)$ is monotonically increased is inappropriate.

The condition for having periodicity without monotonically increasing the function $f_1(N)$ is as represented by the following Mathematical Formula (20).

[Mathematical Formula 20]

$$|\text{round}(\beta) - \beta| \times N_{max} > 1 \quad (20)$$

Here, since $\beta$ is the decimal part of $\alpha$, the above Mathematical Formula (20) can be rewritten using $\alpha$, and if $N_{max}$ is rewritten using the above Mathematical Formula (5), the above Mathematical Formula (20) can be rewritten into the following Mathematical Formula (21).

[Mathematical Formula 21]

$$|\text{round}(\alpha) - \alpha| \times 0.1 N_{frame} \geq 1 \quad (21)$$

Therefore, the light emission frequency $f_{dot}$ and the driving frequency $f_{drv}$ in the catheter device 1 need to satisfy the above Mathematical Formula (21).

It is to noted that the above Mathematical Formula (21) can be used as a common determination condition not only in the case of FIG. 30C but also in the case of FIG. 30B. That is, in the case of FIG. 30B, since a is an integer value, the left side of the above Mathematical Formula (21) becomes 0, and the above Mathematical Formula (21) is not satisfied, which is determined to be inappropriate.

That is, the Mathematical Formulas to be satisfied in the catheter device 1 are, for example, the above Mathematical Formulas (16) and (21). At least one of the light emission frequency $f_{dot}$ and the driving frequency $f_{drv}$ may be adjusted so as to satisfy these conditions.

Next, a light emission cycle $T_{dot}$ ($=1/f_{dot}$) of the laser in the catheter device 1 will be described in detail.

The arrangement of the irradiation points in the catheter device 1 is assumed, for example, as shown in FIG. 7B. In this case, the ratio $\alpha$ of the light emission frequency $f_{dot}$ and the driving frequency $f_{drv}$ is assumed to be as small as about 5. Here, since the ratio $\alpha$ represents the average number of times that a laser emits light during one rotation of the substantially circular trajectory constituting the spiral trajectory, it is understood that any of four irradiation points A, C, B, and D constituting the substantially parallelogram shown in FIG. 8A is not irradiation points irradiated in the same turn. In other words, it can be said that any of the four irradiation points A, C, B, and D constituting the substantially parallelogram is not the irradiation points irradiated continuously.

More specifically, it can be said that the point C and the point B are irradiation points irradiated in with different turns, and the point C and the point A are irradiation points irradiated in different turns. In other words, it can be said that the irradiation point irradiated following the point C is irradiated to the outer side of the substantially parallelogram ACBD. Here, the irradiation point irradiated following the point C means the irradiation point irradiated at the timing when the light emission cycle $T_{dot}$ of the laser has elapsed from the irradiation timing of the point C.

In addition, when with respect to the irradiation point P in the region in which the density of the irradiation points is relatively low, when the distance to the irradiation point A closest to the irradiation point P is defined as a and the distance to the irradiation point B closest to the irradiation point P among the irradiation points existing in the direction not substantially parallel to the line segment PA with the irradiation point P as the base point is defined as b, it can be said that the distance between the irradiation point irradiated following the irradiation point P and the irradiation point P is equal to or more than b.

The "distance between the irradiation point irradiated following the irradiation point P and the irradiation point P is equal to or more than b" can be paraphrased as the case in which the light emission cycle $T_{dot}$ of the imaging laser is longer than a predetermined value. The predetermined value is a value calculated using the driving cycle $T_{drv}$. If the shape of the trajectory of the irradiation light is determined to be a spiral like the catheter device 1, the relational Mathematical Formula using the driving cycle $T_{drv}$ with respect to the light emission cycle $T_{dot}$ can be derived.

Specifically, when the trajectory of the irradiation light is a spiral shape, a length C of an arc connecting the irradiation point irradiated following the irradiation point P and the irradiation point P (none of which is shown) can be calculated using the following Mathematical Formula (22).

[Mathematical Formula 22]

$$C = \frac{2\pi R}{\alpha} = 2\pi R \frac{T_{dot}}{T_{drv}} \quad (22)$$

Since this length C is equal to or longer than the above-mentioned distance b, the light emission cycle $T_{dot}$ satisfies the relationship represented by the following Mathematical Formula (23).

[Mathematical Formula 23]

$$T_{dot} > T_{drv} \cdot \frac{b}{2\pi R} \quad (23)$$

In the derivation process of the above Mathematical Formula (23), it is assumed that the light emission cycle $T_{dot}$ is constant and the laser beam is periodically irradiated. However, also in the case in which the light emission cycle $T_{dot}$ varies, the above Mathematical Formula (23) can be used. In this case, the definition of the light emission cycle $T_{dot}$ may be read as the time from the emission of the laser beam to the next light emission.

In addition, the above Mathematical Formula (23) becomes a conditional Mathematical Formula for which any of the four irradiation points constituting the substantially parallelogram is not the irradiation points continuously irradiated when the trajectory of the irradiation light is the spiral shape.

In the description so far, the ratio $\alpha$ of the light emission frequency $f_{dot}$ and the driving frequency $f_{drv}$ is about 5, but the ratio $\alpha$ may be a value larger than 5. However, as the value of the ratio $\alpha$ is increased, the number of times that a laser emits light is increased during one rotation of the substantially circular trajectory constituting the spiral trajectory, such that the upper limit of the ratio $\alpha$ exists as the precondition that the helical pattern is conspicuous. The present inventors found the following Mathematical Formula (24) as the condition of the ratio $\alpha$ for that purpose.

[Mathematical Formula 24]

$$\alpha = f_{dot}/f_{drv} \leq 50 \quad (24)$$

When the above Mathematical Formula (24) is rewritten using the light emission cycle $T_{dot}$ of the laser beam and the driving cycle $T_{drv}$, it is as represented by the following Mathematical Formula (25).

[Mathematical Formula 25]

$$T_{dot} > \frac{T_{drv}}{50} \quad (25)$$

When the ratio α has a large value but is an integer value, as shown in FIG. 30B, the irradiation points are arranged in a straight line. However, when the ratio α is a large value but is a value slightly deviating from the integer value, the irradiation points are dispersed and the spiral trajectory can be made inconspicuous.

The above Mathematical Formula (25) is the precondition that the helical pattern is conspicuous. Therefore, the above Mathematical Formula (25) can be said to be the precondition that the present invention requires.

Figure 10A:
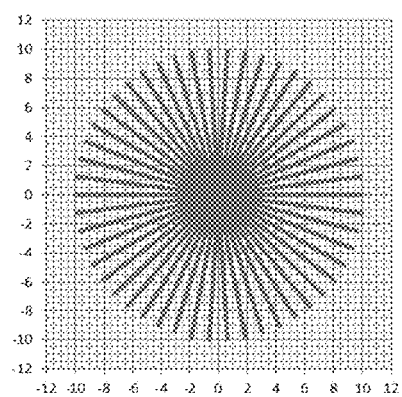
FIGS. 10A to 10C are diagrams showing simulation results of the positions of the irradiation points.
Figure 10B:
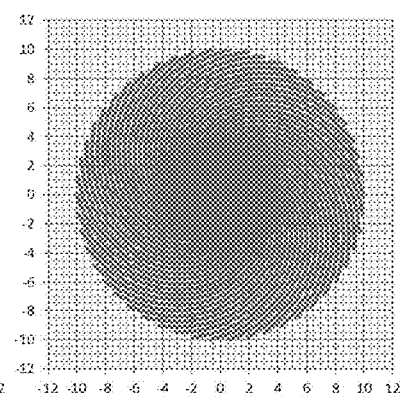
Figure 10C:
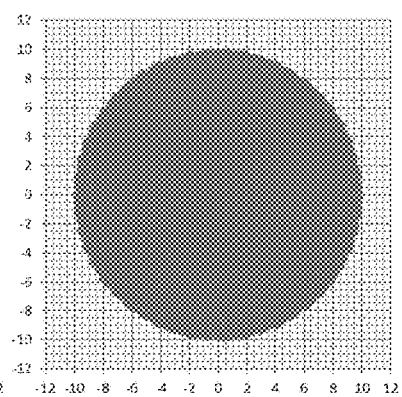

The precondition will be described in detail with reference to FIGS. 10A to 10C. FIGS. 10A to 10C show the simulation results of the positions of the irradiation points when the driving frequency $f_{drv}$ is changed, in the case in which the light emission frequency $f_{dot}$ of the laser beam is 50 kHz and the number of turns of the spiral trajectory is 250.

FIG. 10A shows the case in which the driving frequency $f_{drv}$ is 1.000 kHz, FIG. 10B shows the case in which the driving frequency $f_{drv}$ is 0.998 kHz, and FIG. 10C shows the case in which the driving frequency $f_{drv}$ is 0.996 kHz, respectively. In these cases, the ratio α is about 50.

In FIG. 10A, since the ratio α is an integer value, the irradiation points are arranged in a straight line. On the other hand, in the case of FIG. 10B where the driving frequency $f_{drv}$ differs by only 20 Hz, the number of curved lines forming the helical pattern is increased, and as compared with the case shown in FIG. 7A, the helical pattern is not conspicuous.

In addition, in the case of FIG. 10C where the driving frequency $f_{drv}$ differs by only 40 Hz from the case of FIG. 10A, the helical pattern cannot be visually recognized at all. In this way, when the ratio α is 50 or more, the helical pattern of the irradiation light is not a problem except when the ratio α is an integer value. In other words, it can be said that the precondition that the helical pattern of irradiation light becomes a problem is the case in which the ratio α is 50 or less.

Even in the derivation process of the above Mathematical Formula (25), it is assumed that the light emission cycle $T_{dot}$ is constant and the laser beam is periodically irradiated per certain time. However, also in the case in which the light emission cycle $T_{dot}$ varies, the above Mathematical Formula (25) can be used. In this case, the definition of the light emission cycle $T_{dot}$ may be read as the time from the emission of the laser beam to the next light emission.

Next, an imaging function of the catheter device 1 will be described. First, the photoacoustic imaging method using the photoacoustic phenomenon by the catheter device 1 will be described.

In the catheter device 1, the distance and direction from the object to the photoacoustic element 121 can be calculated based on the photoacoustic signal received by the photoacoustic element 121 of the receiving unit 12.

Figure 11:
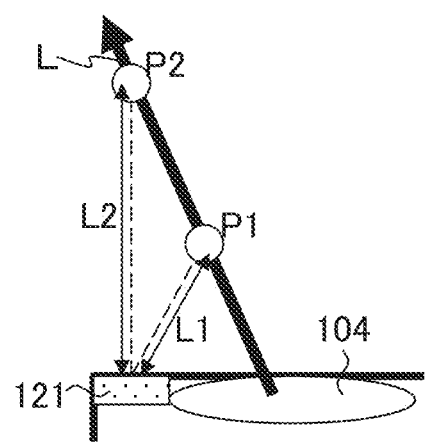
FIG. 11 is a diagram for explaining a method for calculating a distance and a direction of an object.

FIG. 11 is a diagram for explaining a method for calculating the distance and direction from the object to the photoacoustic element 121.

A case in which the imaging laser beam L is emitted in a direction of a thick arrow shown in FIG. 11 is considered. It is assumed that two objects P1 and P2 exist in a traveling direction of the imaging laser. Since an imaging laser beam L travels at a light velocity, the time to reach the object P1 from the emission of the imaging laser beam L and the time to reach the object P2 from the emission of the imaging laser beam L can be neglected. Therefore, a distance $L_1$ between the receiving unit 12 (photoacoustic element 121) and the object P1 and a distance $L_2$ between the receiving unit 12 (photoacoustic element 121) and the object P2 can be represented by the following Mathematical Formulas (26) and (27) using a sound velocity $V_s$.

[Mathematical Formula 26]

$$L_1 = V_s \cdot t_1 \quad (26)$$

[Mathematical Formula 27]

$$L_2 = V_s \cdot t_2 \quad (27)$$

In the above Mathematical Formula (26), $t_1$ is the time from the emission of the imaging laser beam L to the detection of the sound wave by the photoacoustic element 121. In the above Mathematical Formula (27), $t_2$ is the time from the emission of the imaging laser beam L to the detection of the sound wave by the photoacoustic element 121.

It is to be noted that in which direction the detected object P1 or object P2 exists with respect to the photoacoustic element 121 can be easily calculated from the emission direction of the imaging laser beam L, that is, the coordinate information $x_{calc}$ and $y_{calc}$ after the distortion is corrected.

Figure 12:
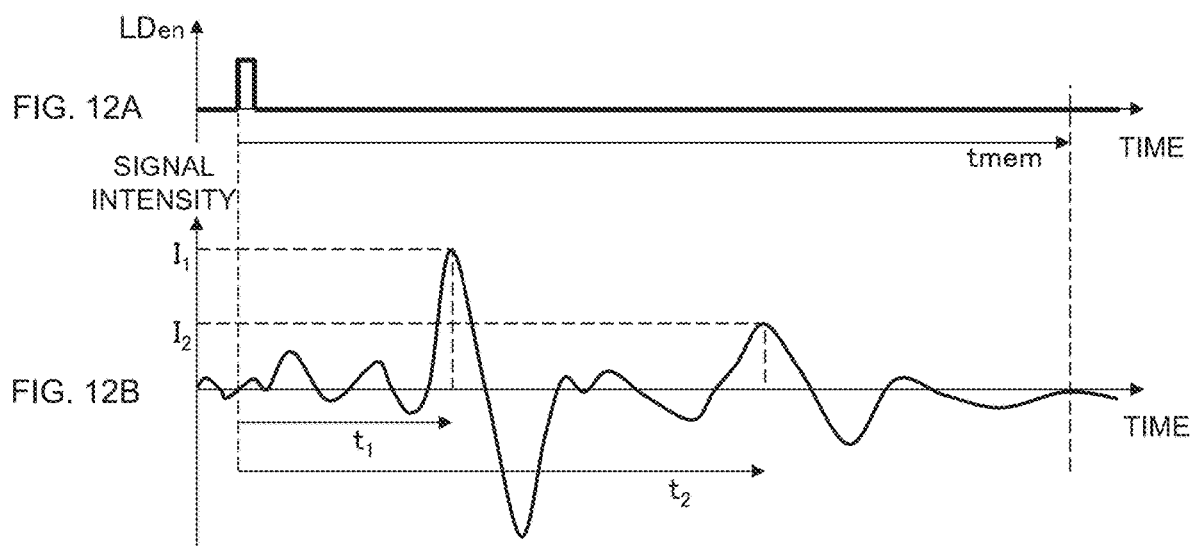
FIGS. 12A and 12B are diagrams for explaining a time change in signal intensity detected by a photoacoustic element 121.

FIGS. 12A and 12B schematically show a time change in signal intensity detected by the photoacoustic element 121 in the positional relationship shown in FIG. 11. A vertical axis of FIG. 12A is a voltage level of the $LD_{en}$ signal, and an ordinate of FIG. 12B is the signal intensity detected by the photoacoustic element 121. In addition, all horizontal axes are time. The times $t_1$ and $t_2$ are as described above, and the timing when the time $t_1$ has elapsed from the rise timing of the $LD_{en}$ signal is referred to as the timing $t_1$. Likewise, the timing when the time $t_2$ has elapsed from the rise timing of the $LD_{en}$ signal is referred to as timing $t_2$.

Signal intensity $I_1$ at the timing $t_1$ is the information on the object P1 in FIG. 11. In addition, signal intensity $I_2$ at the timing $t_2$ is the information on the object P2 in FIG. 11. In this way, information on a plurality of objects can be obtained according to one-time emission of the laser beam. Therefore, if the signal intensity I is stored and analyzed over a predetermined time tmem by emitting light while scanning a laser beam and starting from the rising edge of the $LD_{en}$ signal which is start timing at each emission time, the three-dimensional image can be configured.

Referring back to FIG. 1, in the catheter device 1, an image (hereinafter, referred to as a captured image) is generated based on a sound wave generated in response to the irradiation of the laser beam to the object by the imaging data accumulation control unit 22, the captured image construction unit 43, the imaging data storage memory 33, and the addition frequency storage memory 34.

The information on the captured image finally obtained (information serving as a source of pixel values of the captured image) is stored in the imaging data storage memory 33. Since the vertical and horizontal sizes of the image finally obtained are predetermined values, information on a signal storage period tmem is stored in an address of the imaging data storage memory 33 associated with the coordinates on the image. Hereinafter, data to be stored over the period of the signal storage period tmem is referred to as time-series data.

The captured image construction unit 43 uses the time series data stored in the imaging data storage memory 33 and constructs the three-dimensional image as the catheter captured image based on the calculations shown in the above Mathematical Formulas (26) and (27). It is to be noted that the catheter captured image constructed by the captured image construction unit 43 may be a two-dimensional image or a one-dimensional image.

The imaging data accumulation control unit 22 has a function of integrating the signal intensity of the photoacoustic signal. That is, the imaging data accumulation control unit 22 receives the photoacoustic signal $V_i$ from the receiving unit 12, the coordinates ($x_{calc}$, $y_{calc}$) output from the mapping control unit 21, and the $LD_{en}$ signal output from the imaging laser emission control unit 23. The imaging data accumulation control unit 22 adds the time series data of the photoacoustic signal $V_i$ at every predetermined timing, and stores the addition result in the imaging data storage memory 33 in association with the coordinates ($x_{calc}$, $y_{calc}$). In addition, the imaging data accumulation control unit 22 stores the addition frequency of times in the addition frequency storage memory 34.

Figure 13:
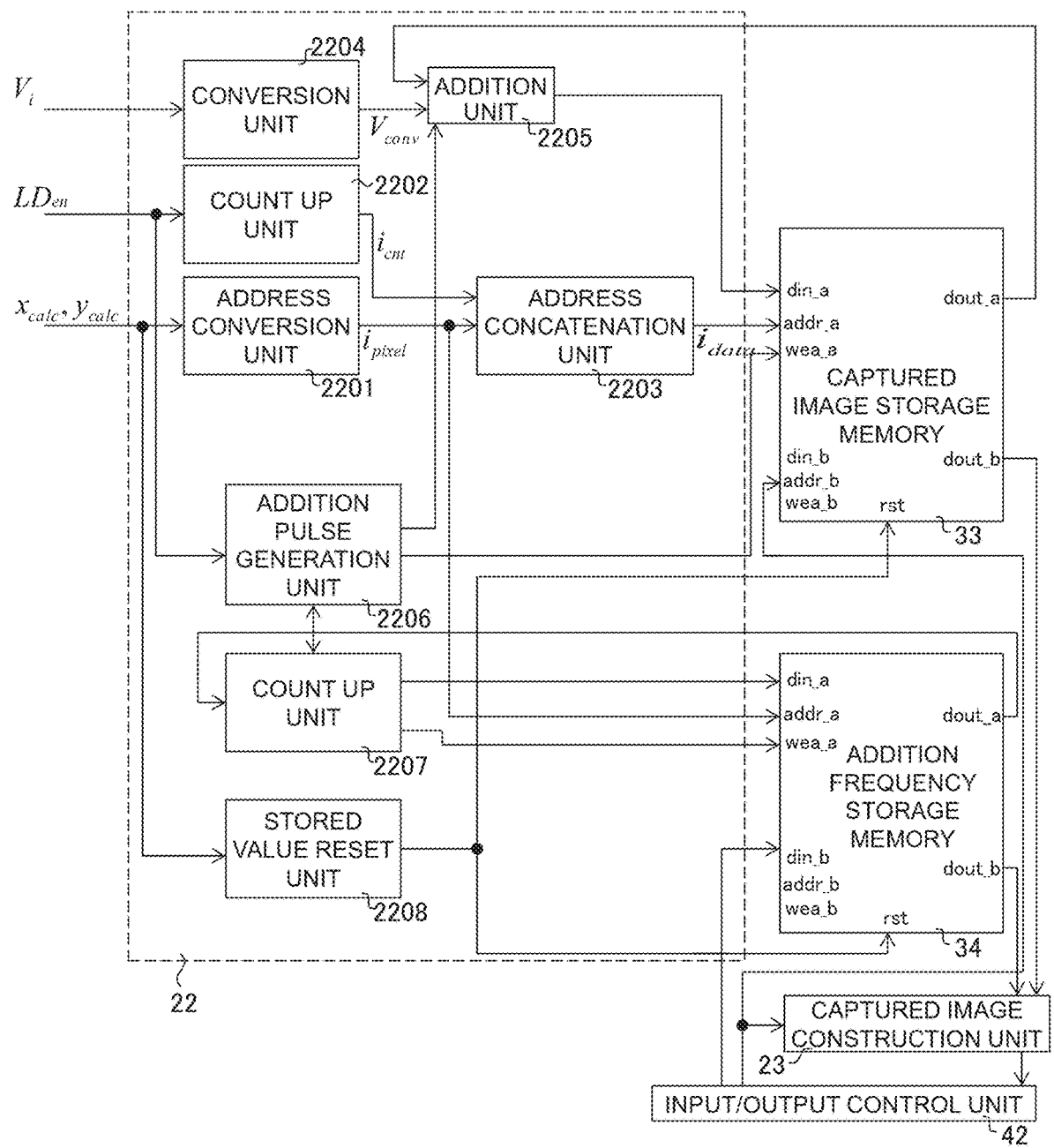
FIG. 13 is a diagram showing a configuration example of an imaging data accumulation control unit 22.

Next, the relationship between the configuration example of the imaging data accumulation control unit 22 and the related block will be described with reference to FIG. 13. FIG. 13 is a block diagram showing the configuration example of the imaging data accumulation control unit 22.

The imaging data accumulation control unit 22 includes an address conversion unit 2201, a count up unit 2202, an address concatenation unit 2203, a conversion unit 2204, an addition unit 2205, an addition pulse generation unit 2206, a count up unit 2207, and a stored value reset unit 2208. The imaging data accumulation control unit 22 is mounted as hardware configured by, for example, an FPGA or the like, and is operated based on a predetermined clock.

The imaging data storage memory 33 and the addition frequency storage memory 34 are constituted by, for example, True Dual Port Ram. The True Dual Port Ram has two completely independent access ports, each of which can be used for read and write operations. In addition, the imaging data storage memory 33 and the addition frequency storage memory 34 have a reset terminal rst and have a function of resetting all stored data to 0 in response to an input to the reset terminal rst.

The address conversion unit 2201 converts the two-dimensional coordinates ($x_{calc}$, $y_{calc}$) output from the mapping control unit 21 into a one-dimensional pixel address $i_{pixel}$ that is an unsigned integer value of M bits. The pixel address $i_{pixel}$ is supplied to address terminals addr_a of port A of the address concatenation unit 2203 and the addition frequency storage memory 34.

The count up unit 2202 resets a count to 0 in synchronization with the rise of the $LD_{en}$ signal from the imaging laser emission control unit 23, and then outputs a value obtained by performing the count up at the same period as a clock converted by the conversion unit 2204 over the signal storage period tmem as a data address $i_{cnt}$ of an unsigned integer value of N bits. Then, the count up unit 2202 stops the count up after the signal storage period tmem has elapsed from the rise of the $LD_{en}$ signal.

The address concatenation unit 2203 generates a concatenation address $i_{data}$ of (M+N) bits by setting a pixel address $i_{pixel}$ converted by the address conversion unit 2201 as an upper level, setting a data address $i_{cnt}$ output from the count up unit 2202 as a lower level, and concatenating between the pixel address $i_{pixel}$ and the data address $i_{cnt}$. The generated concatenation address $i_{data}$ is input to the address terminals addr_a of the port A of the imaging data storage memory 33, and becomes the address information at the time of storing the time series data of the photoacoustic signal by associating the time series data with the coordinates ($x_{calc}$, $y_{calc}$).

The conversion unit 2204 A/D converts the photoacoustic signal value $V_i$ as an analog signal input from the receiving unit 12 into a conversion value $V_{conv}$ as a digital signal which is stored in the imaging data storage memory 33, and outputs the converted value to the addition unit 2205.

The addition unit 2205 adds data read from a data output terminal dout_a of the port A of the imaging data storage memory 33 to the conversion value $V_{conv}$ from the conversion unit 2204 and outputs the added data to a data input terminal din_a of the port A of the imaging data storage memory 33. It is to be noted that the addition timing of the addition unit 2205 is controlled by a pulse from the addition pulse generation unit 2206.

The addition pulse generation unit 2206 receives the $LD_{en}$ signal from the imaging laser emission control unit 23 as an input, and outputs the pulse of the same period as the clock converted by the conversion unit 2204 to the addition unit 2205 for a period from the rise of the $LD_{en}$ signal to the lapse of the signal storage period tmem. In addition, the addition pulse generation unit 2206 outputs a predetermined instruction even to the count up unit 2207 every time the pulse is output to the addition unit 2205. In addition, the addition pulse generation unit 2206 generates a signal to be input to the write enable terminal wea_a of the port A of the imaging data storage memory 33. This signal is a signal that is shifted to High only for one clock after the addition in the addition unit 2205 ends and then returned to Low.

By the above configuration, the value obtained by adding the conversion value $V_{conv}$ to the data read from the read terminal dout_a of the port A of the imaging data storage memory 33 by the addition unit 2205 is again stored in the imaging data storage memory 33.

It is to be noted that the addition pulse generation unit 2206 may be configured to receive an instruction to stop an addition from the outside.

The count up unit 2207 adds 1 to the data read from the data output terminal dout_a of the port A of the addition frequency storage memory 34 according to the instruction from the addition pulse generation unit 2206. As a result, the number of times that the addition unit 2205 executes an addition is counted for the period in which the coordinates output from the mapping control unit 21 are $x_{calc}$ and $y_{calc}$. The counted result is output to the data input terminal din_a of the addition frequency storage memory 34.

In addition, the count up unit 2207 generates a signal that is shifted to High only for one clock after the count up ends and then returned to Low according to an instruction from the addition pulse generation unit 2206, and outputs the generated signal to the write enable terminal wea_a of the port A of the addition frequency storage memory 34.

It is to be noted that a function of notifying another block of the fact that the number of times to execute the count up has reached the predetermined number of times may be added to the count up unit 2207.

By allowing the addition pulse generation unit 2206 to repeat the above operation, the addition unit 2205 sequentially adds the conversion value $V_{conv}$ obtained by converting each of the time series data for the period in which the coordinates output from the mapping control unit 21 are $x_{calc}$ and $y_{calc}$. In other words, as the addition result, the integrated value of the time series data is stored in the corresponding address in the imaging data storage memory 33. In addition, the number of times that the addition unit 2205 performs an addition for the period in which the coordinates output from the mapping control unit 21 are $x_{calc}$ and $y_{calc}$ is stored in the corresponding address in the addition frequency storage memory 34.

When the coordinates ($x_{calc}$, $y_{calc}$) output from the mapping control unit 21 coincide with the predetermined coordinates, the stored value reset unit 2208 outputs a reset signal for resetting the values stored in the imaging data storage memory 33 and the addition frequency storage memory 34. The reset signal is supplied to the rst terminals of the imaging data storage memory 33 and the addition frequency storage memory 34, respectively.

As a result, the imaging data storage memory 33 stores results obtained by allowing the addition unit 2205 to sequentially add the conversion value $V_{conv}$ obtained by converting each of the time series data for the period in which the coordinates output from the mapping control unit 21 are ($x_{calc}$, $y_{calc}$) during one frame (that is, a period in which the spiral trajectory is drawn once). In addition, the addition frequency storage memory 34 stores the number of times that the additions are executed for the period in which the coordinates output from the mapping control unit 21 are ($x_{calc}$, $y_{calc}$) during one frame.

A signal from the input/output control unit 42 is supplied to address terminals addr_b of port B of the imaging data storage memory 33 and the addition frequency storage memory 34. The data output terminals dout_b of the port B of the imaging data storage memory 33 and the addition frequency storage memory 34 are connected to the captured image construction unit 43.

The input/output control unit 42 supplies the address corresponding to the concatenation address $i_{data}$ to the address terminal addr_b of the port B of the imaging data storage memory 33 and the captured image construction unit 43. In addition, the input/output control unit 42 supplies the address corresponding to the pixel address $i_{pixel}$ to the address terminal addr_b of the port B of the addition frequency storage memory 34.

Since the value obtained by adding the time series data over the period of the signal storage period tmem plural times is stored in the imaging data storage memory 33, the addition frequency is acquired from the corresponding address of the addition frequency storage memory 34, and the time series data can be averaged by dividing the value read from the imaging data storage memory 33 by the addition frequency. The calculation of the averaging is executed by the captured image construction unit 43. The captured image construction unit 43 constitutes a three-dimensional image, and outputs image information to the external control device 50 via the input/output control unit 42. As a result, the external control device 50 can acquire the three-dimensional image as the catheter captured image output from the captured image construction unit 43.

Figure 14:
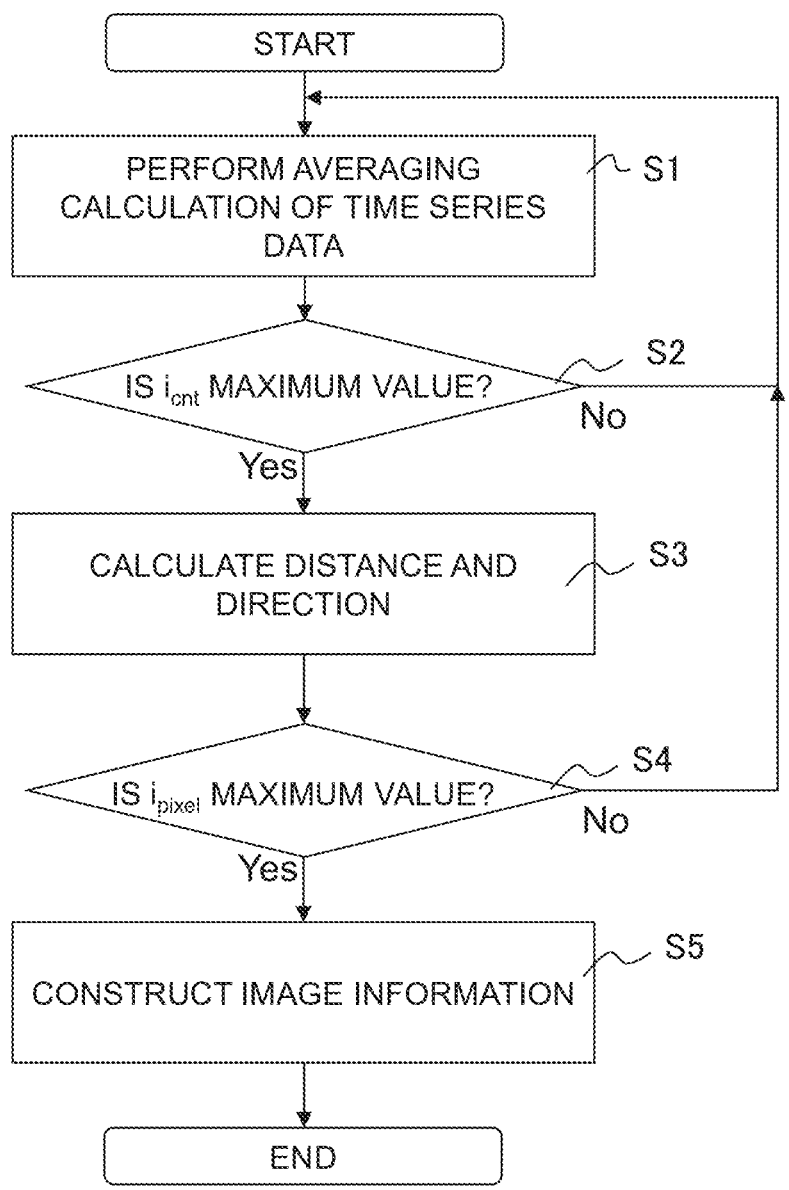
FIG. 14 is a flowchart showing an example of three-dimensional image construction processing by a captured image construction unit 43.

Next, FIG. 14 is a flowchart for describing an example of the three-dimensional image construction processing by the captured image construction unit 43.

The three-dimensional image construction processing is started when the address corresponding to the concatenation address $i_{data}$ is supplied from the input/output control unit 42 to the captured image construction unit 43.

First, the captured image construction unit 43 reads the addition value of the time series data stored in the imaging data storage memory 33, and performs the averaging calculation of the time series data by dividing the read calculation value by the addition frequency read from the addition frequency storage memory 34 (step S1).

Subsequently, the captured image construction unit 43 determines whether the lower N bit $i_{cnt}$ of the concatenation address $i_{data}$ is a maximum value (step S2). The fact that the lower N bit $i_{cnt}$ is the maximum value means that data are input from the imaging data storage memory 33 to a final value of the signal storage period tmem of the time series data, and when the lower N bit $i_{cnt}$ is the maximum value, the averaged time series data are aligned over the signal storage period tmem.

If it is determined in step S2 that the lower N bit $i_{cnt}$ is not the maximum value (No in step S2), since the lower N bit $i_{cnt}$ is in the signal storage period tmem of the time series data, the captured image construction unit 43 returns the processing to step S1 and repeats processing thereafter. Thereafter, if it is determined that the lower N bit $i_{cnt}$ is the maximum value (Yes in step S2), the captured image construction unit 43 progresses the processing to step S3, and calculates the distance and direction from the object to the photoacoustic element 121.

Subsequently, the captured image construction unit 43 determines whether the upper M bit $i_{pixel}$ of the concatenation address $i_{data}$ is a maximum value (step S4). If it is determined that the upper M bit $i_{pixel}$ is not the maximum value (No in step S4), the captured image construction unit 43 returns the processing to step S1 and repeats processing thereafter. If it is determined that the upper M bit $i_{pixel}$ is the maximum value (Yes in step S4), the captured image construction unit 43 progresses the processing to step S5. In this step, as the processing of steps S1 to S4 are repeated, as shown in FIG. 11, the calculation of the distance and direction when the imaging laser beam L face in a certain direction is performed.

Next, the captured image construction unit 43 constructs and outputs the three-dimensional image finally output (step S5). As described above, the three-dimensional image construction processing by the captured image construction unit 43 ends.

In the above description, the averaging calculation of the time series data is performed by the captured image construction unit 43 included in the catheter device 1, but the calculation may also be performed outside the catheter device 1.

Figure 15:
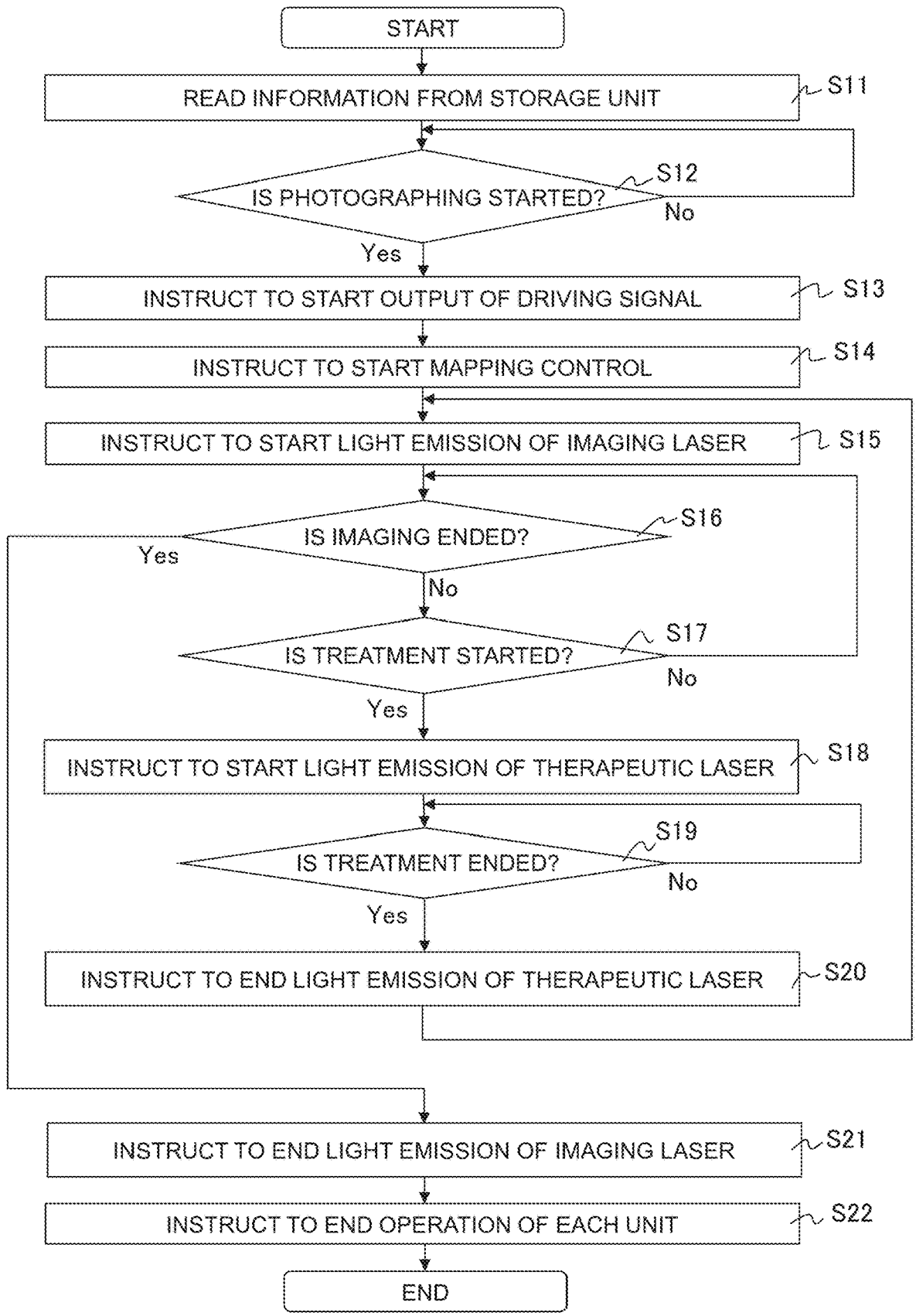
FIG. 15 is a flowchart showing an example of control processing by a controller 40 of the catheter device 1.

Next, FIG. 15 is a flowchart showing an example of the control processing by the controller 40 of the catheter device 1.

The control processing starts in response to a predetermined operation (for example, an operation of turning on a main power supply) from a user.

First, the controller 40 reads information necessary for controlling each component of the catheter device 1 from the storage unit 41 (step S11). Here, the read information includes, for example, the magnification in the first variable gain unit 2005, the magnification in the second variable gain unit 2006, the phase difference in the second sine wave generation unit 2003, and the like.

Next, the controller 40 determines whether there is an instruction to start imaging from the external control device 50 through the input/output control unit 42 (step S12). If it is determined that there is no instruction to start the imaging (No in step S12), the controller 40 waits until an instruction to start the imaging is received. Thereafter, if it is determined that there is an instruction to start the imaging (Yes in step S12), the controller 40 controls the driving signal generation unit 20 to start outputting the driving signal (step S13). Specifically, the controller 40 sets the magnification in the first variable gain unit 2005 of the driving signal generation unit 20 and the magnification in the second variable gain unit 2006 to be values other than 0 in accordance with the information read from the storage unit 41 in step S11 to start outputting the driving signal. As a result, the catheter device 1 enters the imaging mode.

Next, the controller 40 controls the mapping control unit 21 to start the mapping control (step S14). Specifically, the controller 40 supplies the information on the function used for the calculation in the mapping control unit 21 to start the mapping control. At the same time, the imaging data accumulation control unit 22 also starts the processing of storing the output signal of the receiving unit 12 as the time series data in the imaging data storage memory 33.

Next, the controller 40 controls the imaging laser emission control unit 23 to start the light emission control of the imaging laser (step S15). By the processing up to step S15, the photoacoustic imaging by the catheter device 1 starts.

Next, the controller 40 determines whether there is an instruction to end imaging from the external control device 50 through the input/output control unit 42 (step S16). If it is determined that there is no instruction to end the imaging (No in step S16), the controller 40 determines whether there is an instruction to start treatment from the external control device 50 through the input/output control unit 42 (step S17). If it is determined that there is no instruction to start the treatment (No in step S17), the controller 40 returns the processing to step S16 and repeats the processing thereafter.

If it is determined that there is an instruction to start treatment (Yes in step S17), the controller 40 controls the therapeutic laser emission control unit 24 to start the light emission control of the therapeutic laser (step S18). As a result, the catheter device 1 enters a treatment mode, and starts treatment using the therapeutic laser. Specifically, by irradiating the therapeutic laser to the target coordinates received from the input/output control unit 42, treatment such as burning off a cell tissue by irradiating the treatment laser to the lesion site is performed.

Next, the controller 40 determines whether there is an instruction to end the treatment from the external control device 50 through the input/output control unit 42 (step S19), and waits until there is the instruction to end treatment (No in step S19). If it is determined that there is an instruction to end the treatment (Yes in step S19), the controller 40 controls the therapeutic laser emission control unit 24 to end the light emission of the therapeutic laser (step S20). Thereafter, the controller 40 returns the processing to step S15, and repeats the processing thereafter. As a result, the catheter device 1 ends the treatment mode and returns to the imaging mode.

Thereafter, if it is determined that there is an instruction to end the treatment (Yes in step S16), the controller 40 controls the imaging laser emission control unit 23 to end the emission of the imaging laser (step S21). Thereafter, the controller 40 ends the operation of each component (for example, the driving signal generation unit 20, the mapping control unit 21, or the like) of the catheter device 1 (step S22). Hereinabove, the description of the control processing by the controller 40 ends.

<Effect of Catheter Device 1 According to First Embodiment>

Next, the effect by the catheter device 1 will be described.

As a first effect, it can be mentioned that when the imaging laser is irradiated in the spiral shape, the helical pattern can be made inconspicuous by dispersing the irradiation points substantially equally. Specifically, among the lengths of four sides of the substantially parallelogram constituted by the four neighboring points on the outermost circumference of the region in which the irradiation light is irradiated, the lengths of the adjacent sides are substantially equal, such that for example, in the case of FIG. 7B, the helical pattern cannot be inconspicuous as compared with the case shown in FIG. 7A.

For example, in the case of FIG. 8, the length d of the side is about twice the length c of the side. The present inventors found that the irradiation points appear to be continuous in the direction of the length c of the side when the lengths of the sides are different twice or more, and become the helical pattern as a whole to be visually recognized. Therefore, the relationship between the light emission frequency $f_{dot}$ and the driving frequency $f_{drv}$ is determined so that the ratio d/c of the lengths of the sides satisfies the above Mathematical Formula (16). Alternatively, the relationship between the light emission frequency $f_{dot}$ and the driving frequency $f_{drv}$ is determined so that the ratio b/a of the lengths of the sides of the substantially parallelogram shown in FIG. 7A satisfies the above Mathematical Formula (17).

It is to be noted that any of the four neighboring irradiation points constituting the substantially parallelogram is not the irradiation points continuously irradiated.

For example, in the catheter device 1, the ratio α of the light emission frequency $f_{dot}$ and the driving frequency $f_{drv}$ is about 4.9. Therefore, about five irradiation points are irradiated in a first turn, and these irradiation points form a pentagon. In a second turn, five irradiation points are irradiated again at a position where the pentagon has slightly rotated, and in a third turn, five irradiation points are irradiated at a position where the pentagon is further slightly rotated. If the pentagon is repeatedly drawn by going through the turns as described above, five irradiation points forming the pentagon in eleven turns and five irradiation points forming the pentagon in the first turn have a substantially equal angle from the center. This is a mechanism in which the irradiation points appear as the spiral pattern. As a result, all the four neighboring irradiation points, which are not irradiation points continuously irradiated, constitute the substantially parallelogram.

Therefore, the first effect is that, in the precondition that any of the four neighboring irradiation points is not the irradiation point continuously irradiated, among the lengths of four sides of the substantially parallelogram constituted by the four neighboring points on the outermost circumference of the region in which the irradiation light is irradiated, the lengths of the adjacent sides are substantially equal, such that the irradiation point is irradiated to an appropriate position, thereby removing the helical pattern.

As the second effect, it is possible to improve the S/N of the captured image.

The imaging data accumulation control unit 22 has a function of integrating information on the signal intensity of the photoacoustic signal by the addition unit 2205. In addition, it is possible to remove the helical pattern without thinning out the emission of the imaging laser, by considering the substantially parallelogram mentioned above in the region with the lowest density.

For example, as can be seen from FIG. 7B, the helical pattern cannot be visually recognized on the outermost circumference, but the helical pattern can be confirmed in the central part of the spiral trajectory. However, since the density of the irradiation points is high in the central part, this is not a problem. The reason is that normally the captured image captured by the catheter device 1 is allocated to a squared pixel and displayed. A pitch of a pixel of the captured image is set based on the distance between the irradiation points on the outermost circumference where the density of the irradiation points is the lowest. For example, the pitch of the pixel of the captured image may be the same as the average distance of the irradiation points on the outermost circumference.

As a result, the helical pattern in the central part of the spiral trajectory falls within one pixel, and thus does not appear as the helical pattern in the captured image. From this, it can be seen that the substantially parallelogram needs to be considered in the region in which the density of the irradiation points is lowest. Since the helical pattern at the central part has many irradiation points within one pixel, if the information on a large number of irradiation points is averaged, the S/N can be improved.

Figure 16:
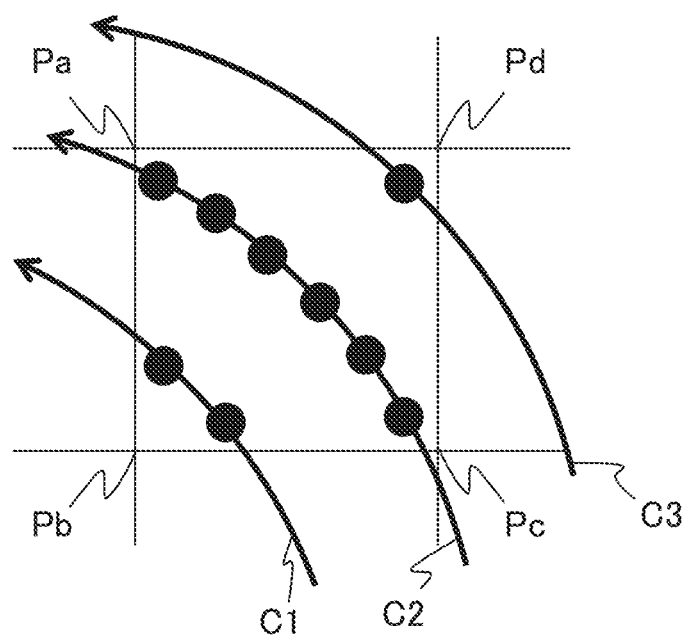
FIG. 16 is a diagram for explaining an improvement effect in S/N.

The effect of the S/N improvement will be described with reference to FIG. 16. FIG. 16 shows the relationship between the trajectory of light on the projection plane (observation surface) of the irradiation light and the region on the projection plane corresponding to one pixel of the captured image.

The square formed by the intersections Pa, Pb, Pc and Pd of the lattices in FIG. 16 indicates a region on the projection plane corresponding to one pixel of the captured image. The trajectories C1, C2, and C3 are a part of the trajectory of the irradiation light, and are turns adjacent to each other. The trajectory of the next turn of the trajectory C1 is C2 and the next trajectory of the trajectory C2 is C3. In addition, a black circle on the trajectory indicates the irradiation point generated on the projection plane by allowing the imaging laser emission control unit 23 to perform the emission of the imaging laser. In the case of FIG. 16, there are nine irradiation points in the region corresponding to one pixel of the captured image.

In the catheter device 1, the conversion values $V_{conv}$ of the photoacoustic signals $V_i$ corresponding to nine irradiation points shown in FIG. 16, respectively, are sequentially added and averaged, such that the emission of the imaging laser is not thinned out, thereby improving the S/N in the captured image while maintaining the light emission frequency $f_{dot}$. Therefore, when the captured image is displayed, its image quality can be improved, and in the case of measuring the three-dimensional shape in the blood vessel based on the captured image, the measurement accuracy can be improved.

In addition, as a third effect, it is possible to use a pulsed laser having strong power as the imaging laser. Generally, when the power of the laser is increased, the light emission frequency of the laser is decreased, and a laser having a low light emission frequency is difficult to avoid generating the helical pattern. However, in the catheter device 1, the irradiation point can be irradiated to an appropriate position even if the imaging laser has strong power and a low light emission frequency. By using an imaging laser with strong power, the photoacoustic phenomenon can be strengthened, and the intensity of the received sound wave can be increased. As a result, it is possible to contribute to the S/N of the captured image. Alternatively, the distance to the observable object can be extended.

<As to Distance Measuring Device 2 According to Second Embodiment of the Present Invention>

The catheter device 1 (FIG. 1) according to the first embodiment of the present invention is a kind of imaging device for obtaining a captured image by the photoacoustic imaging method.

A distance measuring device 2 according to a second embodiment of the present invention described below is a type of imaging device that measures a distance to an object by a time of flight (TOF) method to obtain a distance image.

Figure 17:
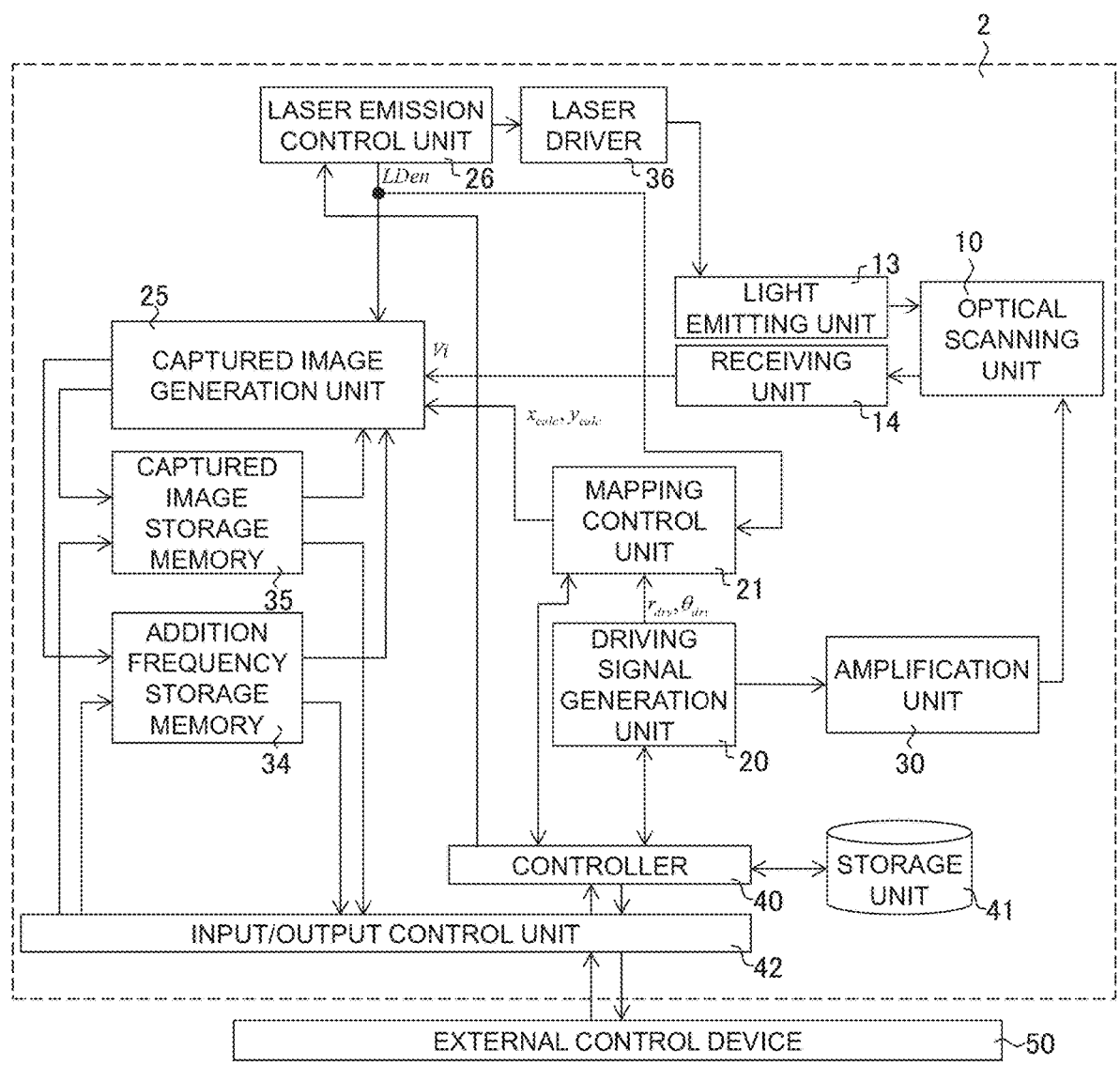
FIG. 17 is a block diagram showing a configuration example of a distance measuring device 2 according to a second embodiment.

FIG. 17 is a block diagram showing a configuration example of the distance measuring device 2 according to the second embodiment of the present invention.

Of components of the distance measuring device 2, the same components as those of the catheter device 1 are denoted by the same reference numerals and a description thereof will be omitted.

The distance measuring device 2 has a configuration in which the light emitting unit 11 and the receiving unit 12 of the catheter device 1 are replaced with a light emitting unit 13 and a receiving unit 14 and the imaging laser emission control unit 23, the therapeutic laser emission control unit 24, the imaging laser driver 31, and the therapeutic laser driver 32 of the catheter device 1 are replaced with a laser emission control unit 26 and a laser driver 36.

The distance measuring device 2 has a configuration in which the imaging data accumulation control unit 22 and the imaging data storage memory 33 of the catheter device 1 are replaced with a captured image generation unit 25 and a captured image storage memory 35, the captured image construction unit 43 of the catheter device 1 is omitted, and various signals input to the captured image construction unit 43 are input to an input/output control unit 42.

The receiving unit 14 in the distance measuring device 2 receives a return light, and generates information $V_i$ according to the return light and outputs the generated information to the captured image generation unit 25. Here, the return light indicates reflected light which returns to an optical scanning unit 10 after light irradiated from the light emitting unit 13 is reflected from an object.

Next, a configuration example of the optical scanning unit 10, the light emitting unit 13, and the receiving unit 14 in the distance measuring device 2 will be described with reference to FIGS. 18 and 19.

Figure 18:
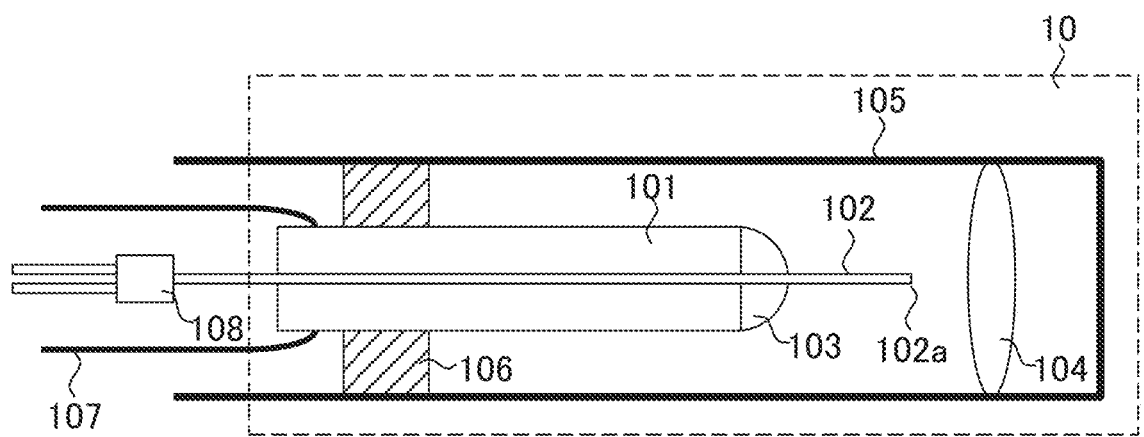
FIG. 18 is a diagram showing an example of a cross section of an optical scanning unit 10 of FIG. 17.

FIG. 18 is a cross-sectional view showing the configuration example of the optical scanning unit 10 in the distance measuring device 2. The optical scanning unit 10 in the distance measuring device 2 is configured by adding a demultiplexing unit 108 to the configuration of the optical scanning unit 10 (FIG. 2A) in the catheter device 1. The demultiplexing unit 108 is provided at an end opposite to a light emitting end 102a of a light guide path 102. However, the optical scanning unit 10 in the catheter device 1 is formed integrally with the receiving unit 12, whereas the fact that the optical scanning unit 10 of the distance measuring device 2 is not formed integrally with the receiving unit 14 is different from the catheter device 1.

Figure 19:
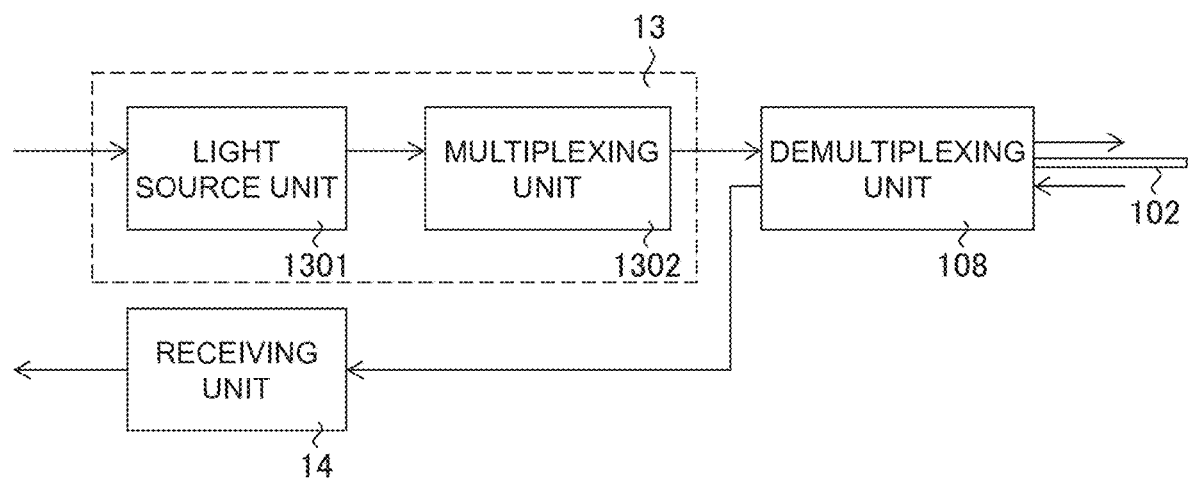
FIG. 19 is a diagram showing a relationship between a light emitting unit 13, a receiving unit 14, and a demultiplexing unit 108 in the distance measuring device 2.

FIG. 19 is a diagram showing the relationship between the light emitting unit 13, the receiving unit 14, and the demultiplexing unit 108 of the optical scanning unit 10.

The light emitting unit 13 includes a light source unit 1301 and a multiplexing unit 1302. The light source unit 1301 includes one or more laser light sources. The multiplexing unit 1302 multiplexes lights emitted from one or more laser light sources configuring the light source unit 1301. For example, the light source unit 1301 includes laser light sources corresponding to each color of R, G, and B which are three primary colors of light, and the multiplexing unit 1302 can synthesize light of any color based on lights of these three colors. In the distance measuring device 2, however, it is assumed that only one laser beam of R, G, and B is emitted. The multiplexed light is guided to the demultiplexing unit 108 of the optical scanning unit 10 through an optical fiber (not shown).

The demultiplexing unit 108 guides light output from the light emitting unit 13 to the light guide path 102, such that the light is emitted from the light emitting end 102a of the light guide path 102. In addition, the demultiplexing unit 108 guides the return light from the object taken into the light guide path 102 to the receiving unit 14.

The receiving unit 14 includes, for example, a color filter, a lens, and a detector, and outputs information corresponding to the intensity of the return light guided by the demultiplexing unit 108.

Return to FIG. 17. Under the control of the controller 40, the laser emission control unit 26 outputs a light emission control signal for controlling the emission of the respective laser light sources configuring the light source unit 1301 of the light emitting unit 13. The light emission control signal is supplied to each laser light source configuring the light source unit 1301 of the light emitting unit 13 via the laser driver 36.

The laser emission control unit 26 generates a light emission control signal so that the light emission by the light emitting unit 13 repeats at a predetermined light emission frequency $f_{dot}$ (for example, 50 kHz). In addition, the laser emission control unit 26 generates an $LD_{en}$ signal that becomes High at timing at which the laser light source emits light, and supplies the generated $LD_{en}$ signal to the captured image generation unit 25 and the mapping control unit 21. It is to be noted that the laser emission control unit 26 may be configured to set a predetermined time delay with respect to the timing at which the laser light source emits light under the control of the controller 40.

Even in the distance measuring device 2, the relationship between the light emission frequency $f_{dot}$ of the laser beam and the driving frequency $f_{drv}$ of the vibration unit 101 is determined so as to satisfy the same relationship as the case of the catheter device 1.

That is, the light emission frequency $f_{dot}$ and the driving frequency $f_{drv}$ are determined so that among lengths of four sides of a substantially parallelogram constituted by four neighboring points on an outermost circumference of an irradiation region of the irradiation light, lengths of adjacent sides are substantially equal.

The captured image generation unit 25, the captured image storage memory 35, and the addition frequency storage memory 34 calculate a distance between an object and the receiving unit 14 based on a time until the laser beam scanned by the optical scanning unit 10 impinges on the object and returns to generate a distance image having the calculated distance as a pixel value.

The information on the distance image finally obtained (information serving as a source of pixel values of the captured image) is stored in the captured image storage memory 35. Since vertical and horizontal sizes of the distance image finally obtained are predetermined values, the information is stored in an address of the captured image storage memory 35 associated with coordinates on the image.

The captured image generation unit 25 has a function of measuring the distance between the object and the receiving unit 14 and a function of integrating the measured distance. Specifically, the captured image generation unit 25 acquires the information $V_i$ associated with the return light from the object from the receiving unit 14, and generates the distance information based on the acquired information $V_i$. In addition, the captured image generation unit 25 receives coordinates ($x_{calc}$, $y_{calc}$) output from the mapping control unit 21, adds the distance information at every predetermined timing, and stores the added result in the captured image storage memory 35 by associating the added result with the coordinates ($x_{calc}$, $y_{calc}$). In addition, the captured image generation unit 25 stores an addition frequency of the distance information in the addition frequency storage memory 34.

Figure 20:
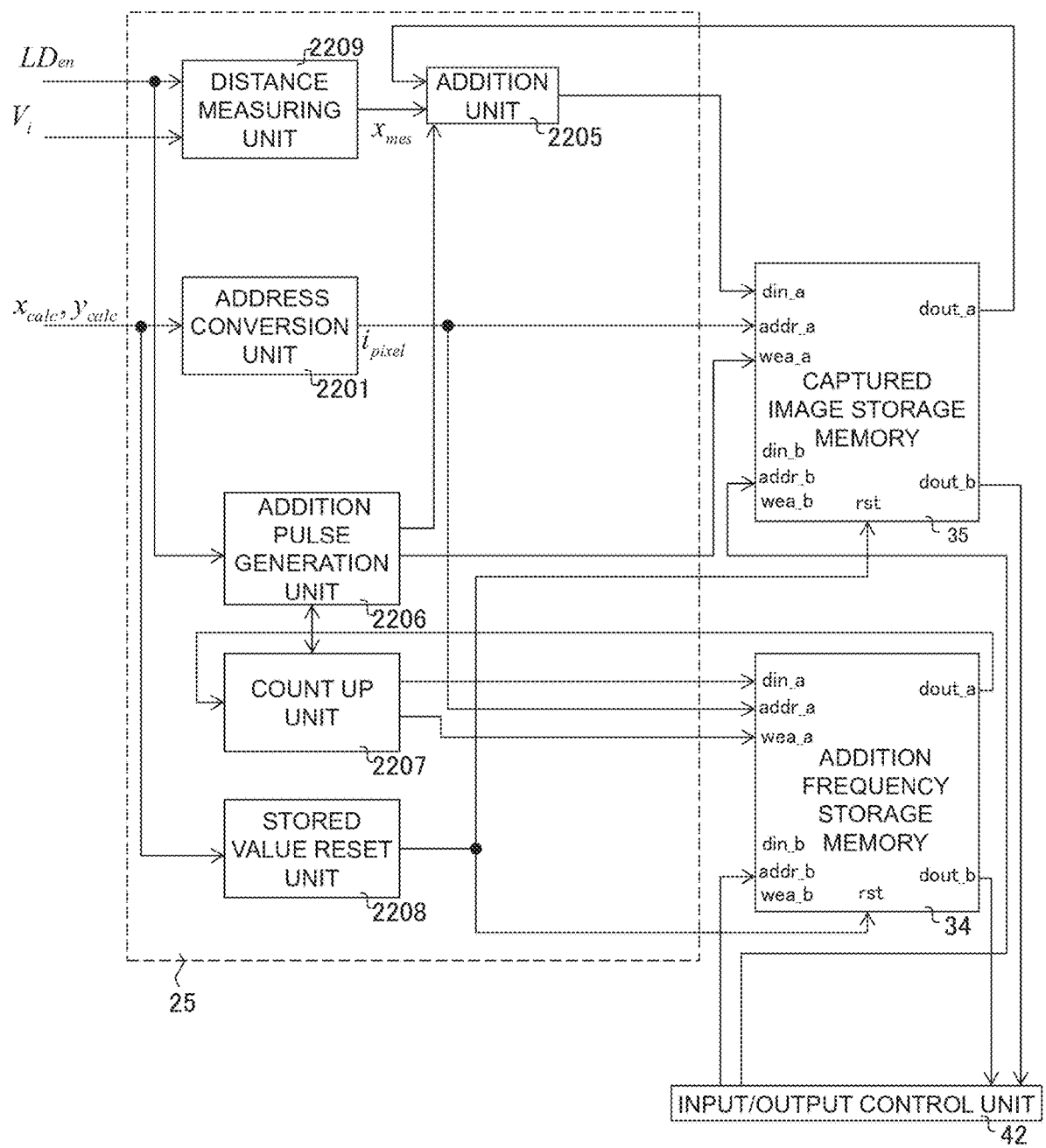
FIG. 20 is a block diagram showing a configuration example of a captured image generation unit 25.

Next, the relationship between the configuration example of the captured image generation unit 25 and the related block will be described with reference to FIG. 20. FIG. 20 is a block diagram showing a configuration example of the captured image generation unit 25.

The captured image generation unit 25 has a configuration similar to that of the imaging data accumulation control unit 22 (FIG. 13) in the catheter device 1, and components common to the imaging data accumulation control unit 22 are denoted by the same reference numerals, and therefore a description thereof will be omitted.

The captured image generation unit 25 includes an address conversion unit 2201, a distance measuring unit 2209, an addition unit 2205, an addition pulse generation unit 2206, a count up unit 2207, and a stored value reset unit 2208.

The address conversion unit 2201 in the catheter device 1 is configured to output a one-dimensional pixel address $i_{pixel}$ to an address concatenation unit 2203, while the address conversion unit 2201 in the distance measuring device 2 is configured to supply the pixel address $i_{pixel}$ to an address terminal addr_a of a port A of the captured image storage memory 35.

The distance measuring unit 2209 receives the $LD_{en}$ signal and the signal $V_i$ from the receiving unit 14 as an input, and measures a distance $x_{mes}$ to an object based on the time from when the laser emission control unit 26 instructs light to be emitted to when the return light is detected by the receiving unit 14. The addition unit 2205 adds the measured distance $x_{mes}$ to data read from a data output terminal dout_a of the port A of the captured image storage memory 35.

That is, in the catheter device 1, a value $V_{conv}$ obtained by digitally converting the photoacoustic signal $V_i$ is integrated, and the integration result is stored in the imaging data storage memory 33. On the other hand, the distance measuring device 2 is configured to integrate the distance $x_{mes}$ measured using the signal $V_i$ and store the integrated value in the captured image storage memory 35.

The signal $V_i$ input from the receiving unit 14 to the distance measuring unit 2209 is a voltage value obtained by converting a current output from a detector into a voltage in the receiving unit 14. Alternatively, the voltage value obtained by converting the current output from the detector into a voltage in the receiving unit 14 may be compared with a predetermined voltage by a comparator, and the comparison result (logic value) may be used as the signal $V_i$.

The captured image storage memory 35 in the distance measuring device 2 has the same function as the imaging data storage memory 33 (FIG. 13) in the catheter device 1. However, the imaging data storage memory 33 is configured to store time series data over the period of the signal storage period tmem with respect to one-time laser emission, whereas the captured image storage memory 35 is configured to store one distance measurement value with respect to one-time laser emission. Therefore, the total number of addresses of True Dual Port Ram is different.

A signal from the input/output control unit 42 is supplied to an address terminal addr_b of a port B of the captured image storage memory 35, and the data output from the data output terminal dout_b of the port B of the captured image storage memory 35 is input to the input/output control unit 42. Similarly, the signal from the input/output control unit 42 is supplied to the address terminal addr_b of the port B of the addition frequency storage memory 34, and the data output from the data output terminal dout_b of the port B is input to the input/output control unit 42.

As a result, an external control device 50 can acquire the data stored in the captured image storage memory 35 and the addition frequency storage memory 34 via the input/output control unit 42. The external control device 50 obtains an average value of the distance $x_{mes}$ by performing a calculation of dividing the value of the captured image storage memory 35 stored in any address by the value of the addition frequency storage memory 34 stored in the same address. In this case, it is possible to obtain the average value of the distance $x_{mes}$ during one frame. By considering the average value of the distance $x_{mes}$ corresponding to each address as a pixel value, the external control device 50 can obtain a distance image by allowing the pixel value to represent the distance to the object.

In the above description, the external control device 50 performs the calculation of dividing the value of the captured image storage memory 35 by the value of the addition frequency storage memory 34 stored in the same address, but the calculation may be performed by the distance measuring device 2. In that case, the external control device 50 can directly receive the average value of the distance $x_{mes}$ corresponding to each address, that is, the distance image via the input/output control unit 42.

In addition, it is also possible to output, for example, only the minimum value of the distance to the object, without outputting a distance image from the distance measuring device 2. In this case, the distance measuring device 2 can be used as a sensor for detecting an object.

The control processing by the controller 40 in the distance measuring device 2 is the same as the control processing by the controller 40 in the catheter device 1 (already described with reference to the flowchart in FIG. 15), and therefore a description thereof will be omitted.

<Effect of Distance Measuring Device 2 According to Second Embodiment>

Next, the effect obtained by the distance measuring device 2 will be described.

As the first effect, as in the first effect of the catheter device 1, it is possible to remove the helical pattern by irradiating the irradiation point to an appropriate position in the distance image.

This means that in the device adopting the optical scanning unit 10, the present invention can be similarly applied regardless of a kind of measured values (intensity of a sound wave/distance information), a measurement principle (photoacoustic/TOF), and a kind of generated images (three-dimensional captured image/distance image).

As the second effect, it is possible to improve the measurement accuracy in the distance image. In the catheter device 1, the effect in the S/N improvement of the captured image is obtained, whereas the distance measuring device 2 can obtain the effect of improving the measurement accuracy of the distance based on the return light.

As the third effect, since the pulsed laser having strong power of the laser beam irradiated can be used, it is possible to extend the measurable distance. This is because the intensity of the return light becomes strong by using the laser beam having strong power, and the distance to the object existing farther away than ever can be measured.

<As to Modified Example of Distance Measuring Device 2 According to Second Embodiment of the Present Invention>

Next, a modified example of the distance measuring device 2 will be described. The distance measuring device 2 measures the distance to the object to generate the distance image, but can be modified to generate (image) a general color image.

Figure 21:
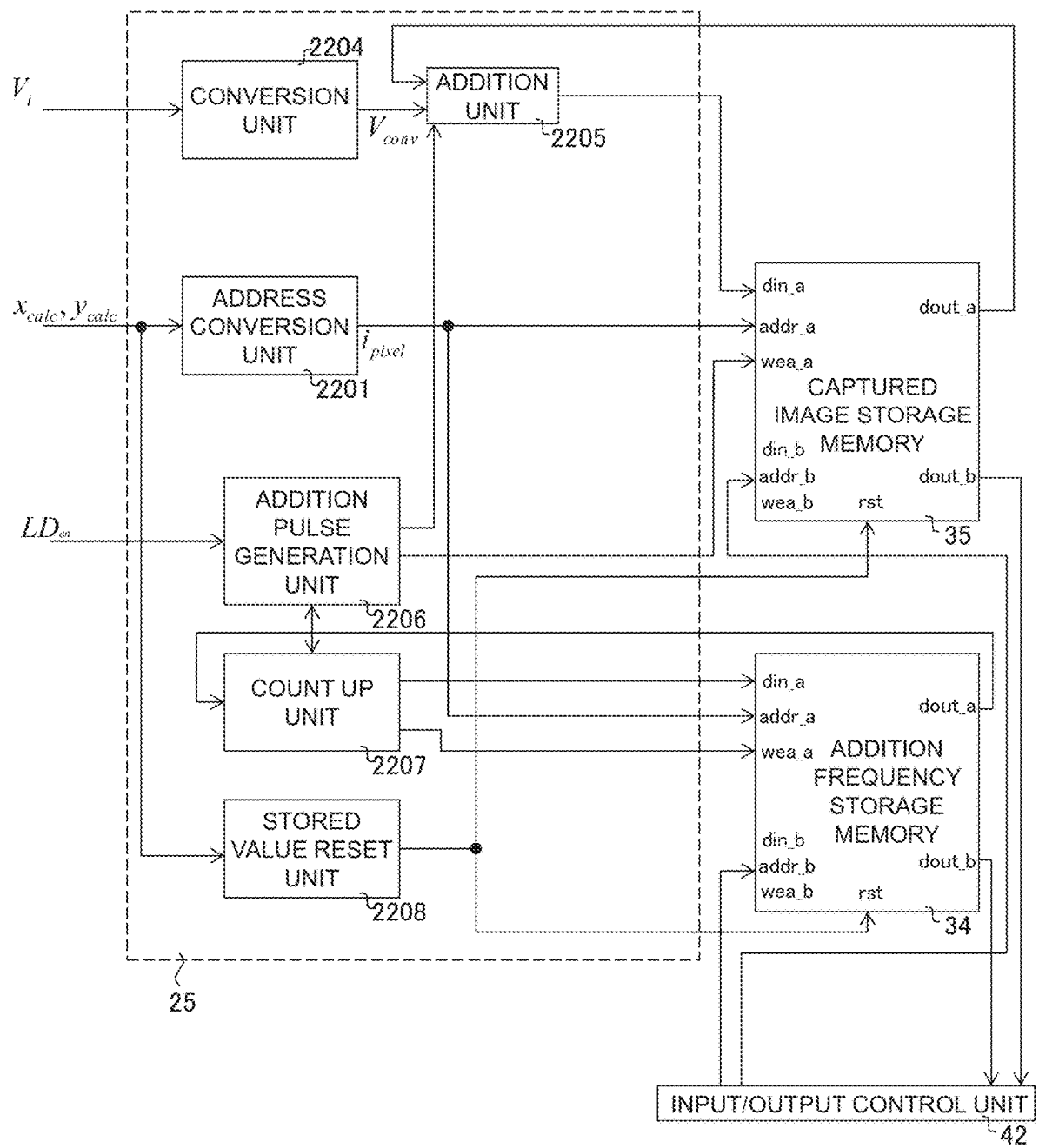
FIG. 21 is a block diagram showing a configuration example of a captured image generation unit 25 corresponding to a modified example of the distance measuring device 2.

In order to modify the distance measuring device 2 so as to generate the color image, the captured image generation unit 25 shown in FIG. 20 may be modified as shown in FIG. 21. That is, FIG. 21 shows a configuration example of the captured image generation unit 25 corresponding to the modified example of the distance measuring device 2. Hereinafter, the configuration example of the captured image generation unit 25 corresponding to the modified example of the distance measuring device 2 is referred to as the modified example of the captured image generation unit 25.

The modified example (FIG. 21) of the captured image generation unit 25 is obtained by replacing the distance measuring unit 2209 in the configuration example (FIG. 20) of the captured image generation unit 25 with the conversion unit 2204. The conversion unit 2204 performs the A/D conversion of the analog signal $V_i$ input from the receiving unit 14 into the digital conversion value $V_{conv}$, and outputs the converted value $V_{conv}$ to the addition unit 2205. The light source unit 1301 of the light emitting unit 13 irradiates the laser beam from the light sources of all colors of R, G, and B which are embedded.

<Effect of Modified Example of Distance Measuring Device 2 According to Second Embodiment>

According to the modified example of the distance measuring device 2, the laser beam of R, G, and B which are the three primary colors of light is irradiated, and the information on the intensity of the return light can be stored in the captured image storage memory 35. This makes it possible to image the color image (still image or moving image).

Even in the modified example, it is possible to remove the helical pattern by irradiating the irradiation point to an appropriate position. In addition, the S/N of the color image can be improved. In addition, it is possible to extend the imaging range of the color image.

<As to Image Device 3 According to Third Embodiment of the Present Invention>

Next, an image device 3 for displaying an image according to a third embodiment of the present invention will be described.

Figure 22:
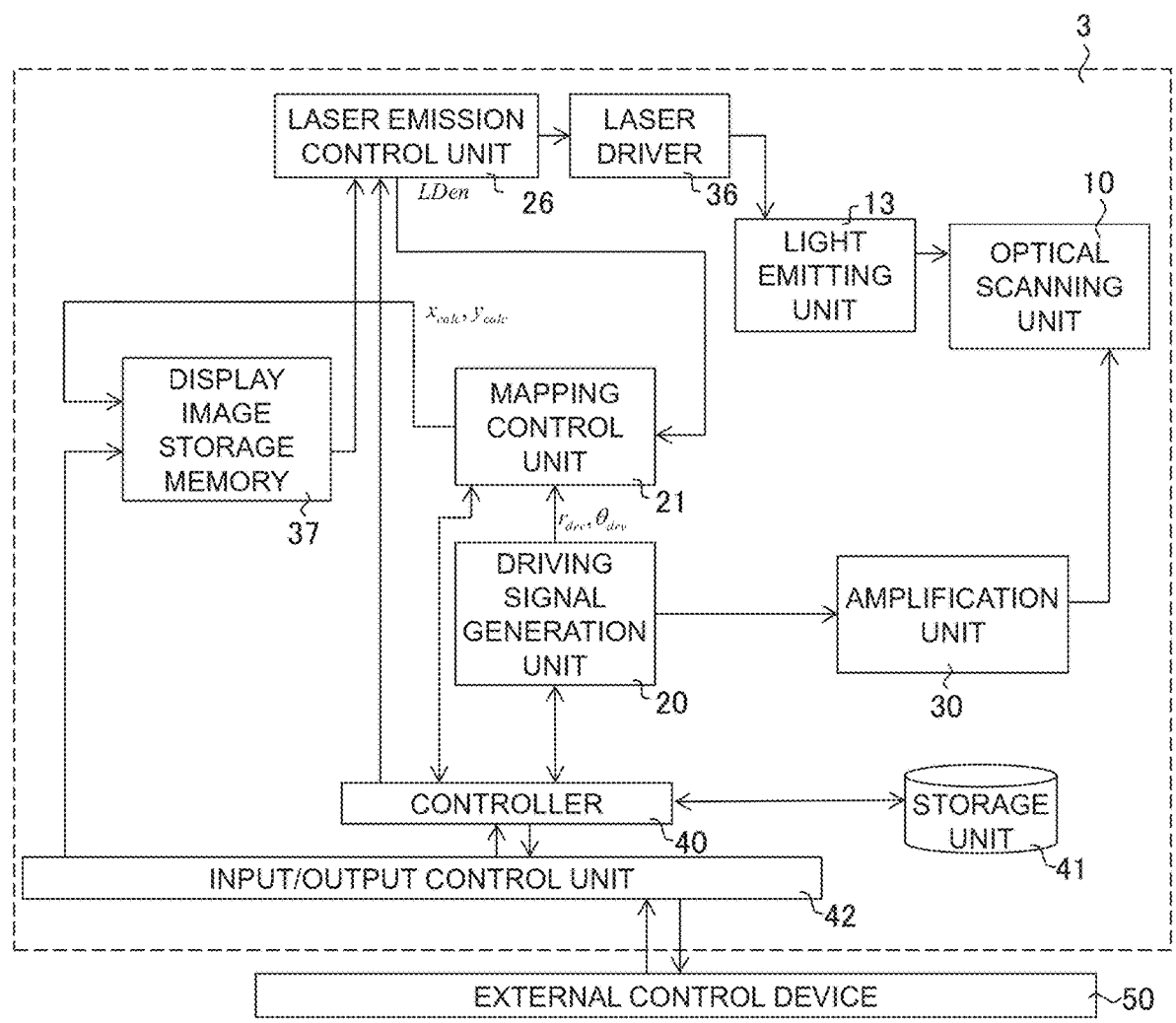
FIG. 22 is a block diagram showing a configuration example of an image device 3 according to a third embodiment.

FIG. 22 is a block diagram showing a configuration example of an image device 3 including the optical scanning unit 10. It is to be noted that, among the components of the image device 3, the same components as those of the distance measuring device 2 are denoted by the same reference numerals, and a description thereof will be omitted.

The image device 3 has a configuration in which the receiving unit 14, the captured image generation unit 25, the addition frequency storage memory 34, and the captured image storage memory 35 are omitted from the distance measuring device 2, and a display image storage memory 37 is added.

The image device 3 has a function of displaying an image based on an image signal acquired from the external control device 50. The image signal acquired by the image device 3 from the external control device 50 via the input/output control unit 42 is stored in the display image storage memory 37. The mapping control unit 21 calculates coordinates in pixel information to be displayed (irradiated) among the image information accumulated in the display image storage memory 37 based on the information from the driving signal generation unit 20. The coordinates ($x_{calc}$, $y_{calc}$) calculated by the mapping control unit 21 are supplied to the display image storage memory 37, and gradation data (R, G, and B) of pixels on the corresponding coordinates are supplied to the laser emission control unit 26.

The laser emission control unit 26 generates a light emission control signal for controlling the emission of the laser based on the gradation data (R, G, and B) of the pixels, and supplies the generated light emission control signal to the laser light source provided in the light emitting unit 13 via the laser driver 36. The laser beam emitted from the light emitting unit 13 is irradiated to the projection plane (irradiated surface) via the optical scanning unit 10. As a result, the emission of the laser is controlled in synchronization with the scanning of the light, and the image is displayed.

In the image device 3, the relationship between the light emission frequency $f_{dot}$ of the laser and the driving frequency $f_{drv}$ of the vibration unit 101 is determined so as to satisfy the same relationship as the case of the catheter device 1 and the distance measuring device 2. That is, the relationship between the light emission frequency $f_{dot}$ and the driving frequency $f_{drv}$ are determined so that among lengths of four sides of a substantially parallelogram constituted by four neighboring points on an outermost circumference of an irradiation region of the irradiation light, lengths of adjacent sides are substantially equal. As a result, the image device 3 can irradiate the irradiation point to an appropriate position.

<Effect of Image Device 3 According to Third Embodiment>

Next, the effect of displaying the image by the image device 3 will be described.

As the first effect, the catheter device 1 and the distance measuring device 2, it can be mentioned that the helical pattern can be removed by irradiating the irradiation point to an appropriate position in the display image.

As the second effect, it can be mentioned that a luminance of the displayed image can be maintained. For example, when the irradiation of the laser beam is thinned out, the luminance of the image on the projection plane is lowered. However, in the image device 3, since the irradiation is repeatedly and continuously performed the light emission frequency $f_{dot}$ without thinning out the irradiation of the laser beam, the luminance of the image displayed on the projection plane can be maintained.

As the third effect, it can be mentioned that since the pulsed laser having strong power can be used as a laser, it is possible to extend the distance to the projection plane on which the image is displayed.

<As to Catheter Device 4 According to Fourth Embodiment of the Present Invention>

Next, a catheter device 4 according to a fourth embodiment of the present invention will be described.

The catheter device 4 is configured to compensate for a temperature characteristic when a piezoelectric element 1010 constituting the vibration unit 101 has temperature characteristics while obtaining the same effect as the catheter device 1.

Figure 23:
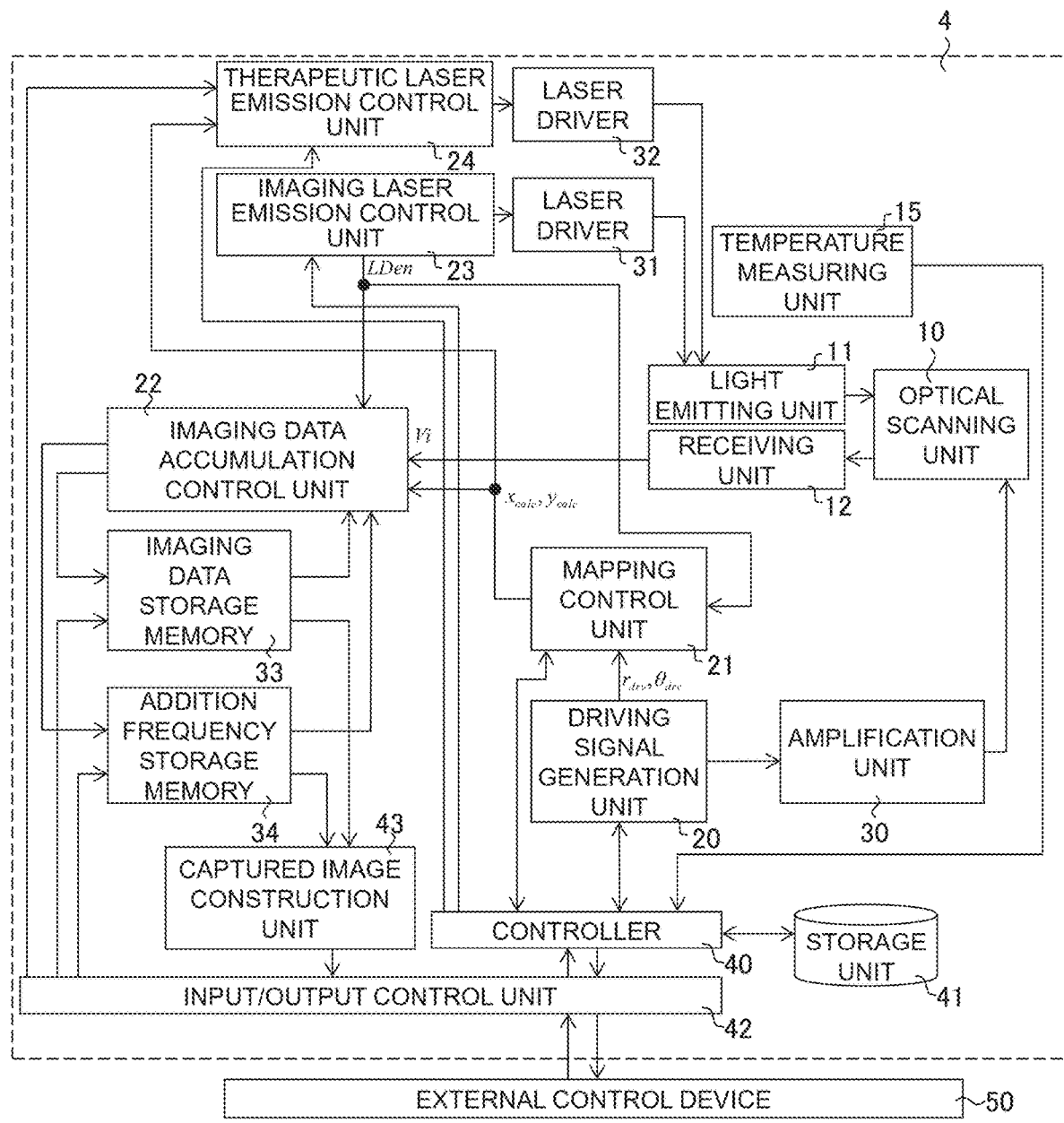
FIG. 23 is a block diagram showing a configuration example of a catheter device 4 according to a fourth embodiment.

FIG. 23 is a block diagram showing a configuration example of the catheter device 4. It is to be noted that, among the components of the catheter device 4, the same components as those of the catheter device 1 (FIG. 1) are denoted by the same reference numerals, and a description thereof will be omitted.

The catheter device 4 has a configuration in which a temperature measuring unit 15 is added to the catheter device 1.

The temperature measuring unit 15 is attached to, for example, a tip of a catheter (not shown), measures the temperature of the tip of the catheter at all times, and notifies the controller 40 of the measurement result.

Figure 24:
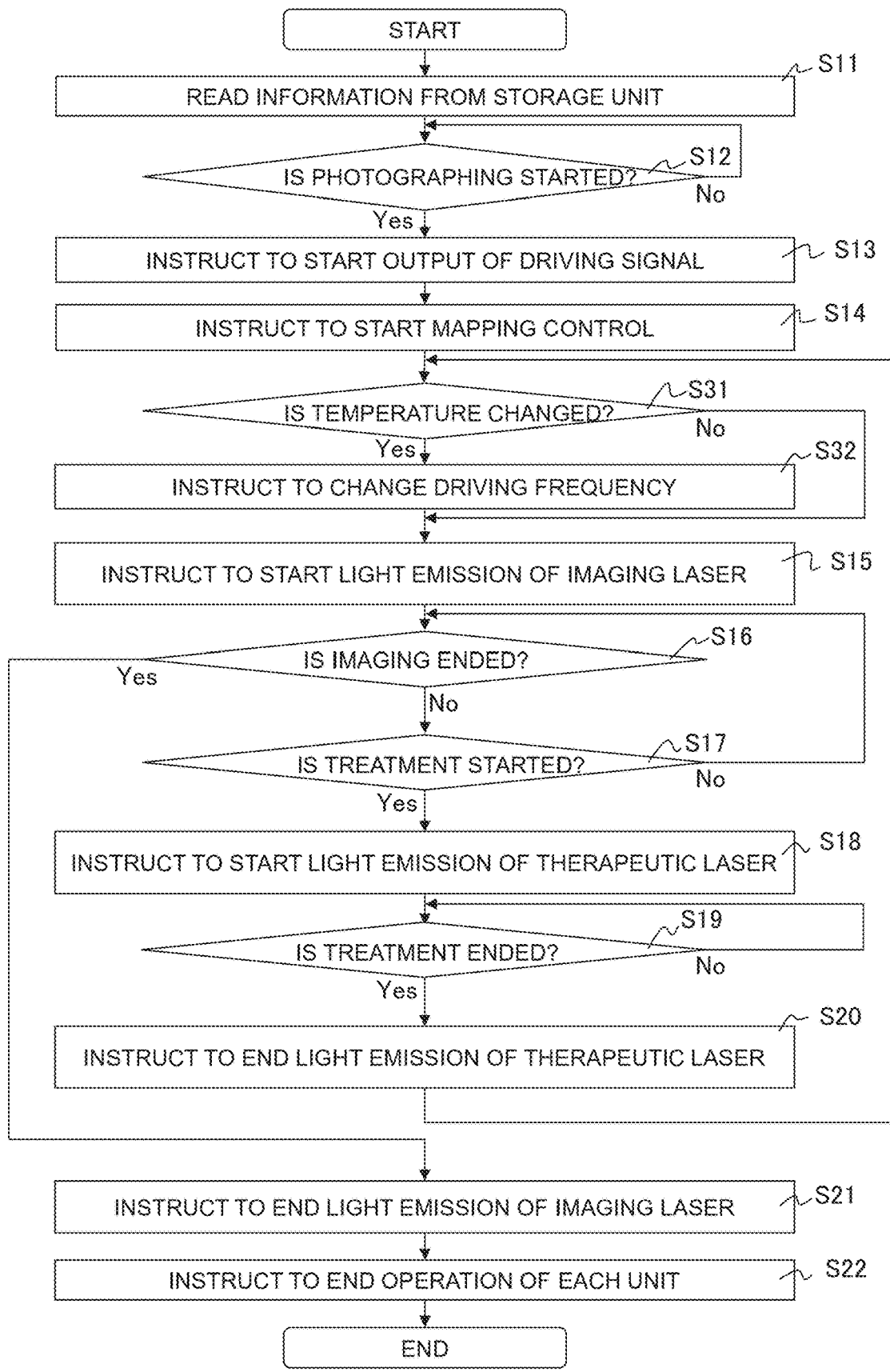
FIG. 24 is a flowchart showing an example of control processing by a controller 40 of the catheter device 4.

Next, FIG. 24 is a flowchart for describing an example of the control processing by the controller 40 in the catheter device 4. In the control processing, processing of steps S31 and S32 are added between the processing of step S14 and the processing of step S15 of the flowchart (FIG. 15) for describing the control processing by the controller 40 in the catheter device 1.

After the processing of step S14 or S20 is performed, the controller 40 determines whether the temperature notified from the temperature measuring unit 15 has changed from the temperature held by the controller 40 (step S31). If it is determined that the temperature is changing (Yes in step S31), the controller 40 controls the driving signal generation unit 20 to indicate the change in the driving frequency $f_{drv}$ of the vibration unit 101 (step S32). Details of step S32 will be described later. After step S32, the processing proceeds to step S15.

To the contrary, when the controller 40 determines that the temperature is not changed (No in step S31), step S32 is skipped and the processing proceeds to step S15.

By the processing of such steps S31 and S32, it is possible to change the driving frequency $f_{drv}$ of the vibration unit 101 according to the temperature change.

Here, a method for changing the driving frequency $f_{drv}$ in step S32 will be described.

As described above, if the light emission frequency $f_{dot}$ of the laser beam, the driving frequency $f_{drv}$ of the vibration unit 101, and the number $N_{frame}$ of turns of the spiral trajectory are determined, the ratio d/c of the sides can be calculated.

However, as described with reference to FIG. 7(A) and FIG. 7(B) and the like, when only the driving frequency $f_{drv}$ is changed, there is the condition that the helical pattern is conspicuous. The condition that the helical pattern is not conspicuous is represented by, for example, the above Mathematical Formula (16).

The present inventor has found that a band exists in the driving frequency $f_{drv}$ satisfying the above Mathematical Formula (16). The band of the driving frequency $f_{drv}$ satisfying the above Mathematical Formula (16) will be described with reference to FIGS. 25A to 25D.

FIGS. 25A to 25D show frequency characteristics of the amplitude of the light emitting end 102a of the light guide path 102. A horizontal axis of a mountain-shaped line graph shown in FIGS. 25A to 25D is the driving frequency $f_{drv}$, and a vertical axis is the amplitude of the light emitting end 102a.

Figure 25A:
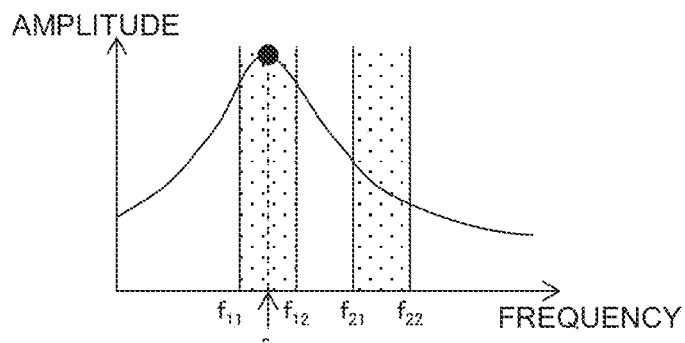
FIGS. 25A to 25D are diagrams for explaining a frequency at which a helical pattern is not conspicuous.

FIG. 25A shows frequency characteristics at a predetermined initial temperature. A frequency $f_{11}$ and a frequency $f_{12}$ are in a range of the driving frequency $f_{drv}$ that satisfies the above Mathematical Formula (16). That is, the above Mathematical Formula (16) is satisfied in a frequency band (hatched region in the drawing) where the driving frequency $f_{drv}$ is $f_{11}$ or more and $f_{12}$ or less. Similarly, the frequency band in which the driving frequency $f_{drv}$ is $f_{21}$ or more and $f_{22}$ or less can also satisfy the above Mathematical Formula (16).

As shown in FIGS. 25A to 25D, the present inventor found that a width from the frequency $f_{11}$ to the frequency $f_{12}$ is substantially equal to a width from the frequency $f_{21}$ to the frequency $f_{22}$. The relationship between the width from the frequency $f_{11}$ to the frequency $f_{12}$ and the width from the frequency $f_{12}$ to the frequency $f_{21}$ is affected depending on to which value the threshold of the ratio d/c of the sides is set when the helical pattern appears and does not appear.

That is, in the catheter device 1, the threshold is set to 2, but it is obvious that the ratio d/c of the sides is preferably close to 1, and the determination may be made by setting the threshold to be, for example, 1.5. In this case, the width of the hatched frequency region (the width from the frequency $f_{11}$ to the frequency $f_{12}$) becomes narrow, and conversely the width of frequencies from $f_{12}$ to the frequency $f_{21}$ becomes wide. In either case, the frequencies (for example, $f_{11}$ and $f_{12}$) of the boundary of the hatched frequency region satisfy the above Mathematical Formula (16).

Figure 25B:
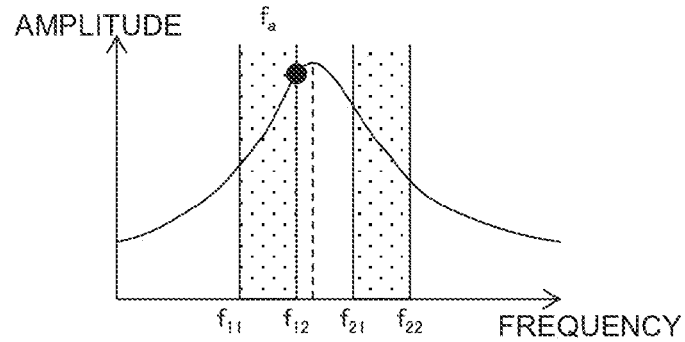
Figure 25C:
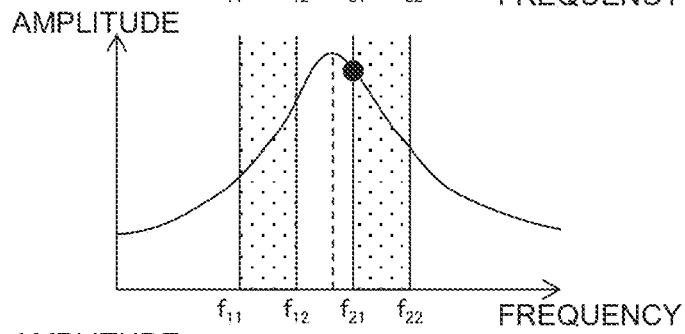
Figure 25D:
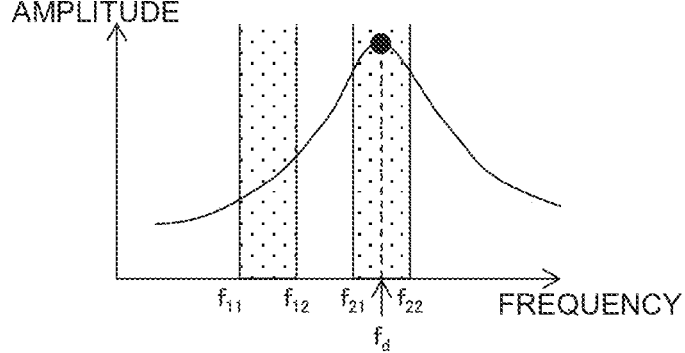

FIGS. 25B to 25D sequentially show the appearance that the temperature gradually rises from the initial temperature, and the frequency characteristics of the vibration unit 101 are changed. In the state of FIG. 25A, since a frequency $f_a$ of the maximum amplitude of the vibration unit 101 (the position of the black circle in FIG. 25A) exists in the hatched region, an optimum frequency $f_a$ at which the vibration unit 101 can vibrate maximally can be designated as the driving frequency $f_{drv}$.

On the other hand, in FIGS. 25B and 25C, the frequency at which the amplitude becomes maximum exists outside the hatched region. In this case, the frequency at which the amplitude becomes maximum within the hatched region (the position of the black circle in FIGS. 25B and 25C) is designated as the driving frequency $f_{drv}$. That is, in the case of FIG. 25B, the driving frequency $f_{drv}$ is designated as $f_{12}$, and in the case of FIG. 25C, the driving frequency $f_{drv}$ is designated as $f_{21}$. In addition, when the temperature is changed to be in the state of FIG. 25D, the frequency $f_d$ at which the amplitude of the vibration unit 101 is maximum (the position of the black circle in FIG. 25D) can be designated as the driving frequency $f_{drv}$. In this manner, the catheter device 4 changes the driving frequency $f_{drv}$ while avoiding the predetermined frequency band.

Figure 26:
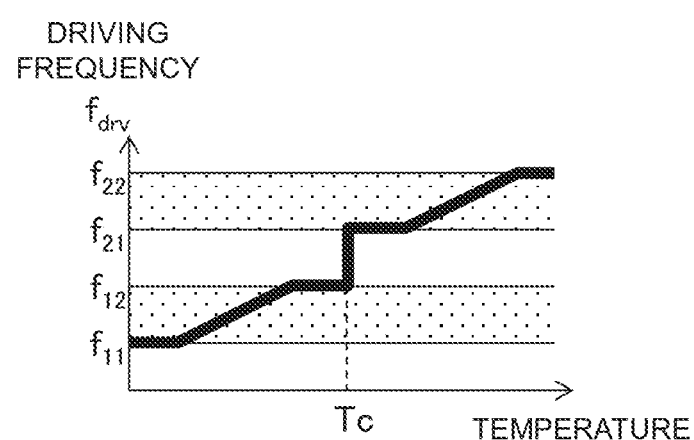
FIG. 26 is a diagram showing an example of a relationship between temperature and a driving frequency $f_{drv}$.

FIG. 26 shows the relationship between the temperature of the tip part of the catheter described above and the driving frequency $f_{drv}$ designated accordingly.

As the features of the change in the driving frequency $f_{drv}$ according to the change in temperature by the controller 40 (corresponding to the frequency change unit of the present invention) of the catheter device 4, it can be mentioned that there is a temperature (temperature Tc in FIG. 26) at which the driving frequency $f_{drv}$ is discretely changed and when the amplitude becomes maximum at the temperature Tc, the driving frequency $f_{drv}$ does not satisfy the above Mathematical Formula (16).

In the catheter device 4, it is assumed that the controller 40 previously stores the relationship of the optimum driving frequency $f_{drv}$ with respect to the temperature.

In the catheter device 4, the driving frequency $f_{drv}$ is changed according to the temperature measured by the temperature measuring unit 15. However, as an index for indicating the change in the driving frequency $f_{drv}$, indices other than temperature may be used. For example, the vibration amplitude of the light guide path 102 may be detected, and the change in the driving frequency $f_{drv}$ may be indicated using the vibration amplitude as an index.

<Effect of Catheter Device 4 According to Fourth Embodiment>

Next, the effect by the catheter device 4 will be described. According to the catheter device 4, even when the frequency characteristic of the amplitude at the light emitting end 102a of the light guide path 102 is lowered due to the change in temperature and thus the amplitude is lowered, the same effect as the catheter device 1 can be obtained by changing the driving frequency $f_{drv}$.

<As to Catheter Device 5 According to Fifth Embodiment of the Present Invention>

Next, a catheter device 5 according to a fifth embodiment of the present invention will be described. The catheter device 5 has the same configuration as the catheter device 1 shown in FIG. 1, and an illustration thereof is omitted.

In the catheter device 1, for example, as shown in FIGS. 8A and 8B, three values of the light emission frequency $f_{dot}$ of the laser, the driving frequency $f_{drv}$ of the vibration unit 101, and the number $N_{frame}$ of turns of the spiral trajectory are determined so that the ratio d/c of the sides satisfies the above Mathematical Formula (16). That is, when the helical pattern appears as shown in FIG. 7A, at least one value of the light emission frequency $f_{dot}$, the driving frequency $f_{drv}$, and the number $N_{frame}$ of turns of the spiral trajectory is changed, which was explained.

However, the method for changing the ratio d/c of the sides is not limited thereto. For example, the ratio d/c of the sides can also be changed by changing the time delay of the light emission instruction pulse transmitted by the imaging laser emission control unit 23. In addition, the ratio d/c of the sides can also be changed even by changing the light emission frequency $f_{dot}$ of the imaging laser within the predetermined frequency range.

The catheter device 5 removes the helical pattern by changing the time delay of the light emission instruction pulse transmitted by the imaging laser emission control unit 23. Since the effect of changing the time delay is not taken into account in the above Mathematical Formula (16), the above Mathematical Formula (16) is not established in the catheter device 5.

In the catheter device 5, the driving frequency $f_{drv}$ of the vibration unit 101 is set to 10.19 kHz. In this condition, when the time delay amount of the imaging laser is not changed, the helical pattern can be visually recognized as shown in FIG. 7A.

In the catheter device 5, the controller 40 controls the imaging laser emission control unit 23 so as to change the time delay of the light emission instruction pulse transmitted by the imaging laser emission control unit 23.

The control by the controller 40 will be described with reference to FIG. 27.

Figure 27:
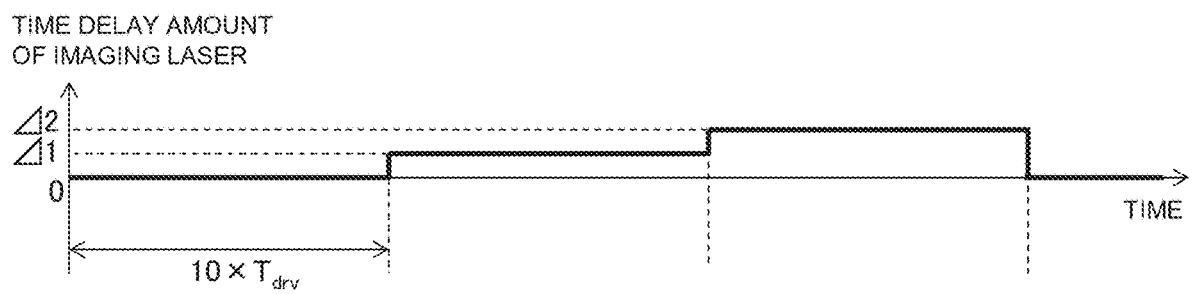
FIG. 27 is a diagram showing an example of a time change in a time delay amount of an imaging laser.

FIG. 27 shows the time change in the time delay amount of the imaging laser. The cycle $T_{drv}$ is a cycle $T_{drv}$ ($=1/f_{drv}$) of the X-axis driving sine wave sin1 and the Y-axis driving sine wave sin2. In the catheter device 5, the time delay amount of the imaging laser is changed stepwise from 0 to Δ1 and furthermore Δ2, having a time of 10 times the cycle $T_{drv}$ as a period. The reason will be described.

In the catheter device 1, $N_p$ was 11 as shown in the above Mathematical Formula (6). This means that irradiation points are arranged at similar angles after eleven turns, and a helical vortex is formed. When the time delay amount of the imaging laser is changed, the positions where the irradiation points are arranged can be rotated about the origin. At that time, since the angle is similar every eleven turns, it is preferable to change the time delay amount of the imaging laser every ten turns. Therefore, the helical pattern can be removed by appropriately setting the time delay amounts Δ1 and Δ2 in FIG. 27.

That is, it is preferable to change the time delay amount of the imaging laser every time of $(N_p-1) \times T_{drv}$. In addition, the period of $(N_p-1) \times T_{drv}$ is a stepped waveform having a constant value. However, the time delay amount of the imaging laser may change during the period of $(N_p-1) \times T_{drv}$. Even in that case, it is preferable that the time delay amount of the imaging laser has changed after the time of at least $(N_p-1) \times T_{drv}$ has elapsed. That is, the time delay amount of the imaging laser may be changed within the time of $(N_p-1) \times T_{drv}$ or less.

<Effect of Catheter Device 5 According to Fifth Embodiment>

The effect by the catheter device 5 is the same as the effect by the catheter device 1. In addition, it is obvious that even in the case in which the helical pattern is removed by the catheter device 5, the relationship "in the region in which the density of the irradiation points is relatively low, among the lengths of four sides of the substantially parallelogram constituted by four neighboring points, the lengths of adjacent sides are substantially equal" is similarly established.

<As to Modified Example of Catheter Device 5>

In a modified example of the catheter device 5, the ratio d/c of the sides is changed by changing the light emission frequency $f_{dot}$ of the imaging laser within the predetermined frequency range.

In the modified example of the catheter device 5, the light emission frequency $f_{dot}$ of the laser is changed in the range of, for example, 49.8 kHz to 50.2 kHz in a time of $(N_p-1) \times T_{drv}$ or less. This helical pattern can be removed even by this R.

That is, in the catheter device 5 and the modified example thereof, it is said that in the region in which the density of the irradiation points is relatively low in the region in which the irradiation light is irradiated, the imaging laser emission control unit 23 irradiates any irradiation point and then the time interval $T_{dot}$ until the next irradiation point is irradiated is changed at the time of $(N_p-1) \times T_{drv}$ or less. The catheter device 5 changes the time interval $T_{dot}$ only at the stepped part in FIG. 27, and changing the time interval $T_{dot}$ more finely is a modified example of the catheter device 5.

The change in the time interval $T_{dot}$ in the catheter device 5 and the modified example thereof may be made over the entire region of the spiral trajectory, or in particular, only at the outer circumferential part where it is necessary to remove the helical pattern.

<As to Catheter Device 6 According to Sixth Embodiment of the Present Invention>

Next, a catheter device 6 according to a sixth embodiment of the present invention will be described. The catheter device 6 has the same configuration as the catheter device 1 shown in FIG. 1, and an illustration thereof is omitted. However, in the catheter device 6, the calculation performed by an angle correction unit 2101 and a coordinate calculation unit 2102 (FIG. 6) constituting the mapping control unit 21 is different from that of the catheter device 1.

Since the optical scanning unit 10 of the catheter device 1 performs the scanning of the laser beam using the resonance of the cantilever constituted by the light guide path 102, the light emitted from the light guide path 102 does not draw an ideal trajectory and the projection image may be distorted.

The catheter device 6 is configured to correct the distortion occurring in the projection image.

Figure 28A:
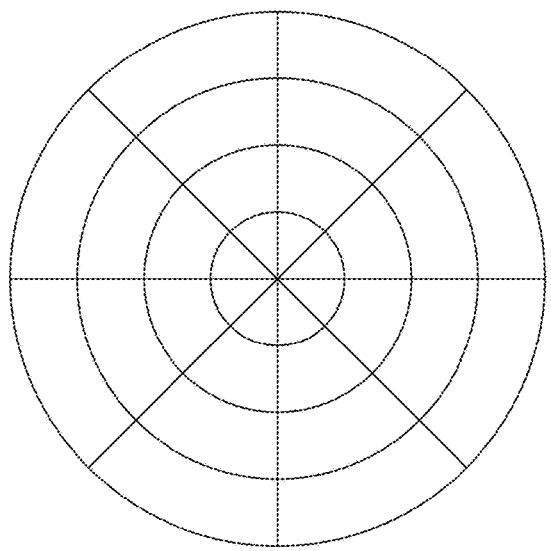
FIGS. 28A and 28B are diagrams for explaining a distortion of a projection image.
Figure 28B:
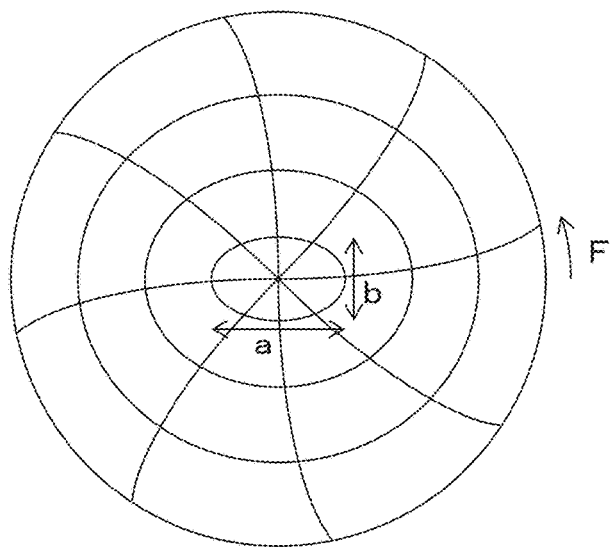
Figure 29:
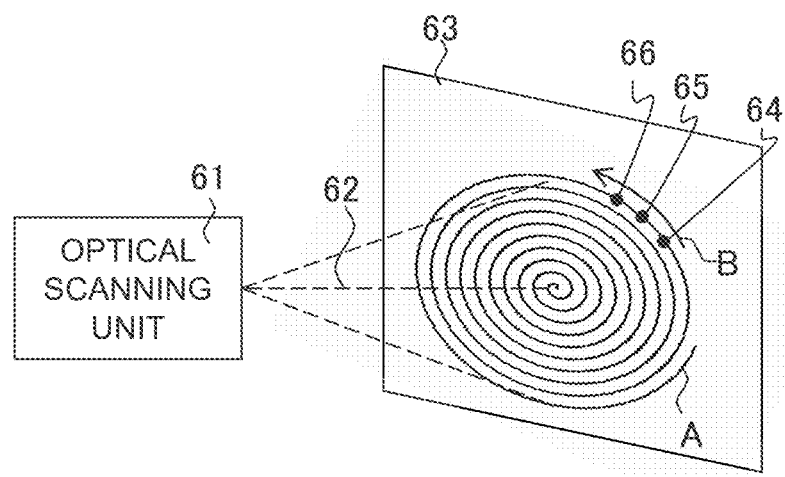
FIG. 29 is a diagram for explaining a definition of irradiation points.

FIGS. 28A and 28B are diagrams for describing a distortion that may occur in the projection image by the optical scanning unit 10. FIG. 28A shows, as an example of a projection image (image without distortion), an image composed of a plurality of concentric circles having different radii and a plurality of straight lines passing through centers of the concentric circles and having different inclinations. FIG. 28B shows the distorted projection image which is obtained by allowing the optical scanning unit 10 to project the image shown in FIG. 28A.

Hereinafter, the calculations of the angle correction unit 2101 and the coordinate calculation unit 2102 constituting the mapping control unit 21 of the catheter device 6 will be described.

The angle correction unit 2101 of the catheter device 6 calculates a correction angle $\theta_{calc}$ according to the following Mathematical Formula (28) using an angle $\theta_{drv}$ and the radius $r_{drv}$ from the driving signal generation unit 20.

[Mathematical Formula 28]

$$\theta_{calc} = \theta_{drv} + f(r_{drv}) \qquad (28)$$

The coordinate calculation unit 2102 performs calculations represented by Mathematical Formulas (29) and (30), and outputs $x_{calc0}$ and $y_{calc0}$ obtained as the calculation results.

[Mathematical Formula 29]

$$x_{calc0} = \text{round}(a(r_{drv}) \cdot r_{drv} \cos(\theta_{calc})) \qquad (29)$$

[Mathematical Formula 30]

$$y_{calc0} = \text{round}(b(r_{drv}) \cdot r_{drv} \sin(\theta_{calc})) \qquad (30)$$

In the above Mathematical Formulas (28) to (30), $f(r_{drv})$, $a(r_{drv})$, and $b(r_{drv})$ are a function of using the radius $r_{drv}$ as an argument, and these functions are instructed from the controller 40.

$x_{calc0}$ and $y_{calc0}$ obtained from the above Mathematical Formulas (29) and (30) are the coordinate information for correcting the distortion of the projection image. As a result, the imaging of the corrected image whose distortion is corrected becomes possible.

It is to be noted that even in the catheter device 6, the angle correction unit 2101 and the coordinate calculation unit 2102 may be integrated to perform the calculations of the above Mathematical Formulas (28) to (30) collectively.

In addition, even in the catheter device 6, the relationship between the light emission frequency $f_{dot}$ of the imaging laser and the driving frequency $f_{drv}$ of the vibration unit 101 is determined so as to satisfy the same relationship as the case of the catheter device 1. That is, the light emission frequency $f_{dot}$ and the driving frequency $f_{drv}$ are determined so that among lengths of four sides of a substantially parallelogram constituted by four neighboring points on an outermost circumference of an irradiation region of the irradiation light, lengths of adjacent sides are substantially equal.

<Effect of Catheter Device 6 According to Sixth Embodiment>

Next, the effect by a catheter device 6 will be described.

As the first effect, it is possible to favorably correct the distortion of the projection image. As described with reference to FIG. 28A and FIG. 2B, when the image as shown in FIG. 28A is projected as the projection image, the actual projection image is distorted as shown in FIG. 28B. The inventor found that it is possible to favorably realize the projection image without distortion by specifying the distortion occurring in the projection image, classifying the distortion occurring in the projection image into two types, and properly correcting each of the two types of distortions. The features of the two types of image distortions will be described.

The first image distortion is a distortion in a rotational direction shown by F in FIG. 28B. This distortion in the rotation direction has a feature that it is uniform regardless of the rotation angle.

The second image distortion is a distortion in which the trajectory of the inner circumference becomes elliptical when the amplitude modulation is performed so as to draw the spiral trajectory under the condition that it becomes a circle on the outermost circumference. That is, as shown by a and b in FIG. 28B, the trajectory which is to be originally a perfect circle is an ellipse whose length of a major axis a and length of a minor axis b are different from each other on the inner circumference. Hereinafter, this distortion is referred to as inner circumference elliptic distortion. The inner circumference elliptic distortion has a feature that ellipticity is changed according to the radius.

In the catheter device 6, the first and second image distortions described above are appropriately corrected in the mapping control unit 21.

Specifically, first, to cope with the first image distortion (distortion in the rotation direction), the angle correction unit 2101 calculates the correction angle $\theta_{calc}$ using the above Mathematical Formula (28), and corrects the rotation angle of the coordinates used when the imaging data are stored in the imaging data storage memory 33. This correction is determined by the function $f(r_{drv})$ instructed from the controller 40. That is, the information on the function $f(r_{drv})$ is stored in advance in the storage unit 41, and the controller 40 reads the information from the storage unit 41 and issues an instruction to the angle correction unit 2101.

Then, to cope with the second image distortion (distortion in inside and outside ellipticity), the coordinate calculation unit 2102 calculates $x_{calc0}$ and $y_{calc0}$ using the above Mathematical Formulas (29) and (30), and corrects the conversion of the coordinates used when stored in the imaging data storage memory 33 by changing from a circle to an ellipse. This correction is determined by the function $a(r_{drv})$ and the function $b(r_{drv})$ instructed from the controller 40. The information on these functions is also stored in the storage unit 41.

By correcting the rotation angle $\theta_{calc}$ and the coordinates $x_{calc0}$ and $y_{calc0}$ as described above, even if the image distortion occurs as shown in FIG. 28B, the catheter device 6 corrects the image distortion to obtain the image without distortion as shown in FIG. 28A.

As the second effect, it is possible to obtain the same effect as the catheter device 1 after correcting the image distortion. The reason is that as is apparent from FIG. 28B, the inner circumference elliptic distortion is greatly deformed at the central part, and thus a perfect circle is distorted to an ellipse, but the distortion is small at the outer circumference part and thus the shape approximates a perfect circle. In addition, as can be understood from the fact that the distortion in the rotation direction is corrected by the rotation angle $\theta_{calc}$ calculated using the above Mathematical Formula (27), the distortion does not depend on the rotation angle, and gradually changes in the radial direction. Therefore, the distortion can be ignored in the radial region in which there is the substantially parallelogram constituted by four neighboring points on the outermost circumference of the region in which the irradiation light is irradiated.

In this way, the distortion can be almost ignored in the radial region in which there is the substantially parallelogram constituted by four neighboring points on the outermost circumference of the region in which the irradiation light is irradiated. Therefore, for example, the above Mathematical Formula (17) may be used as it is. In addition, focusing on the central part, the helical pattern in the central part becomes information within the one pixel, so it cannot be seen as the helical pattern in the captured image. Therefore, even if the distortion is corrected by the catheter device 6, the effect of the catheter device 1 can be maintained.

SUMMARY

As described above, with respect to the catheter device 1 according to the first embodiment of the present invention, the function of imaging the inside of the blood vessel using the photoacoustic imaging method was described, with respect to the distance measuring device 2 according to the second embodiment of the present invention, the function to acquire the distance image by the TOF method was described, and with respect to the modified example of the distance measuring device 2, the function of imaging the color image was described.

Therefore, it can be referred to as the "imaging" function, including the function included in the first and second embodiments (including modified examples). That is, the "imaging" function in the present specification not only includes the acquisition of the image in accordance with the visible light performed by a general camera, but also the acquisition of the captured image in the blood vessel using the photoacoustic imaging method and the acquisition of the distance image acquired by the TOF method.

Here, in each of the embodiments, the detection of the irradiation result of the irradiation light and the information used for the imaging are summarized.

In the case of the catheter device 1, the intensity of the sound wave was detected by the photoacoustic element 121, and the imaging was performed based on the information. In the case of the distance measuring device 2, the receiving unit 14 detects the intensity of the return light from the object, and the distance to the object is measured and imaged based on the output signal from the receiving unit 14. In addition, in the case of the modified example of the distance measuring device 2 and the modified example of the second embodiment, the receiving unit 14 detects the intensity of the return light from the object, and performs the imaging based on the information. Therefore, when including them, it can be expressed as "including the receiving unit that receives the result of irradiation of the irradiation light and capturing an image based on the information of the receiving unit".

In each of the embodiments, the laser scanning is performed so as to repeatedly draw the trajectory in the spiral trajectory, but the present invention is also applicable to other scanning. For example, the present invention can also be applied to the case of performing Lissajous scanning. This is because the irradiation points are arranged having the predetermined periodicity from the relationship between the periodicity of scanning and the periodicity of laser emission. For this reason, the pattern (in the case of not the spiral trajectory, it is not necessarily limited to the helical shape) described as the problem in the present invention may occur. For example, in the case of the Lissajous scanning, the region in which the density of the irradiation points is lowest becomes the central part of the irradiation region. Even in this case, since the a and b of the sides in the region in which the density of the irradiation points is lowest are substantially equal, it is possible to irradiate the irradiation point to an appropriate position.

In each of the embodiments, the optical scanning unit 10 that drives the light guide path 102 using the hollow cylindrical piezoelectric element 1010 is adopted, but the configuration of the optical scanning unit 10 is not limited thereto. For example, an optical scanning unit using a resonating MEMS mirror may be adopted. Since the resonating MEMS mirror has the periodicity of the scanning, the irradiation points are arranged having the predetermined periodicity from the relationship between the periodicity of the scanning and the periodicity of the laser emission. Therefore, the pattern described as the problem in the present invention may be generated.

However, in the above description, as an effect of each of the embodiments, the point that the pulsed laser having strong power can be used is mentioned, but considering this effect, the configuration of the optical scanning unit 10 driving the light guide path 102 by using the hollow cylindrical piezoelectric element 1010 is preferable. This is because the pulsed laser having strong power tends to be large, which usually means that the size of the optical scanning unit is increased. However, with the configuration of the optical scanning unit 10 described above, the laser light source can be disposed at a position away from the optical scanning unit 10, which does not lead to an increase in size of the optical scanning unit 10. The fact that the optical scanning unit 10 does not increase in size is particularly advantageous in the catheter device 1 or the distance measuring device 2. In each of the embodiments, the light source is a laser, but the present invention is also applicable to the case in which the light source other than the laser is used.

The value stored in the captured image storage memory 35 is the integrated value of the distance measured based on the return light in the case of the distance measuring device 2 and is the integrated value of the intensity of the return light in the case of the modified example of the distance measuring device 2. Therefore, the value stored in the captured image storage memory 35 can be referred to as "information related to the return light" including these values.

In addition, it is also possible to construct the image using "information related to return light" other than the above. For example, it is also possible to measure the time until the intensity of the return light is lowered to a predetermined threshold or less and store the time in the captured image storage memory 35 to construct an image. This can be applied, for example, when the object to be imaged is a phosphor and the sensitivity of the phosphor is measured.

In addition, for example, the time response of the return light may be accumulated only for a predetermined period, and the information (for example, the period at which the return light blinks) obtained from the accumulated information may be stored in the captured image storage memory 35 to construct an image.

In addition, with respect to "information related to the return light" stored in the captured image storage memory 35, the predetermined information may not be integrated.

For example, in the case of the modified example of the distance measuring device 2, it is possible not to perform the integration by changing the configuration of the captured image generation unit 25. In this case, in FIG. 21, the conversion value $V_{conv}$ output from the conversion unit 2204 may be supplied not to the addition unit 2205 but to the terminal din_a of the captured image storage memory 35. In this case, since the addition unit 2205, the addition pulse generation unit 2206, the count up unit 2207, and the addition frequency storage memory 34 can be omitted, the capacity of the captured image generation unit 25 can be reduced. In addition, even in this case, it is possible to obtain the effect of reducing the helical pattern and the effect of using the pulsed laser having strong power. That is, the irradiation point can be irradiated to an appropriate position. Similarly, even in the catheter device 1, it is also possible not to integrate the intensity of the sound wave.

In addition, it is also possible to perform the calculations other than the integration on the "information related to the return light" and then store the calculation result in the captured image storage memory 35. For example, it may be determined whether the information is a normal value or an abnormal value, and an integrated value obtained by integration may be stored only if it is determined that the information is a normal value. In addition, for example, a plurality of "information related to the return light" may be digitally processed, and the median value thereof may be stored in the captured image storage memory 35. In such a case, the value stored in the captured image storage memory 35 can be abstractly expressed as "value obtained by performing predetermined processing on information related to return light".

In addition, in each of the embodiments, the laser is turned on (periodically irradiated) for the period in which the amplitude of the amplitude modulation waveform am output from the amplitude modulation waveform generation unit 2004 of the driving signal generation unit 20 is linearly increased from 0 as shown in FIG. 5C. It means that the laser is turned on for the period in which the spiral trajectory of the laser irradiation is drawn from the inner circumferential side to the outer circumferential side. On the contrary, the laser may be turned on for the period in which the amplitude of the amplitude modulation waveform am is linearly decreased to return to 0, that is, for the period in which the spiral trajectory of laser irradiation is drawn from the outer circumferential side toward the inner circumferential side. The waveform of the amplitude modulation waveform am is not limited to that shown in FIG. 5C.

In addition, in each of the embodiments, the trajectory of the light emitted from the light guide path 102 is formed in the spiral shape. Ideally, the spiral trajectory becomes substantially circular both on the outer circumferential side and the inner circumference, when focusing on one turn of the spiral trajectory. However, the distortion occurs in the emission direction of the laser, and therefore the shape is not a circle but an ellipse. In addition, when the speed of modulating the amplitude is relatively fast with respect to the change in the ellipticity, there is a possibility that one circling trajectory and the next circling trajectory intersect with each other. Therefore, the spiral trajectory in the present specification also includes such a case.

That is, the spiral trajectory in the present specification indicates a trajectory that changes from the inner circumference to the outer circumference or from the outer circumference to the inner circumference when caught in a macro level, but the spiral trajectory is not necessarily a general spiral when caught in the macro level.

In addition, since the catheter device 1 according to the first embodiment has the optical scanning unit 10, the catheter device 1 may be read as an optical scanning device. Since the optical scanning unit 10 is also included in other embodiments, similarly, the catheter device can be read as the optical scanning device.

It is to be noted that the present invention is not limited to the above-described embodiments, and includes various modified examples in addition to the above-described modified examples. For example, the above-described embodiments have been described in detail in order to explain the present invention in an easy-to-understand manner, and are not necessarily limited to those having all the configurations described. In addition, it is possible to replace a part of the configuration of one embodiment with the configuration of another embodiment, and add the configuration of another embodiment to the configuration of one embodiment. In addition, with respect to a part of the configuration of each of the embodiments, it is possible to add, delete, or replace the configuration of another embodiment.

In addition, a part or all of the above-described configurations, functions, processing units, processing means, and the like may be designed in, for example, an integration unit and the like to be realized by hardware. In addition, each of the above-described configurations, functions, and the like may be realized by software which interprets and executes program that allows the processor to realize each function. Information such as a program, a table, a file, and the like realizing each function can be stored in a memory, recording devices such as a hard disk and a solid state drive (SSD), or recording media such as an IC card, an SD card, and a DVD.

In addition, control lines and information lines indicate what is considered to be necessary for explanation, and all control lines and information lines required for products are not necessarily shown. In practice, it can be considered that almost all the configurations are connected to each other.

What is claimed is:

1. An optical scanning device, comprising:
    an optical scanner configured to repeatedly scan an irradiation destination of irradiation light to a predetermined trajectory;
    a light emission controller configured to control light emission of the irradiation light to irradiate irradiation points to the predetermined trajectory; and
    a driving signal generator configured to generate a driving signal for driving the optical scanner,
    wherein the light emission controller irradiates the irradiation points to the predetermined trajectory so that the irradiation points are substantially uniformly dispersed in a region in which a density of the irradiation points is relatively low in a region in which the irradiation light is irradiated,
    wherein with respect to any irradiation point P in the region in which the density of the irradiation points is relatively low in the region in which the irradiation light is irradiated,
    when a distance to an irradiation point A closest to the irradiation point P is defined as a, and a distance to an irradiation point B closest to the irradiation point P among the irradiation points existing in a direction that is not substantially parallel to a line segment PA with the irradiation point P as a base point is defined as b,
    a distance between an irradiation point irradiated following the irradiation point P by the light emission controller control unit and the irradiation point P is equal to or more than the b, and the a and b are substantially equal.

2. The optical scanning device according to claim 1, wherein the optical scanner repeatedly scans the irradiation destination of the irradiation light to a spiral trajectory.

3. The optical scanning device according to claim 2, wherein the driving signal generator generates the driving signal using a sinusoidal component having a predetermined driving cycle $T_{drv}$ as a main component, and
    with respect to any irradiation point P irradiated to an outermost circumference of the region in which the irradiation light is irradiated when a radius of a substantially circular trajectory on an outermost circumference of the spiral trajectory is set to R,
    when a distance to an irradiation point A closest to the irradiation point P is defined as a, and a distance to an irradiation point B closest to the irradiation point P among the irradiation points existing in a direction that is not substantially parallel to a line segment PA with the irradiation point P as a base point is defined as b,
    a time $T_{dot}$ taken to irradiate an irradiation point after the irradiation point P is irradiated by the light emission controller satisfies the following Mathematical Formula (1),

[Mathematical Formula 31]

$$T_{dot} > T_{drv} \cdot \frac{b}{2\pi R} \tag{31}$$

and the a and b are substantially equal.

4. The optical scanning device according claim 1, wherein the a and b satisfy the following Mathematical Formula (2),

[Mathematical Formula 32]

$$1 \leq b/a \leq 2 \tag{32}$$

5. The optical scanning device according to claim 1, wherein with respect to a substantially parallelogram constituted by four neighboring irradiation points in the region in which the density of the irradiation points is relatively low in the region in which the irradiation light is irradiated,
    any two of the four irradiation points are not irradiation points continuously irradiated and lengths of adjacent sides of the substantially parallelogram are substantially equal.

6. The optical scanning device according to claim 1, wherein the optical scanner includes:
    a light guide path configured to direct, from a light exiting end, light incident from a light incident end; and
    a vibration unit configured to vibrate the light exiting end.

7. The optical scanning device according to claim 1, comprising:
    a receiving unit configured to receive a physical phenomenon occurring as a result of the irradiation of the irradiation light; and
    an imager configured to capture an image based on the received physical phenomenon.

8. The optical scanning device according to claim 7, wherein the receiving unit receives a sound wave as the physical phenomenon occurring as the result of the irradiation of the irradiation light, and
    the imager captures the image based on the received sound wave.

9. The optical scanning device according to claim 7, wherein the receiving unit receives a reflected light as the physical phenomenon occurring as the result of the irradiation of the irradiation light, and
    the imager captures the image based on the received reflected light.

10. The optical scanning device according to claim 1, wherein the light emission controller periodically controls the emission of the irradiation light.

11. The optical scanning device according to claim 2, wherein the light emission controller periodically controls the emission of the irradiation light depending on a light emission frequency $f_{dot}$,
    the driving signal generator generates the driving signal using a sine wave of a frequency $f_{drv}$ as a main component, a number of substantially circular trajectories constituting the spiral trajectory is $N_{frame}$, and α is defined by the following Mathematical Formula (3),

[Mathematical Formula 33]

$$\alpha = f_{dot}/f_{drv} \quad (33)$$

and among positive integers equal to or less than 0.1 times $N_{frame}$, when N making α×N most approximate an integer value is defined as $N_p$, the following Mathematical Formula (4) is satisfied.

[Mathematical Formula 34]

$$0.5 \leq \frac{2\pi}{\alpha N_p \sqrt{\left\{\frac{2\pi}{\alpha} \cdot (\alpha N_p - \text{round}(\alpha N_p))\right\}^2 + \left(\frac{N_p}{N_{frame}}\right)^2}} \leq 2 \quad (34)$$

12. The optical scanning device according to claim 2, wherein the light emission controller periodically controls the emission of the irradiation light depending on a light emission frequency $f_{dot}$, the driving signal generator generates the driving signal using a sine wave of a frequency $f_{drv}$ as a main component, and when a number of substantially circular trajectories constituting the spiral trajectory is $N_{frame}$, the following Mathematical Formula (5) is satisfied.

[Mathematical Formula 35]

$$\left| \text{round}\left(\frac{f_{dot}}{f_{drv}}\right) - \frac{f_{dot}}{f_{drv}} \right| \times 0.1 N_{frame} \geq 1 \quad (35)$$

13. The optical scanning device according to claim 1, comprising:

a frequency controller configured to change a frequency of a sine wave which is a main component of the driving signal, wherein the frequency controller changes the frequency of the sine wave while avoiding a predetermined frequency band.

14. The optical scanning device according to claim 1, wherein the light emission controller changes a time interval $T_{dot}$ from irradiation of any irradiation point in the region in which the density of the irradiation points is relatively low in the region in which the irradiation light is irradiated to irradiation of a next irradiation point.

15. The optical scanning device according to claim 1, wherein the driving signal generator generates the driving signal using a sine wave of a frequency $f_{drv}$ a main component, the light emission controller changes a time interval $T_{dot}$ from irradiation of any irradiation point to irradiation of a next irradiation point, and the time interval $T_{dot}$ satisfies the following Mathematical Formula (6).

[Mathematical Formula 36]

$$T_{dot} > \frac{T_{drv}}{50} \quad (36)$$

16. The optical scanning device according to claim 2, wherein a number of substantially circular trajectories constituting the spiral trajectory is $N_{frame}$, α is defined by the following Mathematical Formula (7),

[Mathematical Formula 37]

$$\alpha = f_{dot}/f_{drv} \quad (37)$$

among positive integers equal to or less than 0.1 times $N_{frame}$, when N making α×N most approximate an integer value is defined as $N_p$, and the light emission controller changes a time interval $T_{dot}$ from irradiation of any irradiation point in the region in which the density of the irradiation points is relatively low in the region in which the irradiation light is irradiated to irradiation of a next irradiation point within $(N_p-1) \times T_{drv}$.

17. A catheter device, comprising:

an optical scanner configured to repeatedly scan an irradiation destination of irradiation light to a predetermined trajectory;

a light emission controller configured to control light emission of the irradiation light to irradiate irradiation points to the predetermined trajectory;

a driving signal generator configured to generate a driving signal for driving the optical scanner;

a receiving unit configured to receive a sound wave occurring as a result of the irradiation of the irradiation light;

an imager configured to capture an image based on the received sound wave, wherein the light emission controller irradiates the irradiation points to the predetermined trajectory so that the irradiation points are substantially uniformly dispersed in a region in which a density of the irradiation points is relatively low in a region in which the irradiation light is irradiated; and a frequency controller configured to change a frequency of a sine wave which is a main component of the driving signal, wherein the frequency controller changes the frequency of the sine wave while avoiding a predetermined frequency band.

18. An optical scanning device, comprising:

an optical scanner configured to repeatedly scan an irradiation destination of irradiation light to a predetermined trajectory;

a light emission controller configured to control light emission of the irradiation light to irradiate irradiation points to the predetermined trajectory; and a driving signal generator configured to generate a driving signal for driving the optical scanner, wherein the light emission controller irradiates the irradiation points to the predetermined trajectory so that the irradiation points are substantially uniformly dispersed in a region in which a density of the irradiation points is relatively low in a region in which the irradiation light is irradiated, and wherein the light emission controller changes a time interval $T_{dot}$ from irradiation of any irradiation point in the region in which the density of the irradiation points is relatively low in the region in which the irradiation light is irradiated to irradiation of a next irradiation point.

19. The optical scanning device according to claim 18, wherein with respect to any irradiation point P in the region in which the density of the irradiation points is relatively low in the region in which the irradiation light is irradiated, when a distance to an irradiation point A closest to the irradiation point P is defined as a, and a distance to an irradiation point B closest to the irradiation point P among the irradiation points existing in a direction that is not substantially parallel to a line segment PA with the irradiation point P as a base point is defined as b, a distance between an irradiation point irradiated following the irradiation point P by the light emission controller control unit and the irradiation point P is equal to or more than the b, and the a and b are substantially equal.

20. The optical scanning device according to claim 1, wherein the optical scanner repeatedly scans the irradiation destination of the irradiation light to a spiral trajectory.

* * * * *